US010456461B2

United States Patent
Pletnev et al.

(10) Patent No.: US 10,456,461 B2
(45) Date of Patent: *Oct. 29, 2019

(54) CONSTRUCTION OF WEST NILE VIRUS AND DENGUE VIRUS CHIMERAS FOR USE IN A LIVE VIRUS VACCINE TO PREVENT DISEASE CAUSED BY WEST NILE VIRUS

(71) Applicants: The United States of America, as represented by the Secretary, Dept. of Health and Human Services, Rockville, MD (US); The Government of the United States, as Represented by The Secretary of The Army, Fort Detrick, MD (US)

(72) Inventors: Alexander G. Pletnev, Gaithersburg, MD (US); Joseph R. Putnak, Silver Spring, MD (US); Robert M. Chanock, Bethesda, MD (US); Brian R. Murphy, Bethesda, MD (US); Stephen S. Whitehead, Bethesda, MD (US); Joseph E. Blaney, Gettysburg, PA (US)

(73) Assignees: The United States of America, as represented by the Secretary, Department of Health and Human Services, Rockville, MD (US); The Government of the United States, as represented by the Secretary of The Army, Fort Detrick, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,624

(22) Filed: Jul. 2, 2018

(65) Prior Publication Data

US 2018/0369358 A1 Dec. 27, 2018

Related U.S. Application Data

(60) Continuation of application No. 14/305,572, filed on Jun. 16, 2014, now Pat. No. 10,058,602, which is a division of application No. 10/871,775, filed on Jun. 18, 2004, now Pat. No. 8,778,671, which is a continuation of application No. PCT/US03/00594, filed on Jan. 9, 2003.

(60) Provisional application No. 60/347,281, filed on Jan. 10, 2002.

(51) Int. Cl.
*A61K 39/12* (2006.01)
*C12Q 1/6888* (2018.01)
*C07K 14/005* (2006.01)
*C12N 7/00* (2006.01)
*C12N 15/86* (2006.01)
*A61K 39/00* (2006.01)

(52) U.S. Cl.
CPC ............ *A61K 39/12* (2013.01); *C07K 14/005* (2013.01); *C12N 7/00* (2013.01); *C12N 15/86* (2013.01); *C12Q 1/6888* (2013.01); *A61K 2039/5254* (2013.01); *A61K 2039/5256* (2013.01); *A61K 2039/53* (2013.01); *C12N 2770/24122* (2013.01); *C12N 2770/24134* (2013.01); *C12N 2770/24143* (2013.01); *C12N 2770/24162* (2013.01); *Y02A 50/386* (2018.01); *Y02A 50/394* (2018.01)

(58) Field of Classification Search
None
See application file for complete search history.

(56) References Cited

U.S. PATENT DOCUMENTS

| 7,094,411 | B2   | 8/2006 | Kinney et al. |                      |
| --------- | ---- | ------ | ------------- | -------------------- |
| 8,778,671 | B2 * | 7/2014 | Pletnev       | A61K 39/12 435/320.1 |
| 10,058,602| B2 * | 8/2018 | Pletnev       | A61K 39/12           |

FOREIGN PATENT DOCUMENTS

| WO | WO 93/06214 | 4/1993 |
| WO | WO 00/57910 | 10/2000 |

OTHER PUBLICATIONS

Luo et al. (F1000Research, 2018, p. 1-8).*
Anderson et al., "Isolation of West Nile virus from mosquitoes, crows, and a cooper's hawk in Connecticut," *Science* 286:2331-2333, 1999.
Blaney et al., "Chemical mutagenesis of dengue virus type 4 yields mutant viruses which are temperature sensitive in Vero cells or human liver cells and attenuated in mice," *J. Virol.* 75:9731-9740, 2001.
Bray et al., "Construction of intertypic chimeric dengue viruses by substitution of structural protein genes" *PNAS USA* 88:10342-10346, 1991.
Bray et al., "Monkeys immunized with intertypic chimeric dengue viruses are protected against wild-type virus challenge" *J. Virol.* 70:4162-4166, 1996.
Calisher et al., "Antigenic relationships between flaviviruses as determined by cross-neutralization tests with polyclonal antisera," *J. Gen. Virol.* 70:37-43, 1989.
Caufour et al., "Construction, characterization and immunogenicity of recombinant yellow fever 17D-dengue type 2 viruses," *Virus Res.* 79:1-14, 2001.
Chambers et al., "Yellow fever/Japanese encephalitis chimeric viruses: construction and biological properties," *J. Virol.* 73:3095-3101, 1999.

(Continued)

*Primary Examiner* — Agnieszka Boesen
(74) *Attorney, Agent, or Firm* — Klarquist Sparkman, LLP

(57) ABSTRACT

The present invention relates to attenuated, immunogenic West Nile virus chimeras built on a dengue virus backbone for the production of immunogenic, live, attenuated West Nile virus vaccines.

12 Claims, 6 Drawing Sheets

Specification includes a Sequence Listing.

(56) References Cited

OTHER PUBLICATIONS

Davis et al., "West Nile virus recombinant DNA vaccine protects mouse and horse from virus challenge and expresses in vitro a noninfectious recombinant antigen that can be used in enzyme-linked immunosorbent assays," *Journal of Virology*, vol. 75, pp. 4040-4047, 2001.
Dauphin et al., "West Nile virus: recent trends in diagnosis and vaccine development," *Vaccine*, vol. 25, pp. 5563-5576, 2007.
Durbin et al., "Attenuation and immunogenicity in humans of a live dengue virus type-4 vaccine candidate with a 30 nucleotide deletion in its 3'-untranslated region," *Am. J. Trop. Med. Hyg.* 65:405-413, 2001.
Fu et al., "Full-Length cDNA Sequence of Dengue Type 1 Virus (Singapore Strain S275/90)," *Virology* 188:953-958, 1992.
Guirakhoo et al, "Recombinant chimeric yellow fever-dengue type 2 virus is immunogenic and protective in nonhuman primates," *J. Virol.* 74:5477-5485, 2000.
Guirakhoo et al., "Construction, Safety, and Immunogenicity in Nonhuman Primates of a Chimeric Yellow Fever-Dengue Virus tetravalent Vaccine," *Journal of Virology*, 75(16):7290-7304, 2001.
Halevy et al., "Loss of active neuroinvasiveness in attenuated strains of west Nile virus: pathogenicity in immunocompetent and SCID mice," *Arch. Virol.* 137:355-370, 1994.
Huang et al., "Chimeric dengue type 2 (vaccine strain PDK-53)/dengue type 1 virus as a potential candidate dengue type 1 virus vaccine," *J. Virol.* 74:3020-3028, 2000.
International Search Report dated Apr. 24, 2003, and dated Jun. 19, 2003, for Application No. PCT/US03/00594.
Lanciotti et al., "Origin of the West Nile virus responsible for an outbreak of encephalitis in the northeastern United States," *Science* 286:2333-2337, 1999.
Lee et al., "Mutagenesis of the signal sequence of yellow fever virus prM protein: enhancement of signalase cleavage in vitro is lethal for virus production," *J. Virol.* 74:24-32, 2000.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," *Journal of Virology*, 70:3930-3937, 1996.
Monath et al., "West Nile Virus Vaccine," *Current Drug Targets* 1(1):37-50, 2001.
Monath, "Prospects for Development of a Vaccine Against the West Nile Virus," *Annals of the N.Y. Academy of Sciences*, 951:1-12, 2001.
Pletnev et al., "Construction and characterization of chimeric tick-borne encephalitis/ dengue type 4 viruses," *PNAS USA* 89:10532-10536, 1992.
Pletnev et al., "Chimeric tick-borne encephalitis and dengue type 4 viruses: effects of mutations on neurovirulence in mice," *J. Virol.* 67:4956-4963, 1993.
Pletnev et al., "Attenuation of the Langat tick-borne flavivirus by chimerization with mosquito-borne flavivirus dengue type 4," *PNAS USA* 95:1746-1751, 1998.
Pletnev et al., "Chimeric Langat/dengue viruses protect mice from heterologous challenge with the highly virulent strains of tick-borne encephalitis virus" *Virology* 274:26-31, 2000.
Pletnev, "Infectious cDNA clone of attenuated Langat tick-borne flavivirus (strain E5) and a 3' deletion mutant constructed from it exhibit decreased neuroinvasiveness in immunodeficient mice," *Virology* 282:288-300. 2001.
Pletnev et al., "Tick-borne Langat/mosquito-borne dengue flavivirus chimera, a candidate live attenuated vaccine for protection against disease caused by members of the tick-borne encephalitis virus complex: evaluation in rhesus monkeys and in mosquitoes," *J. Virol.* 75:8259-8267, 2001.
Pletnev et al., "West Nile virus/dengue type 4 virus chimeras that are reduced in neurovirulence and peripheral virulence without loss of immunogenicity or protective efficacy" *PNAS USA* 99:3036-3041, 2002.
Pletnev et al., "Molecularly Engineered Live-Attenuated Chimeric West Nile/Dengue Virus Vaccines Protect Rhesus Monkeys from West Nile Virus," *Virology*, vol. 314, No. 1, pp. 190-195, 2003.
Pletnev et al., "Chimeric West Nile/Dengue Virus Vaccine Candidate: Preclinical Evaluation in Mice, Geese and Monkeys for Safety and Immunogenicity," *Vaccine*, vol. 24, No. 40-41, pp. 6392-6404, 2006.
Stocks et al., "Signal peptidase cleavage at the flavivirus C-prM junction: dependence on the viral NS2B-3 protease for efficient processing requires determinants in C, the signal peptide, and prM," *J. Virol.* 72:2141-2149, 1998.
Supplemental European Search Report completed on Aug. 18, 2009, for corresponding Application No. EP 03 72 9602.
Van Der Most et al., "Chimeric yellow fever/dengue virus as a candidate dengue vaccine: quantitation of the dengue virus-specific CD8 T-cell response," *J. Virol.* 74:8094-8101, 2000.
Wang. et al., "Immunization of mice against West Nile virus with recombinant envelope protein," *J. Immunol.* 167:5273-5277, 2001.

* cited by examiner

Positive-sense RNA virus:

| | Structural | | | Non-structural protein genes | | | | | | |
|---|---|---|---|---|---|---|---|---|---|---|
| 5' C | prM | E | NS1 | 2A | 2B | NS3 | 4A | 4B | NS5 | 3' |

DEN4

WN

New WN/DEN4 Chimeric Flavivirus:

- Infectious RNA transcribed in vitro from cDNA clones
- Infectious RNA transfected into cell culture (C6/36, Vero)
- Progeny virus recovered and evaluated in susceptible animals

*FIG. 1B*

```
                                  1st                              2nd
                               junction                         junction
                                C/preM                              E
                                                                              No. clones tested/
                                                                    WN cDNA   No. viable virus
                                                                              recovered K   K   R ▼ G   G   R   T   G   I   A          I   N   A   R   D
    WN  AAG AAA AGA GGA GGA AAG ACC GGA ATT GCA ...... ATC AAT GCT CGT GAT   403-2400    NA**

R   K   R ▼ S   T   I   T   L   L   C          L   N   S   R   N
   DEN4 AGA AAA AGG TCA ACG ATA ACA TTG CTG TGC ...... CTG AAC TCG AGG AAC                NA

WN/DEN4:
         R   K   R ▼ S   A   V*  T   G   I   A          I   N   S   R   N
 group 1 AGA AAA AGG TCT GCA GTG ACC GGA ATT GCA ...... ATC AAC TCG AGG AAC  419-2390     7/0
                      PstI                                      XhoI R   K   R ▼ S   A   G*  T   G   I   A          I   N   S   R   N
 group 2 AGA AAA AGG TCT GCA GGG ACC GGA ATT GCA ...... ATC AAC TCG AGG AAC  419-2390     6/0

R   K   R ▼ S   A   D*  T   G   I   A          I   N   S   R   N
 group 3 AGA AAA AGG TCT GCA GAC ACC GGA ATT GCA ...... ATC AAC TCG AGG AAC  420-2390     3/0

R   K   R ▼ S   A   D*  T   G   T   A          I   N   S   R   N
 group 4 AGA AAA AGG TCT GCA GAC ACC GGA ACT GCA ...... ATC AAC TCG AGG AAC  420-2390     2/2†
```

*FIG. 2*

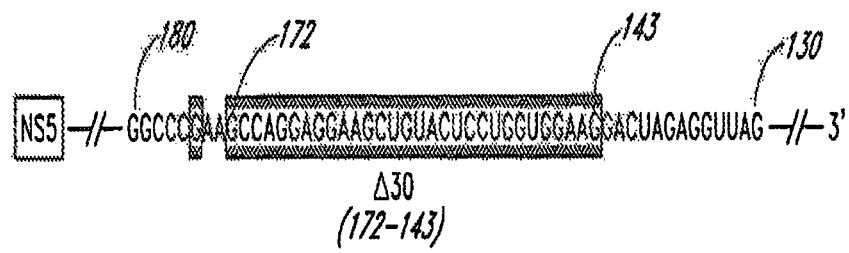

FIG. 4A

```
DEN4      GGGGCCCGAAGCCAGGAGGAAGCUGUACUCCUGGUGGAAGGACUAGA
DEN4Δ30   GGGGCCC-AA-----------------------------GACUAGA
DEN1      GGGGCCC-AACACCAGGGGAAGCUGUACCCUGGUGGUAAGGACUAGA
DEN1Δ30   GGGGCCC-AA-----------------------------GACUAGA

DEN1      GGGGCCC-AacaccagggGAAGCUGUAcccuggugguAAGGACUAGA
DEN2      GGGGCCC-AaggugagauGAAGCUGUAgucucacuggAAGGACUAGA
DEN3      GGGGCCCgAgcucugaggGAAGCUGUAccuccuugcaAAGGACUAGA
DEN4      GGGGCCCgAagccaggagGAAGCUGUAcuccugguggAAGGACUAGA
```

FIG. 4B

|  Completed Δ30 viruses  |  |  | Proposed |
| --- | --- | --- | --- |
| DEN1 | DEN4 | DEN2 | DEN3 |

```
    GCA                   AGC                  AGCAA                 GCA
      G    CAACAA            A    ACAAAA          C    ACAAAA           G    AUAAAA
      C  A                   A  C                 A  A                  C  A
      A  A  G A              A  A  G A            A  A  G A             A  A  G A
      G-C    G   G           A A

CONSTRUCTION OF WEST NILE VIRUS AND DENGUE VIRUS CHIMERAS FOR USE IN A LIVE VIRUS VACCINE TO PREVENT DISEASE CAUSED BY WEST NILE VIRUS

RELATED APPLICATIONS

This application is a continuation of co-pending U.S. application Ser. No. 14/305,572, filed Jun. 16, 2014, which is a divisional of U.S. application Ser. No. 10/871,775, filed Jun. 18, 2004, now U.S. Pat. No. 8,778,671, issued Jul. 15, 2014, which is a continuation and claims the benefit of priority of International Application No. PCT/US03/00594 filed Jan. 9, 2003, designating the United States of America and published in English on Jul. 24, 2003 as WO 03/059384, which claims the benefit of priority of U.S. Provisional Application No. 60/347,281 filed Jan. 10, 2002, all of which are hereby expressly incorporated by reference in their entireties.

The Sequence Listing is submitted as an ASCII text file in the form of the file named Sequence_Listing.txt, which was created on Jul. 2, 2018, and is 106,339 bytes, which is incorporated by reference herein.

FIELD OF THE INVENTION

The present invention relates to attenuated, immunogenic West Nile virus chimeras built on a dengue virus backbone for the production of immunogenic, live, attenuated West Nile virus vaccines.

BACKGROUND OF THE INVENTION

Beginning with FIG. 1A, the flavivirus genome is a single-stranded, positive-sense RNA approximately 11 kb in length, containing a 5' untranslated region (5' UTR); a coding region encoding the three viral structural proteins; seven nonstructural proteins, designated NS1, NS2A, NS2B, NS3, NS4A, NS4B, NS5; and a 3' untranslated region (3' UTR). The viral structural proteins include the capsid (C), premembrane/membrane (prM) and envelope (E) proteins. The structural and nonstructural proteins are translated as a single polyprotein. The polyprotein is then processed by cellular and viral proteases.

West Nile virus (WN) belongs to the family Flaviviridae that comprises more than 60 viruses, many of which are important human pathogens. WN is a member of the Japanese encephalitis virus (JE) serocomplex of mosquito-borne flaviviruses that includes St. Louis encephalitis, J E, and Murray Valley encephalitis viruses (Calisher, C. H. et al. 1989 *J Gen Virol* 70:27-43; Burke, D. S. & Monath, T. P. 2001 in: *Fields Virology*, eds. Knipe, D. M. & Howley, P. M. Lippincott Williams and Wilkins, Philadelphia, 4-th ed., pp, 1043-1125). Like other members of the JE antigenic complex, WN is maintained in a natural cycle that involves mosquito vectors and birds, while humans and equines are usually incidental hosts. For many years WN has been recognized as one of the most widely distributed flaviviruses with a geographic range including Africa, Australia, Europe, the Middle East and West Asia (Burke, D. S. & Monath, T. P. 2001 in: *Fields Virology*, eds. Knipe, D. M. & Howley, P. M. Lippincott Williams and Wilkins, Philadelphia, 4-th ed., pp. 1043-1125; Hayes, C. G. 1989 in: *The Arboviruses: Epidemiology and Ecology*, ed. Monath T. P. Boca Raton, Fla. CRC Press, Volume V, pp. 59-88). During 1999 WN first established itself in the USA in the Northeast and Mid-Atlantic States and more recently this virus extended its range to include the Southeastern and Western States (Anderson, J. F. et al. 1999 *Science* 286:2331-2333; Lanciotti, R. S. et al. 1999 *Science* 286:2333-2337; Campbell, G. L, et al. 2002 *Lancet* 2:519-529). In endemic regions, most human WN infections are asymptomatic or cause mild illness with symptoms of low-grade fever, headache, body aches, rash, myalgia, and polyarthropathy. However, human epidemics with severe disease have been reported in Israel, France, Romania, and Russia. In acute severe illness, the virus can cause hepatitis, meningitis and encephalitis leading to paralysis, and coma resulting in death. The neuropathologic lesions are similar to those of JE, with diffuse CNS inflammation and neuronal degeneration. Virus is also found in the spleen, liver, lymph nodes, and lungs of infected individuals. During the 1999 outbreak of WN in the USA, more than 60 people became ill and 7 died, while during 2002, morbidity was 3873 cases and there were 246 deaths (CDC Report: West Nile Update Current case Count, Jan. 2, 2003). Because of the recent and unexpected spread of WN from the Northeast to the Southeast and the West of the USA, this virus is considered a significant emerging disease threat that has embedded itself over a considerable region of the country. Currently, a licensed human vaccine is not available for prevention of WN disease. Mosquito control is the only practical strategy to combat the spread of disease, but effective spraying is difficult to perform in urban areas. Clearly, an effective vaccine is needed to protect at-risk populations.

Dengue viruses are mosquito-borne pathogens of the genus Flavivirus (family Flaviviridae). Four serotypes of dengue virus (DEN) have been identified, including dengue type 1 virus (DEN1), dengue type 2 virus (DEN2), dengue type 3 virus (DEN3) and dengue type 4 virus (DEN4). Live, attenuated dengue viruses of all four serotypes have been developed at Mahidol University in Thailand by passaging the wild-type viruses in primary dog kidney cell culture (Sabchareon, A. et al. 2002 *Am J Trop Med Hyg* 66:264-272). These are currently the least promising live, attenuated vaccine candidates for immunization against dengue virus infection and/or disease because they are not well characterized as to the relative contributions of attenuation-associated mutations to the actual mechanism of attenuation nor as to the potential for reverse mutations to revert any of the vaccine candidates to the virulent biological phenotype of the wild-type dengue virus. These vaccine candidates have been designated by a combination of their dengue serotype, the cell line through which they were passaged and the number of times they were passaged. Thus, a dengue serotype 1 wild-type virus passaged in primary dog kidney (PDK) cells 13 times is designated as DEN1 PDK13 virus. Other vaccine candidates are DEN2 PDK53, DEN3 PGMK30/FRhL3 (thirty passages in primary green monkey kidney cells, followed by three passages in fetal rhesus lung cells) and DEN4 PDK48. These four candidate vaccine viruses were derived by tissue culture passage of wild-type parental DEN1 16007, DEN2 16681, DEN3 16562 and DEN4 1036 viruses, respectively.

Except for DEN2 PDK53 virus, the number and identity of the genetic mutations that accrued during multiple passages in cell culture and that are associated with the attenuation phenotype of the vaccine candidates are unknown. Neither the relative contributions of such attenuation-associated mutations to the actual mechanism of attenuation, nor the potential for reverse mutations to revert any of the vaccine candidates to the virulent biological phenotype of the wild-type dengue virus are known for any of these four vaccine candidates. An understanding of the characteristics of a vaccine candidate is critical for the prediction of its stability and safety.

Accordingly, there is a need for attenuated, yet immunogenic flaviviruses to be used in the development of flavivirus vaccines to confer protection against flaviviruses. What would be ideal is a vaccine that would simultaneously protect an individual against flavivirus disease and be sufficiently characterized so that stability and safety are predictable.

SUMMARY OF THE INVENTION

Chimeric flaviviruses that are attenuated and immunogenic are provided. Chimeric viruses containing the non-structural protein genes of a dengue virus are used as a backbone into which the structural protein genes of a West Nile virus are substituted. These chimeric viruses exhibit pronounced immunogenicity in the absence of the accompanying clinical symptoms of viral disease. The attenuated chimeric viruses are effective as immunogens or vaccines and may be combined in a pharmaceutical composition to confer immunity against West Nile virus.

BRIEF DESCRIPTION OF THE DRAWING

FIG. 1B shows a strategy used to replace the genes for prM and E proteins of DEN4 with the corresponding genes of West Nile virus to produce WN/DEN4 chimeras that serve as candidate attenuated vaccine strains.

FIG. 2 shows the structure of portions of chimeric WN/DEN4 cDNAs. The top bar depicts the chimeric virus cDNA genome from the 5' terminus of the genome to the 3' terminus of the NS1 gene. The solid black boxes represent hydrophobic domains in the polyprotein. The vertical solid arrow indicates the position of a potential NS2B-NS3 protease cleavage site in the polyprotein between the C and prM proteins (the first junction in chimeric genome). Cleavage sites for cellular signalase are indicated by open triangles (∇). A restriction enzyme-cleaved WN cDNA fragment bearing the sequence for the WN premembrane (prM) and envelope glycoprotein (E) structural protein genes was inserted into DEN4 cDNA at PstI and XhoI sites, which are underlined. The second junction is located in the COOH-terminus of the WN E protein between the two hydrophobic domains. The amino acid and nucleotide sequences of WN are presented in bold letters, and nucleotide numbering system is from GenBank accession No. AF196835. Infectivity of RNA transcripts from full-length cDNA constructs was tested by transfecting simian Vero or C6/36 mosquito cells and evaluating cell cultures for evidence of infection by immunofluorescence assay. The two clones in group 4 sustained a mutation of the amino acid +6 downstream from the cleavage site from I (isoleucine) to T (threonine) during cloning of cDNA (represented in the figure). Only these two clones were viable, yielding infectious virus following transfection of full length RNA transcripts.

*Indicates amino acids in chimeric constructs that vary at the 3+ position downstream of protease cleavage site. **Not applicable. ⁺Two infectious chimeric WN/DEN4 viruses, namely clone 18 and 55 from group 4, were isolated.

| Table of Sequences from FIG. 2 | | |
|---|---|---|
| SEQUENCE | SEQ ID NO | SOURCE |
| KKRGGRTGIA | 1 | WN |
| AAGAAAAdAGGAGGAAAGACCGGAATTGCA | 2 | WN |
| RKRSTITLLC | 3 | DEN4 |
| AGAAAAAGGTCAACGATAACATTGCTGTGC | 4 | DEN4 |
| RKRSAVTGIA | 5 | WN/DEN4 |
| AGAAAAAGGTCTGCAGTGACCGGAATTGCA | 6 | WN/DEN4 |
| RKRSAGTGIA | 7 | WN/DEN4 |
| AGAAAAAGGTCTGCAGGGACCGGAATTGCA | 8 | WN/DEN4 |
| RKRSADTGIA | 9 | WN/DEN4 |
| AGAAAAAGGTCTGCAGACACCGGAATTGCA | 10 | WN/DEN4 |
| RKRSADTGTA | 11 | WN/DEN4 |
| AGAAAAAGGTCTGCAGACACCGGAACTGCA | 12 | WN/DEN4 |
| INARD | 13 | WN |
| ATCAATGCTCGTGAT | 14 | WN |
| LNSRN | 15 | DEN4 |
| CTGAACTCGAGGAAC | 16 | DEN4 |
| INSRN | 17 | WN/DEN4 |
| ATCAACTCGAGGAAC | 18 | WN/DEN4 |

Figure 3:
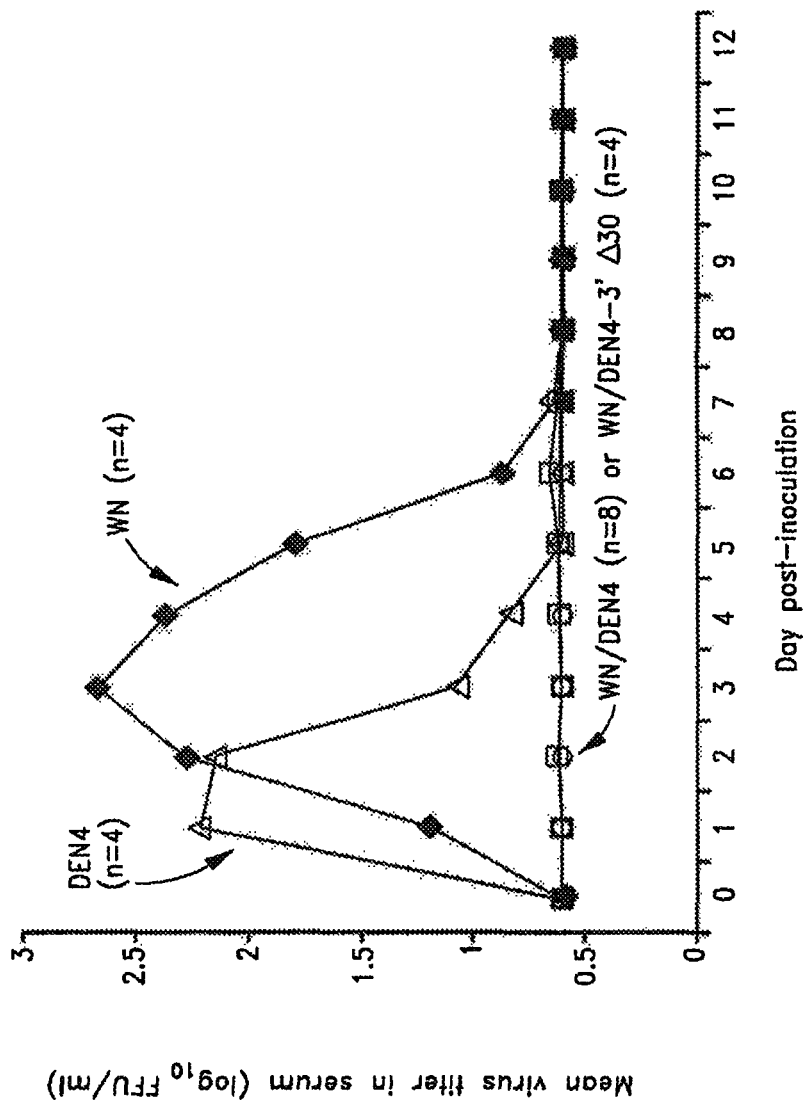

FIG. 3 shows the viremia of rhesus monkeys inoculated with parental WN or DEN4 virus or their WN/DEN4 chimera or its 3' deletion mutant WN/DEN4-3'Δ30. Twenty rhesus monkeys (*Maccaca mulatta*) in groups of 4 were inoculated subcutaneously (SC) with WN, DEN4, WN/DEN4 clone 18 or WN/DEN4-3'Δ30 clone 1. The quantity of virus in monkey serum was determined by direct titration in Vero cells using immunostaining focus-forming assay. Viremia was tested daily for 12 days post-inoculation for each monkey individually. Mean virus titer in serum of each monkey group shown; n is number of monkeys in group. The limit of detection of virus was $10^{0.7}$ FFU/ml, and the WN/DEN4 and WN/DEN4-3'Δ30 viruses were at or below the level of detection of virus in serum.

FIG. 4A shows that the Δ30 mutation removes 30 contiguous nucleotides (shaded) from the 3' UTR of DEN4. Nucleotides are numbered from the 3' terminus. FIG. 4B is a nucleotide sequence alignment of the TL2 region of DEN4 and DEN1 and their Δ30 derivatives. Also shown is the corresponding region for each of the four DEN serotypes, with upper case letters indicating sequence homology among all 4 serotypes, underlining indicating nucleotide pairing to form the stem structure. FIG. 4C shows the predicted secondary structure of the TL2 region of each DEN serotype. Nucleotides that are removed by the Δ30 mutation for the already constructed DEN1Δ30, DEN4Δ30, DEN2Δ30 viruses are indicated (boxed) on the left and the proposed DEN3Δ30 virus is on the right (DEN1-nts 10562-10591, DEN2 Tonga/74-nts 10541-10570, DEN3 Sleman/78-nts 10535-10565, and DEN4-nts 10478-10507).

| | GenBank Accession No. or description |
|---|---|
| Bases 6371 to 6751: | NS4A protein ORF |
| Bases 6752 to 6820: | 2K protein ORF |
| Bases 6821 to 7564: | NS4B protein ORF |
| Bases 7575 to 10264: | NS5 protein ORF |

Table of Sequences from FIG. 4

| SEQUENCE | SEQ ID NO | SOURCE |
|---|---|---|
| GGCCCGAAGCCAGGAGGAAGCUGUACUCCUGGUGGAAGGACUAGAGGUUAG | 19 | DEN4 |
| GGGGCCCGAAGCCAGGAGGAAGCUGUACUCCUGGUGGAAGGACUAGA | 20 | DEN4 |
| GGGGCCCAAGACUAGA | 21 | DEN4Δ30 |
| GGGGCCCAACACCAGGGGAAGCUGUACCCUGGUGGUAAGGACUAGA | 22 | DEN1 |
| GGGGCCCAAGACUAGA | 23 | DEN1Δ30 |
| GGGGCCCAAGGUGAGAUGAAGCUGUAGUCUCACUGGAAGGACUAGA | 24 | DEN2 |
| GGGGCCCGAGCUCUGAGGGAAGCUGUACCUCCUUGCAAAGGACUAGA | 25 | DEN3 |
| GCAGCAGCGGGGCCCAACACCAGGGGAAGCUGUACCCUGGUG GUAAGGACUAGAGGUUAGAGGGAGACCCCCCGCAACAACAA | 26 | DEN1 |
| AGCAAAAGGGGGCCCGAAGCCAGGAGGAAGCUGUACUCCUGG UGGAAGGACUAGAGGUUAGAGGGAGACCCCCAACACAAAA | 27 | DEN4 |
| AGCAACAAUGGGGCCCAAGGUGAGAUGAAGCUGUAGUCUCA CUGGAAGGACUAGAGGUUAGAGGGAGACCCCCCCAAAACAAAA | 28 | DEN2 |
| GCAGCAGCGGGGCCCGAGCUCUGAGGGAAGCUGUACCUCCUU GCAAAGGACUAGAGGUUAGAGGGAGACCCCCGCAAAUAAAA | 29 | DEN3 |

BRIEF DESCRIPTION OF THE SEQUENCES

| | GenBank Accession No. or description |
|---|---|
| DEN1 | U88535 |
| DEN2 | Tonga/74 (SEQ ID No: 30 and 31)* |
| DEN3 | Sleman/78 (SEQ ID No: 32 and 33)** |
| DEN4 | AF326825 |

*DEN2 (Tonga/74) cDNA plasmid p2
Bases 1 to 10713: DEN2 virus genome cDNA:
Bases 97 to 10269: DEN2 polyprotein ORF
Bases 97 to 438: C protein ORF
Bases 439 to 936: prM protein ORF
Bases 937 to 2421: E protein ORF
Bases 2422 to 3477: NS1 protein ORF
Bases 3478 to 4131: NS2A protein ORF
Bases 4132 to 4521: NS2B protein ORF
Bases 4522 to 6375: NS3 protein ORF
Bases 6376 to 6756: NS4A protein ORF
Bases 6757 to 6825: 2K protein ORF
Bases 6826 to 7569: NS4B protein ORF
Bases 7570 to 10269: NS5 protein ORF
**DEN3 (Sleman/78) cDNA plasmid p3
Bases 1 to 10707: DEN3 virus genome cDNA
Bases 95 to 10264: DEN3 polyprotein ORF
Bases 95 to 436: C protein ORF
Bases 437 to 934: prM protein ORF
Bases 935 to 2413: E protein ORF
Bases 2414 to 3469: NS1 protein ORF
Bases 3470 to 4123: NS2A protein ORF
Bases 4124 to 4513: NS2B protein ORF
Bases 4514 to 6370: NS3 protein ORF

DETAILED DESCRIPTION OF THE PREFERRED EMBODIMENT

Immunogenic WN/DEN flavivirus chimeras and methods for preparing the WN/DEN flavivirus chimeras are provided herein. The immunogenic WN/DEN flavivirus chimeras are useful, alone or in combination, in a pharmaceutically acceptable carrier as immunogenic compositions to immunize and protect individuals and animals against infection by West Nile virus.

Chimeras of the present invention comprise nucleotide sequences encoding the immunogenic structural proteins of a West Nile virus and further nucleotide sequences selected from the backbone of a dengue virus. Chimeric viruses derived from the nucleotide sequences can be used to induce an immunogenic response against West Nile virus.

In another embodiment, the preferred chimera is a nucleic acid chimera comprising a first nucleotide sequence encoding at least one structural protein from a West Nile virus, and a second nucleotide sequence encoding nonstructural proteins from a dengue virus. In another embodiment the dengue virus is attenuated. In another embodiment the dengue virus is DEN4. In another embodiment, the structural protein can be the C protein of a West Nile virus, the prM protein of a West Nile virus, the E protein of a West Nile virus, or any combination thereof.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W), As used herein, the terms "virus chimera," "chimeric virus," "flavivirus chimera" and "chimeric flavivirus" means an infectious construct of the invention comprising nucleotide sequences encoding the immunogenicity of a West Nile virus and further nucleotide sequences derived from the backbone of a dengue virus.

As used herein, "infectious construct" indicates a virus, a viral construct, a viral chimera, a nucleic acid derived from a virus or any portion thereof, which may be used to infect a cell.

As used herein, "nucleic acid chimera" means a construct of the invention comprising nucleic acid comprising nucleotide sequences encoding the immunogenicity of a West Nile virus and further nucleotide sequences derived from the backbone of a dengue virus. Correspondingly, any chimeric flavivirus or flavivirus chimera of the invention is to be recognized as an example of a nucleic acid chimera.

The structural and nonstructural proteins of the invention are to be understood to include any protein comprising or any gene encoding the sequence of the complete protein, an epitope of the protein, or any fragment comprising, for example, three or more amino acid residues thereof.

Flavivirus Chimeras

West Nile virus and dengue virus are mosquito-borne flavivirus pathogens. The flavivirus genome contains a 5' untranslated region (5' UTR), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' untranslated region (3' UTR). The viral structural proteins are C, prM and E, and the nonstructural proteins are NS1-NS5. The structural and nonstructural proteins are translated as a single polyprotein and processed by cellular and viral proteases.

The flavivirus chimeras of the invention are constructs formed by fusing structural protein genes from a West Nile virus with non-structural protein genes from a dengue virus, e.g., DEN1, DEN2, DEN3, or DEN4.

The attenuated, immunogenic flavivirus chimeras provided herein contain one or more of the structural protein genes, or antigenic portions thereof, of the West Nile virus against which immunogenicity is to be conferred, and the nonstructural protein genes of a dengue virus.

The chimera of the invention contains a dengue virus genome as the backbone, in which the structural protein gene(s) encoding C, prM, or E protein(s) of the dengue genome, or combinations thereof, are replaced with the corresponding structural protein gene(s) from a West Nile virus that is to be protected against. The resulting chimeric virus has the properties, by virtue of being chimerized with the dengue virus, of attenuation and is therefore reduced in virulence, but expresses antigenic epitopes of the WN structural gene products and is therefore immunogenic.

The genome of any dengue virus can be used as the backbone in the attenuated chimeras described herein. The backbone can contain mutations that contribute to the attenuation phenotype of the dengue virus or that facilitate replication in the cell substrate used for manufacture, e.g., Vero cells. The mutations can be in the nucleotide sequence encoding nonstructural proteins, the 5' untranslated region or the 3' untranslated region. The backbone can also contain further mutations to maintain the stability of the attenuation phenotype and to reduce the possibility that the attenuated virus or chimera might revert back to the virulent wild-type virus. For example, a first mutation in the 3' untranslated region and a second mutation in the 5' untranslated region will provide additional attenuation phenotype stability, if desired. In particular, a mutation that is a deletion of 30 nts from the 3' untranslated region of the DEN4 genome between nts 10478-10507 results in attenuation of the DEN4 virus (Men et al. 1996 *J Virol* 70:3930-3933; Durbin et al. 2001 *Am J Trop Med* 65:405-413). Therefore, the genome of any dengue type 4 virus containing such a mutation at this locus can be used as the backbone in the attenuated chimeras described herein. Furthermore, other dengue virus genomes containing an analogous deletion mutation in the 3' untranslated region of the genomes of other dengue virus serotypes may also be used as the backbone structure of this invention.

Such mutations may be achieved by site-directed mutagenesis using techniques known to those skilled in the art. It will be understood by those skilled in the art that the virulence screening assays, as described herein and as are well known in the art, can be used to distinguish between virulent and attenuated backbone structures.

Construction of Flavivirus Chimeras

The flavivirus chimeras described herein can be produced by substituting at least one of the structural protein genes of the West Nile virus against which immunity is desired into a dengue virus genome backbone, using recombinant engineering techniques well known to those skilled in the art, namely, removing a designated dengue virus gene and replacing it with the desired corresponding gene of West Nile virus. Alternatively, using the sequences provided in GenBank, the nucleic acid molecules encoding the flavivirus proteins may be synthesized using known nucleic acid synthesis techniques and inserted into an appropriate vector. Attenuated, immunogenic virus is therefore produced using recombinant engineering techniques known to those skilled in the art.

As mentioned above, the gene to be inserted into the backbone encodes a West Nile virus structural protein. Preferably the West Nile virus gene to be inserted is a gene encoding a C protein, a prM protein and/or an E protein. The sequence inserted into the dengue virus backbone can encode both the prM and E structural proteins. The sequence inserted into the dengue virus backbone can encode the C, prM and E structural proteins. The dengue virus backbone is the DEN1, DEN2, DEN3, or DEN4 virus genome, or an attenuated dengue virus genome of any of these serotypes, and includes the substituted gene(s) that encode the C, prM and/or E structural protein(s) of a West Nile virus or the substituted gene(s) that encode the prM and/or E structural protein(s) of a West Nile virus. In a particular embodiment of this invention, the substituted gene that encodes the structural protein of a West Nile virus directs the synthesis of a prM protein that contains Asp and Thr, respectively, at a position 3 and 6 amino acids downstream of the cleavage site that separates the capsid protein of DEN and the premembrane protein of West Nile virus.

Suitable chimeric viruses or nucleic acid chimeras containing nucleotide sequences encoding structural proteins of West Nile virus can be evaluated for usefulness as vaccines by screening them for phenotypic markers of attenuation that indicate reduction in virulence with retention of immunogenicity. Antigenicity and immunogenicity can be evaluated using in vitro or in vivo reactivity with West Nile antibodies or immunoreactive serum using routine screening procedures known to those skilled in the art.

Flavivirus Vaccines

The preferred chimeric viruses and nucleic acid chimeras provide live, attenuated viruses useful as immunogens or vaccines. In a preferred embodiment, the chimeras exhibit high immunogenicity while at the same time not producing dangerous pathogenic or lethal effects.

The chimeric viruses or nucleic acid chimeras of this invention can comprise the structural genes of a West Nile virus in a wild-type or an attenuated dengue virus backbone. For example, the chimera may express the structural protein genes of a West Nile virus in either of a dengue virus or an attenuated dengue virus background.

The strategy described herein of using a genetic background that contains nonstructural regions of a dengue virus genome, and, by chimerization, the properties of attenuation, to express the structural protein genes of a West Nile virus has lead to the development of live, attenuated flavivirus vaccine candidates that express structural protein genes of desired immunogenicity. Thus, vaccine candidates for control of West Nile virus pathogens can be designed.

Viruses used in the chimeras described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Chimeric infectious clones are constructed from various flavivirus strains. The cloning of virus-specific cDNA fragments can also be accomplished, if desired. The cDNA fragments containing the structural protein or nonstructural protein genes are amplified by reverse transcriptase-polymerase chain reaction (RT-PCR) from flavivirus RNA with various primers. Amplified fragments are cloned into the cleavage sites of other intermediate clones. Intermediate, chimeric flavivirus clones are then sequenced to verify the sequence of the inserted flavivirus-specific cDNA.

Full genome-length chimeric plasmids constructed by inserting the structural or nonstructural protein gene region of flaviviruses into vectors are obtainable using recombinant techniques well known to those skilled in the art.

Method of Administration

The viral chimeras described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nanoparticles and liposomes. It is expected that from about 1 to about 5 doses may be required per immunization schedule. Initial doses may range from about 100 to about 100,000 PFU or FFU, with a preferred dosage range of about 500 to about 20,000 PFU or FFU, a more preferred dosage range of from about 1000 to about 12,000 PFU or FFU and a most preferred dosage range of about 1000 to about 4000 PFU or FFU. Booster injections may range in dosage from about 100 to about 20,000 PFU or FFU, with a preferred dosage range of about 500 to about 15,000, a more preferred dosage range of about 500 to about 10,000 PFU or FFU, and a most preferred dosage range of about 1000 to about 5000 PFU or FFU. For example, the volume of administration will vary depending on the route of administration. Intramuscular injections may range in volume from about 0.1 ml to 1.0 ml.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

Administration Schedule

The immunogenic or vaccine composition described herein may be administered to humans or domestic animals, such as horses or birds, especially individuals travelling to regions where West Nile virus infection is present, and also to inhabitants of those regions. The optimal time for administration of the composition is about one to three months before the initial exposure to the West Nile virus. However, the composition may also be administered after initial infection to ameliorate disease progression, or after initial infection to treat the disease.

Adjuvants

A variety of adjuvants known to one of ordinary skill in the art may be administered in conjunction with the chimeric virus in the immunogen or vaccine composition of this invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof.

Nucleic Acid Sequences

Nucleic acid sequences of West Nile virus and dengue virus are useful for designing nucleic acid probes and primers for the detection of West Nile virus and dengue virus chimeras in a sample or specimen with high sensitivity and specificity. Probes or primers corresponding to West Nile virus and dengue virus can be used to detect the presence of a vaccine virus. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding West Nile virus and dengue virus or complementary sequences thereof. By "selective" or "selectively" is meant a sequence which does not hybridize with other nucleic acids to prevent adequate detection of the West Nile virus sequence and dengue virus sequence. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in *Molecular Cloning: A Laboratory Manual*, $2^{nd}$ ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of West Nile virus and dengue virus, the degree of complementarity between the hybridizing nucleic acid (probe or primer) and the sequence to which it hybridizes is at least enough to distinguish hybridization with a nucleic acid from other organisms.

The nucleic acid sequences encoding West Nile virus and dengue virus can be inserted into a vector, such as a plasmid, and recombinantly expressed in a living organism to produce recombinant West Nile virus and dengue virus peptide and/or polypeptides.

The nucleic acid sequences of the invention include a diagnostic probe that serves to report the detection of a cDNA amplicon amplified from the viral genomic RNA template by using a reverse-transcription/polymerase chain reaction (RT-PCR), as well as forward and reverse amplimers that are designed to amplify the cDNA amplicon. In certain instances, one of the amplimers is designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer 1996 *Nature Biotechnology* 14:303-308). Molecular beacon assays employ quencher and reporter dyes that differ from those used in the TaqMan assay. These and other detection systems may used by one skilled in the art.

West Nile Virus/Dengue Type 4 Virus Chimeras that are Reduced in Neurovirulence and Peripheral Virulence without Loss of Immunogenicity or Protective Efficacy A candidate live attenuated vaccine strain was constructed for West Nile virus (WN), a neurotropic flavivirus that has recently emerged in the U.S. Considerable attenuation for mice was achieved by chimerization with dengue virus type 4 (DEN4). The genes for the structural premembrane (prM) and envelope (E) proteins of DEN4 present in a full-length infectious cDNA clone were replaced by the corresponding genes of WN strain NY99. Two of 18 full-length cDNA clones of a WN/DEN4 chimera yielded full-length RNA transcripts that were infectious when transfected into susceptible cells. The two infectious clones shared a motif in the transmembrane signal domain located immediately downstream of the NS2B-NS3 protease cleavage site that separates the DEN4 capsid protein and the WN premembrane protein of the chimera. This motif, Asp and Thr at a position 3 and 6 amino acids downstream of the cleavage site, respectively, was not present in the 16 non-infectious cDNA clones. The WN/DEN4 chimera was highly attenuated in mice compared to its WN parent; the chimera was at least 28,500 times less neurovirulent in suckling mice inoculated intracerebrally and at least 10,000 times less virulent in adult mice inoculated intraperitoneally. Nonetheless, the WN/DEN4 chimera and a deletion mutant derived from it, were immunogenic and provided complete protection against lethal WN challenge. These observations provide the basis for pursuing the development of a live attenuated WN vaccine.

Recent advances in recombinant DNA technology have allowed us to develop a novel approach for constructing live attenuated flavivirus vaccines (Pletnev, A. G. et al. 1992 *PNAS USA* 89:10532-10536; Pletnev, A. G. & Men, R. 1998 *PNAS USA* 95:1746-1751; Pletnev, A. G. et al. 2000 *Virology* 274:26-31; Pletnev, A. G. et al. 2001 *J Virol* 75:8259-8267). Our approach was made possible by the conservation among flaviviruses of genome organization, number of viral proteins, replicative strategy, gene expression, virion structure and morphogenesis (Lindenbach, B. D. & Rice, C. M. 2001 in: *Fields Virology*, eds. Knipe, D. M. & Howley, P. M. Lippincott Williams and Wilkins, Philadelphia, 4-th ed., pp. 1043-1125). All flaviviruses have a positive sense non-segmented RNA genome that encodes a single long polyprotein that is processed to yield capsid (C), premembrane (prM) and envelope glycoprotein (E) structural proteins followed by nonstructural proteins NS1, NS2A, NS2B, NS3, NS4A, NS4B, and NS5 in that order. These shared properties suggested that viable chimeric viruses could be produced by replacing the genes for the viral structural proteins in a full-length infectious cDNA clone of a flavivirus with the corresponding viral genes (in cDNA form) of another flavivirus. When tested, this strategy was successful for chimeras that contained the sequence for viral structural proteins prM and E of tick-borne encephalitis virus (TBEV) or tick-borne Langat virus (LGT), while all other sequences were derived from the full-length infectious cDNA of mosquito-borne dengue type 4 virus (DEN4). This indicated that viral structural proteins of a disparate flavivirus, TBEV or LGT, could function in the context of cis-acting 5' and 3' sequences and nonstructural proteins of DEN4. Significantly, both chimeras proved to be highly attenuated in mice with respect to peripheral virulence, namely, the ability of a virus to spread to the CNS from a peripheral site of inoculation and cause encephalitis. Nonetheless, the chimeras proved to be immunogenic and able to induce resistance in mice against challenge with TBEV or LGT (Pletnev, A. G. et al. 1992 *PNAS USA* 89:10532-10536; Pletnev, A. G. & Men, R. 1998 *PNAS USA* 95:1746-1751; Pletnev, A. G. et al. 2000 *Virology* 274:26-31). It appeared that a favorable balance between reduction in virus replication in vivo (attenuation) and induction of protective immunity had been achieved. We interpret this to mean that tick-borne flavivirus prM and E can interact in the context of DEN4 nonstructural proteins and cis-acting 5' and 3' sequences at a level sufficient for infectivity and induction of immunity but not sufficient for full expression of virulence that requires a high level of replication in vivo and ability to spread into the CNS.

Although a logical extension of this strategy was to construct WN/DEN4 chimeras, we realized that viability could not be predicted in advance because some flavivirus combinations such as some Langat virus(prM and E)/dengue virus chimeras, as well as dengue virus(prM and E)/Langat dengue virus chimeras, have not proven to be viable. Nevertheless, we were surprisingly successful in constructing viable WN/DEN4 chimeras in which the structural prM and E protein genes of the distantly related mosquito-borne WN were substituted for the corresponding genes of DEN4. We also generated a WN/DEN4 chimera with a 30 nucleotide deletion in the 3' untranslated region (3' UTR) that had previously been shown to render DEN4 safe but still immunogenic in adult volunteers (Durbin, A. P. et al. 2001 *Am J Trop Med Hyg* 65:405-413). Studies in mice were first performed to evaluate neurovirulence, peripheral virulence, immunogenicity, and protective efficacy of the newly constructed WN/DEN4 chimeric viruses.

Materials and Methods.

Cells and Viruses

Simian Vero cells (WHO seed passage 143) and mosquito C6/36 cells were obtained from Dr. L. Potash (Novavax Inc., Rockville, Md.). These Vero cells are qualified for use in production of candidate human vaccines. Simian LLCMK$_2$ cells were purchased from the American Type Culture Collection (Manassas, Va.). Starting with West Nile virus, the WN wild-type strain NY99-35262 used in this study was kindly provided by Dr. R. Lanciotti (Centers for Disease Control and Prevention, Fort Collins, Colo.). It was originally isolated from a Chilean flamingo at the Bronx Zoo (New York) in 1999 (Lanciotti, R. S. et al. 1999 *Science* 286:2333-2337). The sequence of WN NY99 genome is available as GenBank accession number AF196835, per Table 1, and other strains of WN may substitute for the sequence of WN NY99 genome. A virus suspension prepared in Vero cells had a titer of $2.6 \times 10^7$ focus-forming units per milliliter (FFU/ml) as determined with Vero cells using an immunostaining focus-forming assay (Pletnev, A. G. 2001 *Virology* 282:288-300) and WN-specific mouse antibodies. Turning to dengue virus, wild-type DEN4 Caribbean strain 814669 (GenBank accession number AF326573) was used, which replicated in Vero cells with a titer of $1.1 \times 10^8$ FFU/ml. The sequence of recombinant DEN4 genome is available as GenBank accession number AF326825, per Table 1, and other strains of DEN4 may substitute for the sequence of DEN4 genome. The sequence of DEN1 genome is available as GenBank accession number U88536, the sequence of DEN2 genome is available as GenBank accession number M19197, and the sequence of DEN3 genome is available as GenBank accession number M93130, and any of these sequences may substitute for the sequence of DEN4 genome.

Chimeric WN/DEN4 cDNA and Recovery of Infectious Virus.

Plasmid p2A(XhoI) (Bray, M. & Lai, C.-J. 1991 *PNAS USA* 88:10342-10346) containing the DEN4 full-length infectious cDNA, previously employed for recovery of chimeric TBEV/DEN4 and LGT/DEN4 viruses (Pletnev, A. G. et at 1992 *PNAS USA* 89:10532-10536; Pletnev, A. G. & Men, R. 1998 *PNAS. USA* 95:1746-1751), was used for construction of WN/DEN4 cDNA. This was achieved by substituting cDNA of the WN prM and E protein genes for those of the corresponding DEN4 genes (FIG. 1B). The source of WN cDNA was a PCR product that included nucleotides (nts) 233 to 2758 of the WN strain NY99 genome. This was also kindly provided by Dr. R. Lanciotti (CDC). The nucleotide sequence of the structural protein genes in this PCR fragment was determined and compared with the published sequence of WN NY99 (GenBank accession number AF196835). Three nucleotide differences ($C_{1893} \rightarrow U$, $C_{2370} \rightarrow U$ and $C_{2385} \rightarrow A$) were identified in the E protein sequence, none of which resulted in an amino acid substitution.

Prior experience with construction and analysis of tick-borne/DEN4 chimeras indicated that we could not predict a priori the sequence of the DEN4 C protein/tick-borne flavivirus prM protein junction required for viability (Pletnev, A. G. et al. 1992 *PNAS USA* 89:10532-10536; Pletnev, A. G. & Men, R. 1998 *PNAS. USA* 95:1746-1751). For this reason, we adopted an empirical approach and tested several different C/prM junction sequences (FIG. 2). This was not necessary for the downstream junction because it was located within the COOH-terminal region of WN E. Initially, 3 sets of C/prM junctions were tested but only one yielded a viable WN/DEN4 chimera (FIG. 2). The primers employed for construction of the chimeras by PCR used oligonucleotide 5'-TCAAAACAAAAGAAAAGATCTGCAGTGACCG-GAATTGCAGTCATGATTGGC-3' (SEQ ID NO: 34), or 5'-TCAAAACAAAAGAAAAGATCTGCAGGGACCG-GAATTGCAGTCATGATTGGC-3' (SEQ ID NO: 35), or 5'-TCAAAACAAAAGAAAAGATCTGCAGACACCG-GAATTGCAGTCATGATTGGC-3' (SEQ ID NO: 36) as a forward primer and oligonucleotide 5'-CCG-CAAGAAACGTCATAGCAATTGACCTGTCACTC-GAGTTGATTCCCATCCACAA CAGAAGAGC-3' (SEQ ID NO: 37) as a reverse primer. Stable full-length WN/DEN4 cDNA clones were identified after transformation of *E. coli* BD 1528 with a ligation mixture that contained the PCR product and the vector both of which were digested by PstI and XhoI (FIG. 2). Sequences at the junctions between WN and DEN4 genes in each chimeric plasmid were verified.

Plasmid DNA containing full-length WN/DEN4 cDNA was linearized with Asp718. In vitro RNA synthesis and transfection of cells with its RNA transcripts were performed as described previously (Pletnev, A. G. 2001 *Virology* 282:288-300). Briefly, RNA transcripts of full-length WN/DEN4 constructs listed in FIG. 2 were used to transfect simian $LLCMK_2$, simian Vero cells or mosquito C6/36 cells in the presence of LipofectAmine 2000 reagent (GIBCO BRL, Gaithersburg, Md.) in a BSL-3 laboratory generously provided by Dr. L. Markoff (CBER, FDA). Transfected cells were examined by immunofluorescence assay (IFA) for the presence of WN or DEN4 proteins using a WN- or DEN4-specific hyperimmune mouse ascitic fluid (HMAF). Two infectious chimeric viruses containing WN/DEN4 group 4 junctions (FIG. 2), namely, WN/DEN4 clone 18 and 55, were isolated. The recovered chimeras were amplified once in simian Vero or mosquito C6/36 cells, viral RNA was isolated and then reverse transcribed into cDNA that was used for sequence analysis (Table 1). In a similar manner, the sequence of the Vero cell-derived WN/DEN4 clone 18 was determined after an additional purification by two rounds of terminal end-point dilution and amplification in Vero cells infected at a multiplicity of 0.01. The resulting virus suspension had a titer of $1.7 \times 10^6$ FFU/ml.

To introduce a deletion into the 3' untranslated region (UTR) of WN/DEN4 genome, the DNA fragment between the XhoI site (nt 2345 of DEN4 genome; GenBank accession number AF326827) and the Asp718 site at the 3' end of plasmid WN/DEN4-18 DNA was replaced by the corresponding XhoI-Asp718-fragment derived from full-length cDNA of a DEN4 mutant, clone p4Δ30 (Durbin et al. 2001 *Am. J Trop Med. Hyg* 65:405-413). This mutant had 30 nts deleted from the 3' untranslated region (UTR) of the genome between nts 10478-10507. Full-length RNA generated by SP6 polymerase from 10 different plasmids was tested for infectivity by transfection of simian Vero cells. Two individual WN/DEN4-3'Δ30 cDNA clones were infectious. The rescued deletion mutants, WN/DEN4-3'Δ30 clone 1 and 78, were purified twice by terminal end-point dilution and amplified in Vero cells to a titer of $1.4 \times 10^5$ and $6 \times 10^4$ FFU/ml, respectively. Viral RNA was isolated, and complete sequence of the 3' deletion mutant genome was determined (Table 1).

Evaluation of Parental and Chimeric Viruses in Mice

Neurovirulence of Vero cell culture-propagated parental WN (strain NY99), parental DEN4 (strain 814669), chimeric WN/DEN4 (clone 18) and its deletion mutant (clone 1) was evaluated in a BSL-3 facility. Three-day-old Swiss Webster mice (Taconic Farms) in groups of 9 to 12 were inoculated by the intracerebral (IC) route with decimal dilutions ranging from 0.1 to $10^5$ FFU of virus in 0.03 ml of MEM/0.25% human serum albumin. Mice were observed for 21 days for development of fatal encephalitis. The 50% lethal dose ($LD_{50}$) of each virus was determined by the method of Reed and Muench (Reed, L. J. & Muench, H. 1938 *Am. J Hyg* 27:493-497). Parental and chimeric viruses were also analyzed for peripheral virulence by intraperitoneal (IP) inoculation of 3-week-old Swiss female mice in groups of 10. Mice were inoculated with decimal dilutions of virus ranging from 0.1 to $10^5$ FFU and observed for 28 days for fatal encephalitis. Moribund mice were humanely euthanized.

Mice that survived IP inoculation were bled on day 28 to evaluate the WN-specific neutralizing antibody response. Serum from mice in each group was pooled and the WN virus-neutralizing antibody titer of the serum pool was determined by FFU reduction assay in Vero cells as described previously (Pletnev, A. G. et al. 2001 *J Viral* 75:8259-8267; Pletnev, A. G. 2001 *Virology* 282:288-300). Briefly, a 1:10 dilution of pooled sera was prepared in MEM containing 2% fetal bovine serum (FBS) and then heat inactivated for 30 min at 56° C. Serial twofold dilutions of inactivated pooled sera were mixed with an equal volume of a virus suspension containing approximately 50 FFU of WN. The mixture was incubated for 30 min at 37° C., and 0.4 ml was then added to duplicate wells of Vero cells in a 6-well plate. After 1 h of absorption at 37° C., the inoculum was removed and cells were overlaid with MEM containing 2% FBS, 50 µg/ml gentamycin, 0.25 µg/ml fungizone, and 1% tragacanth gum. Antibody titer was determined after 2 days of incubation by an immunostaining focus-forming assay (Pletnev, A. G. 2001 *Virology* 282:288-300) that used WN-specific HMAF. Neutralizing antibody titer was the highest dilution of pooled sera that reduced focus formation 50% compared to sera collected from non-immunized mice.

The surviving mice were challenged IP on day 29 with 100 IP $LD_{50}$ ($10^3$ FFU) of parental WN virus and observed for fatal encephalitis for a period of 21 days, Moribund mice were humanely euthanized.

Results.

Construction and Recovery of Chimeric WN/DEN4 Viruses

In total we constructed 18 plasmids that contained full-length chimeric WN/DEN4 cDNA which included the structural prM and E protein genes of the WN strain NY99 with all other sequences derived from DEN4 (FIG. 2). Full-length RNA generated by SP6 RNA polymerase from only 2 of the 18 chimeric cDNAs was infectious when transfected into mosquito C6/36 or simian Vero cells. Evidence for virus infectivity was detected by IFA. In the case of the 2 viable chimeric viruses, 80-100% of transfected cells were infected by day 5 as indicated by IFA using WN-specific HMAF. The 2 viable chimeric viruses (WN/DEN4 clones 18 and 55) had the C/prM intergenic junction sequence of group 4 chimera shown in FIG. 2, i.e., +3 Asp and +6 Thr amino acids downstream of the cleavage site, respectively. The presence of this junction was confirmed by sequence analysis of the recovered chimeras. Also, the complete genomic sequence of the two chimeras rescued from cDNA in Vero cells was determined and compared with the consensus sequence of their parental WN NY99 and DEN4 viruses as well as the nucleotide sequence of the WN/DEN4 viral chimera insert in the plasmid DNA from which infectious RNA transcripts were derived (Table 1). Analysis of plasmid DNAs revealed 4 differences in nucleotide sequence from the consensus WN sequence determined by RT-PCR of a high titered suspension of WN strain NY99. Three of these differences produced amino acid substitutions in prM (Ile$_6$→Thr and Ile$_{146}$→Val) and E (Thr$_{282}$→Ala). In addition, variability between (i) Glu$_{92}$ and Asp and (ii) Leu$_{112}$ and Ser was identified in the DEN4 NS3 and NS4B nonstructural proteins of the WN/DEN4 clone 55. Also, sequence of the Vero cell-grown WN/DEN4 clone 18 differed from its progenitor plasmid cDNA sequence in the DEN4 NS4B gene. A change U$_{7162}$→C that caused the substitution Leu$_{112}$→Ser was identified, which was observed previously (Blaney, J. E. et al. 2001 *J Virol* 75:9731-9740). Interestingly, a different substitution at this locus, Leu$_{112}$→Phe, was also previously observed by Blaney et al. upon passage of wild-type DEN4 in Vero cells.

Following our success in constructing full-length infectious WN/DEN4 cDNAs, we constructed chimeric virus mutants with a 30 nucleotide deletion in their 3' untranslated region (UTR). Two mutants, WN/DEN4-3'Δ30 clone 1 and clone 78, were recovered from transfected Vero cells. The complete sequence of both these clones was analyzed (Table 1). Sequence of clone 78 differed from the sequence of plasmid DNA from which its infectious RNA transcripts were derived. A change of C$_{7141}$→U produced an amino acid substitution Thr$_{105}$→Ile in the NS4B protein. The WN/DEN4-3'Δ30 clone 1 also exhibited only one nucleotide difference from the plasmid cDNA sequence. This resulted in the same NS4B amino acid change (Leu$_{112}$→Ser) that was observed in WN/DEN4 clone 18.

The WN/DEN4 chimera replicated more efficiently in Vero cells than did WN/DEN4-3'Δ30. The unmodified WN/DEN4 chimera reached a titer of 10$^6$ FFU/ml on day 6 in cells infected with a multiplicity of infection of 0.01; this was approximately 10-fold higher than the titer attained by the deletion mutant by day 6. The titer of the unmodified chimera was nearly the same as that attained by parental DEN4 under the same conditions.

Mouse Neurovirulence.

Before evaluating chimeric viruses for virulence in mice, the Vero cell-rescued chimeric WN/DEN4 virus and its 3' deletion mutant were cloned biologically twice by terminal end-point dilution and then amplified in qualified Vero cells. The titer attained by the Vero cell-adapted WN/DEN4 clone 18 and WN/DEN4-3'Δ30 clone 1 was 1.7×10$^6$ FFU/ml and 1.4×10$^5$ FFU/ml, respectively.

Both chimeric WN/DEN4 virus and the deletion mutant WN/DEN4-3'Δ30 as well as parental WN strain NY99 and DEN4 strain 814669 viruses were evaluated in 3-day-old Swiss mice for neurovirulence by direct IC inoculation (Table 2). Wild-type WN NY99 grown in Vero cells was highly neurovirulent with an intracerebral LD$_{50}$ of 0.35 FFU in suckling Swiss mice. Wild-type DEN4 also grown in Vero cells was less neurovirulent with an IC LD$_{50}$ of 407 FFU. Both WN/DEN4 and WN/DEN4-3'Δ30 chimeric viruses exhibited a significant reduction in neurovirulence compared to their WN and DEN4 parents. All of the mice inoculated IC with 10$^3$ FFU of WN/DEN4 or its 3' deletion mutant survived during a 21 day observation period. At a higher dose of 10$^4$ FFU, only 4 of 11 mice inoculated with WN/DEN4 died. Thus, in suckling mice the WN/DEN4 chimera was more than 28,571 times less neurovirulent than its WN parent. The chimera with the 30 nt deletion was also significantly less neurovirulent than its WN parent. These observations are consistent with earlier observations that chimerization of TBEV or LGT with DEN4 significantly reduced their neurovirulence for mice (Pletnev, A. G. et al. 1992 *PNAS USA* 89:10532-10536; Pletnev. A. G. & Men, R. 1998 *PNAS. USA* 95:1746-1751; Pletnev, A. G., Bray, M. & Lai, C.-J. 1993 *J Virol* 67:4956-4963).

Peripheral Virulence in Mice

Subsequently, we evaluated the chimeric viruses for peripheral virulence, i.e., the ability of virus inoculated by the IP route to spread from a peripheral site to the central nervous system and cause encephalitis. Both chimeras were highly attenuated compared to their WN parent (Table 2 and 3). Notably, IP inoculation of 10$^4$ FFU of the deletion mutant chimera or 10$^5$ FFU of the unmodified chimera did not induce fatal encephalitis in any of the 3-week-old Swiss mice, whereas the IP LD$_{50}$ for the WN parent was 10 FFU.

The chimeras were also evaluated in adult SCID mice because previous studies of tick-borne flaviviruses and their DEN4 chimeras indicated that SCID mice were a more sensitive detector of peripheral virulence than immunocompetent mice. Intraperitoneal inoculation of the maximum quantity of chimera, 10$^5$ FFU for WN/DEN4 and 10$^4$ FFU for WN/DEN4-3'Δ30, did not produce encephalitis in any instance (Table 2). In contrast, the IP LD$_{50}$ for parental WN was 6 FFU. These observations confirmed that the ablation of peripheral virulence of the WN chimeras had been achieved.

Immunogenicity and Protective Efficacy of Chimeric Viruses in Mice

The two chimeras were immunogenic; a single IP inoculation of 10$^2$ FFU of the WN/DEN4 chimera induced a moderate level of serum WN neutralizing antibodies (1:93), while a 10-fold higher concentration (10$^3$ FFU) induced a very high titer of WN neutralizing antibodies (1:1189) (Table 3). Also, 10$^3$ FFU of the chimeric WN/DEN4-3'Δ30 deletion mutant stimulated a high level of such antibodies (1:292). Intraperitoneal challenge of the immunized mice on day 29 with 100 IP LD$_{50}$ (10$^3$ FFU) of parental WN indicated that the chimeras provided 90 to 100% protection against this high dose WN challenge (Table 3). There was a good correlation between the titer of serum WN neutralizing antibodies that developed in response to immunization and the degree of resistance induced. All unvaccinated control mice developed signs of CNS disease 7 to 13 days after challenge with 100 IP LD$_{50}$ of WN and these animals died shortly thereafter. To determine whether there was an age-related resistance of mice to WN, another group of 7-week-old mice also served as controls; they were the same age as immunized mice at time of challenge. This group of older control mice was challenged with one IP LD$_{50}$, determined in 3-week-old mice. Seven of eight mice died during the 21 day observation period. This indicated that age-dependent resistance of mice to WN was not a factor in the observed protective effect of immunization.

TABLE 1

Mutations that were identified in genome of the WN/DEN4 or WN/DEN4-3'Δ30 chimera during cloning and rescue of chimera from cDNA in simian Vero cells

| Virus | Region of genome | NT (position)* | WN/DEN4 pDNA** | WN/DEN4 Recombinant virus clone 55 | WN/DEN4 Recombinant virus clone 18 | WN/DEN4-3' Δ30 pDNA⁺ | WN/DEN4-3' Δ30 Recombinant virus clone 1 | WN/DEN4-3' Δ30 Recombinant virus clone 78 | Amino acid change |
|---|---|---|---|---|---|---|---|---|---|
| WN | prM | $U_{428}$ | C | C | C | C | C | C | $Ile_6 \rightarrow Thr$ |
|  |  | $A_{847}$ | G | G | G | G | G | G | $Ile_{146} \rightarrow Val$ |
|  | E | $A_{1566}$ | G | G | G | G | G | G | silent |
|  |  | $A_{1810}$ | G | G | G | G | G | G | $Thr_{282} \rightarrow Ala$ |
| DEN4 | NS3 | $A_{4799}$ | A | C/a | A | A | A | A | $Glu_{92} \rightarrow Asp$ |
|  | NS4B | $C_{7141}$ | C | C | C | C | C | U | $Thr_{105} \rightarrow Ile$ |
|  |  | $U_{7162}$ | U | C/u | C | U | C | U | $Leu_{112} \rightarrow Ser$ |

*Numbering of nucleotide sequence of structural protein genes derived from the sequence of WN NY99 genome (GenBank accession number AF196835) and numbering of nucleotide sequence of nonstructural protein genes derived from the sequence of DEN4 genome (GenBank accession number AF326825).
**Plasmid DNA.
⁺Comparison of the pDNA for the parental cDNA clones used to derive the chimeric viruses are indicated in Durbin, A. et al. 2001 *Am J Trop Med Hyg* 65: 405-413

TABLE 2

Neurovirulence and peripheral virulence of parental West Nile virus (WN) or Dengue type 4 virus (DEN4) and their chimeric WN/DEN4 virus or its 3' deletion mutant WN/DEN4-3'Δ30 in mice as assayed by intracerebral (IC) or intraperitoneal (IP) inoculation

| Virus | Neurovirulence: $LD_{50}$ (FFU) after IC inoculation of 3-day-old Swiss mice | Neurovirulence: Reduction from WN parent | Peripheral virulence: $LD_{50}$ (FFU) after IP inoculation of 3-week-old Swiss mice | Peripheral virulence: $LD_{50}$ (FFU) after IP inoculation of 3-week-old SCID mice | Reduction from WN parent |
|---|---|---|---|---|---|
| DEN4 | 407 | — | >100,000* | >100,000* | — |
| WN | 0.35 | — | 10 | 6.0 | — |
| WN/DEN4 Chimera (clone 18) | >10,000* | >28,571x | >100,000* | >100,000* | >10,000x |
| WN/DEN4-3'Δ30 Chimera (clone 1) | >1,000* | >2,857x | >10,000* | >10,000* | >1,000x |

Note:
Each decimal dilution was tested in 9 to 12 mice in group.
*Highest concentration tested.

TABLE 3

Peripheral virulence, antibody response and protective efficacy of parental (WN or DEN4) viruses and chimeric WN/DEN4 virus or its 3' deletion mutant WN/DEN4-3'Δ30 in 3-week-old Swiss mice

| Mice inoculated IP with | Dose (FFC*) inoculated | Mortality after IP inoculation | Mean titer of WN neutralizing antibody in pooled sera on day 28 | Mortality after survivors inoculated IP with 100 IP $LD_{50}$ of WN on day 29 |
|---|---|---|---|---|
| WN | 0.1 | 0/10 | <1:10 | 10/10 (100%) |
|  | 1 | 0/10 | 1:24 | 10/10 (100%) |
|  | 10 | 5/10 | 1:40 | 4/5 (80%) |
|  | 100 | 10/10 |  |  |
|  | 1,000 | 9/10 |  |  |
|  | 10,000 | 10/10 |  |  |
| WN/DEN4 Chimera (clone 18) | 1 | 0/10 | 1:26 | 10/10 (100%) |
|  | 10 | 0/10 | 1:21 | 9/10 (90%) |
|  | 100 | 0/10 | 1:93 | 7/10 (70%) |
|  | 1,000 | 0/10 | 1:1189 | 0/10 (0%) |
|  | 10,000 | 0/10 | 1:585 | 0/9** (0%) |
|  | 100,000 | 0/10 | 1:924 | 0/10 (0%) |
| WN/DEN4-3'Δ30 Chimera (clone 1) | 1 | 0/10 | 1:28 | 9/10 (90%) |
|  | 10 | 0/10 | <1:10 | 9/10 (90%) |
|  | 100 | 0/10 | 1:14 | 8/10 (80%) |

TABLE 3-continued

Peripheral virulence, antibody response and protective efficacy of parental (WN or DEN4) viruses and chimeric WN/DEN4 virus or its 3' deletion mutant WN/DEN4-3'Δ30 in 3-week-old Swiss mice

| Mice inoculated IP with | Dose (FFC*) inoculated | Mortality after IP inoculation | Mean titer of WN neutralizing antibody in pooled sera on day 28 | Mortality after survivors inoculated IP with 100 IP $LD_{50}$ of WN on day 29 |
|---|---|---|---|---|
| | 1,000 | 0/10 | 1:292 | 1/10 (10%) |
| | 10,000 | 0/10 | 1:269 | 0/10 (0%) |
| DEN4 | 1,000 | 0/10 | <1:10 | 10/10 (100%) |
| | 10,000 | 0/10 | 1:13 | 8/10 (80%) |
| | 100,000 | 0/10 | 1:22 | 10/10 (100%) |
| Control | | | <1:10 | 10/10 (100%) |

*Focus forming unit.
**One of the 10 mice inoculated died as a result of trauma; WN virus was not detected in the brain by tissue culture (Vero cell) assay.

TABLE 4

Chimeric WN/DEN4 and its 3' deletion mutant WN/DEN4-3'Δ30 are attenuated in rhesus monkeys

| | | | Viremia | | |
|---|---|---|---|---|---|
| Virus inoculated subcutaneously | Dose of virus (FFU) | No. of monkeys inoculated | No. viremic | Mean duration (days) | Mean peak titer of viremia during 2 weeks post-inoculation $log_{10}$ (FFU/ml)* |
| WN/DEN4 | $10^5$ | 4 | 3 | 1.5 | 0.78 |
| | $10^6$ | 4 | 2 | 0.5 | <0.7 |
| WN/DEN4-3'Δ30 | $10^5$ | 4 | 0 | 0 | <0.7 |
| WN | $10^5$ | 2 | 2 | 5.5 | 2.63 |
| | $10^6$ | 2 | 2 | 5.5 | 2.76 |
| DEN4 | $10^6$ | 4 | 4 | 3.8 | 2.23 |

*Tested daily for 10 days.

Note:

0.7 $log_{10}$ (FFU/ml) is a lowest level of detectable viremia in serum.

0.6 log10 (FFU/ml) was used to calculate mean peak titer of viremia for animals that had no detectable viremia.

TABLE 5

Immunogenicity and protective efficacy of chimeric WN/DEN4 and its 3' deletion mutant WN/DEN4-3'Δ30 in rhesus monkeys

| Group of monkeys inculated SC with | | | | |
|---|---|---|---|---|
| Virus | Dose (FFU) | No. of monkeys | Geo. mean titer of WN serum neutralizing antibody on post immunization day 42 (range) | No. of monkeys viremic during 2 weeks post challenge with $10^5$ FFU of WN (Mean peak titer; $log_{10}$ FFU/ml)* |
| WN/DEN4 | $10^5$ | 4 | 1:661 (416-1126) | 0 |
| | $10^6$ | 4 | 1:501 (270-727) | 0 |
| WN/DEN4-3'Δ30 | $10^5$ | 4 | 1:186 (109-247) | 0 |
| WN | $10^5$ | 2 | 1:1318 (1305-1324) | 0 |
| | $10^6$ | 2 | 1:708 (599-842) | 0 |
| DEN4 | $10^6$ | 4 | <1:20 | 4 (2.04**) |

*Tested daily for 10 days.

**Mean duration of viremia was 3.75 days.

Attenuation, Immunogenicity and Protective Efficacy of West Nile/DEN4 Chimeras in Rhesus Monkeys It has been established that some non-human primates are readily infected with a number of flaviviruses by the peripheral route (Simmons et al. 1931 *Philipp J Sci* 44:1-247; Rosen, 1958 *Am J Trop Med Hyg* 7:406-410). Thus, infection of monkeys represents the closest experimental system to flavivirus infection of humans. The response of monkeys to flavivirus infection is similar to that of humans in that there is a four to six day viremia, although lower primates do not usually develop clinical flavivirus symptoms. The objectives of flavivirus studies in monkeys are: (1) to evaluate the immunogenicity of various candidate vaccines; (2) to evaluate the infectivity and virulence (attenuation phenotype) of candidate vaccines as measured by the duration of viremia in days and the peak virus titer in FFU/ml; and (3) to evaluate the protective efficacy of the candidate vaccines against challenge by wild-type flavivirus.

1) Inoculation: Each monkey is inoculated with a total of $10^5$ or $10^6$ FFU of virus diluted in L15 medium with SPG (Durbin, A. P. et al. 2001 *Am J Trop Med Hyg* 65:405-413). Normally, virus is inoculated by the subcutaneous route to anesthetized animals.

2) Blood collection: Following inoculation of virus, blood samples of 3.0 ml are taken daily for two weeks and 5.0 ml at 3 weeks, 4 weeks, 5 weeks, and 6 weeks.

3) Challenge with parental wild-type flavivirus: Where virus challenge is deemed appropriate to evaluate the protective efficacy, monkeys are inoculated with wild-type virus at $10^5$ FFU/dose in a 1.0 ml volume subcutaneously in the upper arm area.

4) Laboratory assays: Serum samples are collected to be used to determine: (a) the duration and level of viremia by direct viral plaque or FFU assay; and (b) the titer of neutralizing antibodies induced as measured by FFU reduction neutralization test, all tests well known to those skilled in the art of vaccine development.

Attenuation, immunogenicity, and protective efficacy of the West Nile/DEN4 chimeras were studied in 20 rhesus monkeys (Tables 4 and 5). Eight monkeys were inoculated subcutaneously (SC) with WN/DEN4 (clone 18); 4 animals received $10^5$ FFU, while the other 4 received $10^6$ FFU. Four monkeys were inoculated SC with $10^5$ FFU of WN/DEN4-3'Δ30 (clone 1). A group of 4 monkeys was inoculated SC with parental West Nile virus; 2 animals received $10^5$ FFU, while the other received $10^6$ FFU. Finally, another group of 4 monkeys was inoculated SC with $10^6$ of DEN4 (Table 4).

Each of the monkeys inoculated SC with $10^5$ or $10^6$ FFU of West Nile virus developed a viremia that lasted 5 to 6 days and attained a mean peak titer of 2.6 to 2.8 $\log_{10}$ (FFU/ml) (FIG. 3, Table 4). In contrast, WN/DEN4 induced viremia in only 5 of the 8 monkeys inoculated with $10^5$ or $10^6$ FFU. Viremia lasted only one to two days and attained a peak titer 100 fold lower than observed for WN infected monkeys. Significantly, each of the 4 monkeys inoculated SC with $10^5$ FFU of the WN/DEN4-3'Δ30 mutant failed to develop a detectable viremia.

Although the WN/DEN chimera and its deletion mutant were significantly attenuated for rhesus monkeys, these hybrid viruses induced a moderate to high level of serum WN neutralizing antibodies in each immunized animal (Table 5). The two chimeras also induced complete resistance to SC challenge with $10^5$ FFU of West Nile virus on day 42 post immunization. Viremia of WN was not detected in any of the 12 monkeys immunized with WN/DEN4 or its deletion mutant. The West Nile challenge virus replicated efficiently in monkeys previously infected with DEN4 virus. This indicates that the high level of protection against WN challenge afforded by infection with WN/DEN4 chimeric viruses is specified by the WN protective antigens in the chimera and not by the DEN4 component of the chimera.

The Δ30 mutation was first described and characterized in the DEN4 virus (Men, R. et al. 1996 *J Virol* 70:3930-7). In DEN4, the mutation consists of the removal of 30 contiguous nucleotides comprising nucleotides 10478-10507 of the 3' UTR (FIG. 4A) which form a putative stem-loop structure referred to as TL2 (Proutski, V. et al. 1997 *Nucleic Acids Res* 25:1194-202). Among the flaviviruses, large portions of the UTR form highly conserved secondary structures (Hahn, C. S., et al. 1987 *J Mol Biol* 198:33-41; Proutski, V. et al. 1997 *Nucleic Acids Res* 25:1194-202). Although the individual nucleotides are not necessarily conserved in these regions, appropriate base pairing preserves the stem-loop structure in each serotype, a fact that is not readily apparent when only considering the primary sequence (FIG. 4B, C). We have demonstrated that the Δ30 mutation specifies an attenuation phenotype that is transportable to other DEN serotypes, DEN1 (Whitehead, S. S. et al. 2003 *J Virol* 77:1653-1657) and DEN2 (Tonga/74) (U.S. Provisional Application, filed Dec. 23, 2002, as NIH1230.002PR). This indicates that the Δ30 mutation is expected to have a corresponding effect on DEN3 wild-type virus. We envision constructing this remaining virus by deletion of the TL2 region of the virus, e.g., DEN3 (Sleman/78) (FIG. 4C). These attenuated or wild type DEN1, DEN2, or DEN3 viruses could readily replace the DEN4 wild type or DEN4-3'Δ30 viruses presented in these examples.

These findings specifically identify two candidate WN live attenuated virus vaccines. The first, WN/DEN4, is about 100-fold attenuated in comparison to WN wild-type virus as indicated by the greatly restricted level of viremia. The second virus, WN/DEN4-3'Δ30, is more attenuated than WN/DEN4 as indicated by the absence of viremia in monkey serum and by the moderately decreased serum neutralizing antibody response. Thus, the methods and viruses taught provide live attenuated WN vaccines of differing levels of attenuation, each of which is highly protective against wild-type WN virus challenge. Similar attenuated WN/DEN chimeric viruses on a DEN1, DEN2, or DEN3 background are envisioned.

Further Attenuation of WN/DEN4 Chimeras by Introduction of Additional Mutations in the Genes for the Non-Structural Proteins of DEN4 that Serve as a Component of These Vaccine Candidates We contemplate achieving an increase in the level of attenuation of the candidate vaccine WN/DEN4 or WN/DEN4-3'Δ30 chimera if need be by adding one or more attenuation mutations to the DEN4 component of the chimeras. A large set of mutations that attenuate DEN4 in mice (Blaney, et al. 2001 *J Virol* 75:9731-9740; Blaney, et al. 2002 *Virology* 300:125-139; Hanley, et al. 2002 *J Virol* 76:525-31) has been identified in the part of the DEN4 genome included in the WN/DEN4 chimeric viruses. Members from this set of attenuating mutations can be introduced in the WN/DEN4 chimeric virus to further attenuate these viruses. For example, it might be necessary to further attenuate the WN/DEN4 virus, which possesses some residual neurovirulence as indicated above. The feasibility of this approach to achieve further attenuation is exemplified by introducing a viable mutation that specifies a temperature sensitive phenotype as well as a phenotype of growth restriction in suckling mouse brain into the non-structural protein 3 (NS3) of the DEN4 component of the WN/DEN4 chimera. Mutation 4891 (isoleucine→threonine) had previously been identified at nucleotide 4891 of the NS3 gene of DEN4 (Blaney, et al. 2002 *Virology* 300:125-139). Mutation 4891 specified two desirable phenotypes, i.e., temperature sensitivity and growth restriction in brain tissue. Similarly, mutation 4995 (serine→proline), also in NS3, specified the same two desirable phenotypes (Blaney, et al. 2001 *J Virology* 75:9731-9740, 2001). The 4891 and 4995 mutations also increase replication fitness of DEN4 in Vero cells, i.e., they are Vero cell adaptation mutations. The wild type amino acid residue at DEN4 4891 (isoleucine) is conserved in DEN2 Tonga/74 and DEN3 Sleman/78, but not DEN1 West Pacific. The wild type amino acid residue at DEN4 4995 (serine) is conserved in DEN1 West Pacific, DEN2 Tonga/74, but not DEN3 Sleman. One or both of these mutations may also be included in a WN/DEN1, 2, or 3 chimera. Thus, their inclusion in WN/DEN4 virus is contemplated as achieving an increase in replication of the virus in Vero cells or the genetic stability of the mutation during manufacture in Vero cells.

Discussion.

Initially, we demonstrated that although prM and E proteins of distantly related tick-borne and mosquito-borne flaviviruses are highly divergent, these proteins could be interchanged in some instances without loss of virus viability (Pletnev, A. G. et al. 1992 *PNAS USA* 89:10532-10536; Pletnev, A. G. & Men, R. 1998 *PNAS USA* 95:1746-1751). This approach has been used to create new chimeric flaviviruses (Bray, M., Men, R. & Lai, C.-J. 1996 *J. Virol.* 70:4162-4166; Chambers, T. J. et al. 1999 *J Virol* 73:3095-3101; Guirakhoo, F. et al. 2000 *J Virol* 74:5477-5485; Huang, C. Y. et al. 2000 *J Virol* 74:3020-3028; Van Der Most, R. G. et al. 2000 *J Virol* 74:8094-8101; Caufour, P. S. et al. 2001 *Virus Res* 79:1-14).

Previously, we succeeded in constructing and recovering viable tick-borne/DEN4 chimeras (Pletnev, A. G. et al. 1992 *PNAS USA* 89:10532-10536; Pletnev, A. G. & Men, R. 1998 *PNAS USA* 95:1746-1751; Pletnev, A. G., Bray, M. & Lai, C.-J. 1993 *J Virol* 67:4956-4963). In these instances, the tick-borne flavivirus parent was tick-borne encephalitis virus, a highly virulent virus, or Langat virus, a naturally attenuated tick-borne virus. Thus, the two components of these chimeras had disparate vector hosts, namely ticks and in the case of DEN4, mosquitoes. Decreased efficiency of gene product interactions in the chimeras was thought to be the basis for the marked attenuation exhibited by these hybrid viruses. Nonetheless, although highly attenuated in mice, the TBEV/DEN4 and LGT/DEN4 chimeras were immunogenic and provided considerable protection against their parental tick-borne flavivirus. In the present instance, both virus parents of the WN/DEN4 chimeras are transmitted by mosquitoes. However, vector preference differs, Aedes for DEN4 and Culex for WN (Burke, D. S. & Monath, T. P. 2001 in *Fields Virology*, eds. Knipe, D. M. & Howley, P. M. Lippincott Williams and Wilkins, Philadelphia, 4-th ed., pp. 1043-1125; Hayes, C. G. 1989 in *The Arboviruses: Epidemiology and Ecology*, ed. Monath T. P. Boca Raton, Fla.: CRC Press, Volume V, pp. 59-88).

Figure 1A:
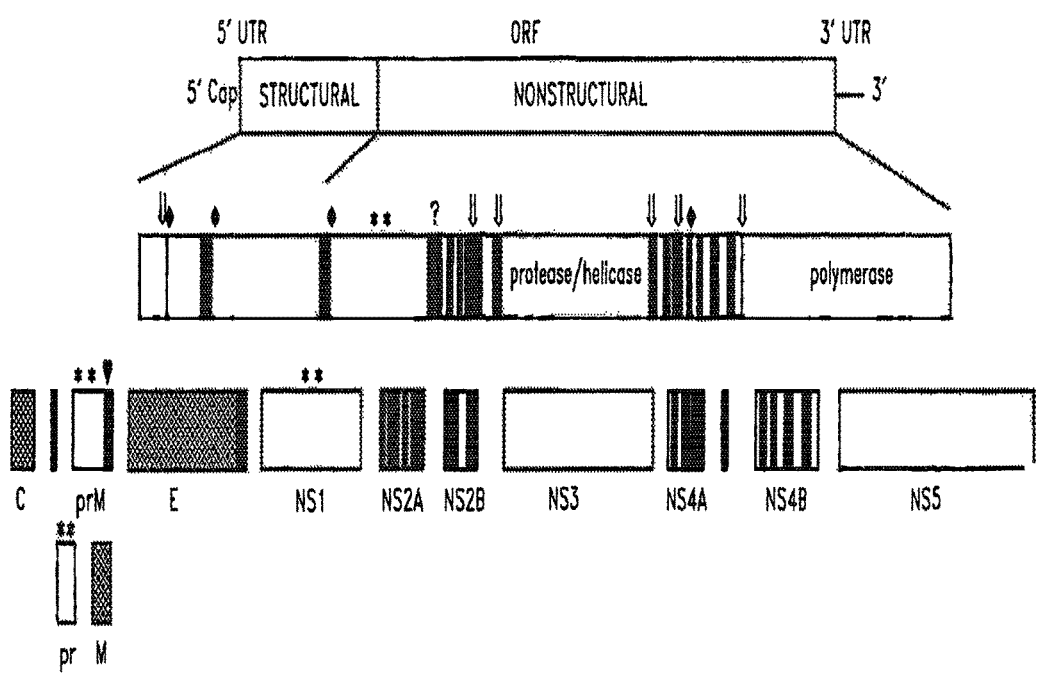
FIG. 1A shows the translation and processing of the flavivirus polyprotein. At the top is depicted the viral genome with the structural and nonstructural protein coding regions, the 5' cap, and the 5' and 3' untranslated regions (UTRs) indicated. Boxes below the genome indicate precursors and mature proteins generated by the proteolytic processing cascade. Mature structural proteins are indicated by shaded boxes and the nonstructural proteins and structural protein precursors by open boxes. Contiguous stretches of uncharged amino acids are shown by black bars. Asterisks denote proteins with N-linked glycans but do not necessarily indicate the position or number of sites utilized. Cleavage sites for host signalase (♦), the viral serine protease (⇓), furin or other Golgi-localized protease (♥), or unknown proteases (?) are indicated. Taken from Field's Virology, 2001 Fourth Edition, B. D. Lindenbach and C. M. Rice, page 998, Chapter 32.

In the present study, we constructed viable WN/DEN4 chimeras that contained a DEN4 genome whose genes for structural prM and E proteins were replaced by the corresponding genes of WN strain NY99. Among flaviviruses, the hydrophobic domain between C and prM ("transmembrane signal domain") varies in sequence and also varies in length from 14 to 20 amino acids (Stocks, C. E. & Lobigs, M. 1998 *J Virol* 72:2141-2149). It acts as a signal sequence for translocation of prM protein into the endoplasmic reticulum lumen where post-translation maturation of this protein occurs (Lindenbach, B. D. & Rice, C. M. 2001 in *Fields Virology*, eds. Knipe, D. M. & Howley, P. M. Lippincott Williams and Wilkins, Philadelphia, 4-th ed., pp. 1043-1125). This signal peptide is flanked at its $NH_2$-terminal region by the viral protease NS2B-NS3 cleavage site and at its COOH-terminal region by a cellular signalase cleavage site. Four different junctions at the protease cleavage site between DEN4 C and WN prM protein were introduced separately in chimeric constructs (FIG. 2). The C/prM fusion sequence at the viral protease cleavage site (KR↓S) in the chimeras was constructed to be similar to that of the DEN4 parent, which provides its NS2B-NS3 protease for the processing of the chimeric polyprotein. However, each of the chimeric constructs of group 1 and 2 chimeras contain a unique substitution in the transmembrane signal sequence at the third amino acid position downstream of the protease cleavage site, while another sequence is shared by group 3 and group 4 chimeras (FIG. 1A, FIG. 2). Thus, the transmembrane signal of the constructs is similar in length but exhibits polymorphism for group 1, group 2 and groups 3 and 4 together. This occurs at the third amino acid position downstream of the protease cleavage site. Viable WN/DEN4 virus was recovered only when construct number 4 (FIG. 2) was employed to prepare RNA transcripts for transfection. Infectious virus was recovered from 2 of 5 separate clones that encoded Asp in the 3+ amino acid position. And only the 2 clones that also contained a second-site mutation at the 6+ amino acid position downstream of the protease cleavage site that substituted Thr for Ile were infectious; this mutation occurred during cloning of cDNA in bacteria (FIG. 2, Table 1). In contrast, none of the 13 clones that encoded Gly or Val at the 3+ amino acid position produced infectious virus following transfection. This suggests that the transmembrane signal sequence between C and prM is a determinant of viability in the context of a WN/DEN4 chimera. This is consistent with an earlier observation made with yellow fever virus that the transmembrane signal sequence between C and prM protein plays a role in viability and neurovirulence (Lee, E. et al. 2000 *J. Virol,* 74:24-32).

The +3 and +6 Asp and Thr motif at the capsid protein-preM protein cleavage site that was required for viability of the chimera could not be predicted from the sequence of either parent, i.e., DEN4 and West Nile virus, because neither parent had this +3 and +6 motif. Success was achieved by testing a number of disparate sequences at the cleavage site and this led to the identification of the +3 and +6 Asp and Thr motif that was required for viability. For this reason, we advocate an empirical approach that embraces testing several different C/prM junction sequences for identification of other motifs that produce equally viable chimeric virus.

The WN strain NY99 exhibited considerable virulence in Swiss mice; its IC $LD_{50}$ was 0.35 FFU for suckling mice and its IP $LD_{50}$ was 10 FFU for 3-week-old Swiss mice (Table 2). Nearly the same level of neurovirulence was observed for a wild-type strain of WN isolated in Israel that was evaluated in CD-1 (ICR) mice: IC $LD_{50}$ and IP $LD_{50}$ were estimated to be 1.1 and 4.3 PFU, respectively (Halevy, M. et al. 1994 *Arch Virol* 137:355-370). In addition, a high degree of genomic similarity (>99.8%) between the WN NY99 and the WN Israel-1998 was recently confirmed by sequence analysis (Lanciotti, R. S. et al. 1999 *Science* 286:2333-2337) indicating that both highly pathogenic strains of WN, representing North American and Middle Eastern viruses, are closely related. Wild-type DEN4 Caribbean strain 814669 was moderately neurovirulent for suckling mice with an IC $LD_{50}$ of 407 FFU, and it was approximately 20 times more virulent than its cDNA cloned virus (Pletnev, A. G. & Men, R. 1998 *PNAS USA* 95:1746-1751). In contrast, the WN/DEN4 chimera and its 3' deletion mutant were significantly less neurovirulent than their wild-type DEN4 or WN parent. Only at a high dose of $10^4$ FFU did a minority of mice, inoculated IC with WN/DEN4 chimera, die. Also, the WN/DEN4 chimera inoculated IC at this dose caused death of suckling mice later than parental WN virus: 4-5 days post-infection for wild-type WN compared to 9-13 days post-infection for the chimera. Additional methods and procedures are taught that allow further attenuation of the IC virulence of the WN/DEN4 chimeric virus by the introduction of mutations that are known to attenuate DEN4 virus for the brain of mice. In addition, we also contemplate achieving further attenuation of WN/DEN4-3'Δ30 by the incorporation of additional attenuating mutations.

Despite the high peripheral virulence of wild-type WN strain NY99 (IP $LD_{50}$ of 10 FFU), chimerization of WN with DEN4 completely ablated this property of its WN parent.

Thus, 3-week-old Swiss mice survived IP inoculation of $10^4$ or $10^5$ FFU of chimeric virus. Our observations are consistent with earlier findings that a similar large reduction of peripheral neurovirulence of TBEV or LGT occurs following chimerization with DEN4 (Pletnev, A. G. et al. 1992 *PNAS USA* 89:10532-10536; Pletnev, A. G. & Men, R. 1998 *PNAS. USA* 95:1746-1751; Pletnev, A. G., Bray, M. & Lai, C.-J. 1993 *J Virol* 67:4956-4963). Similar observations were made when the WN/DEN4 chimeras were tested in SCID mice for peripheral virulence (Table 2).

Although highly attenuated, the WN/DEN4 chimeras stimulated a moderate to high level of serum neutralizing antibodies against WN NY99 (Table 3). There was a strong correlation between the level of neutralizing antibodies to WN induced by immunization and resistance to subsequent lethal WN challenge. The immune response of mice inoculated with the chimeras was dose-dependent and indicated that the unmodified WN/DEN4 chimera was slightly more immunogenic than the corresponding 3' deletion mutant. However, 90 to 100% protection against WN challenge was achieved when a single $10^3$ FFU dose of WN/DEN4 chimera or its 3' deletion mutant was used for immunization. A higher dose ($10^4$ FFU) of either chimera provided complete protection to WN challenge. The WN/DEN4 and WN/DEN4-3'Δ30 were also highly attenuated, immunogenic, and protective against WN virus challenge in non-human primates (rhesus monkeys). Thus, the WN prM and E proteins of the chimeric viruses represent effective antigens able to induce complete protection to challenge with highly virulent WN in both mice and monkeys. Our observations concerning safety, immunogenicity, and protective efficacy of the chimeric WN/DEN4 vaccine candidates in mice and monkeys provide a basis for extending our evaluation of the vaccine candidates to humans and to domestic animals, such as horses or birds, which are at high risk. In this way, the use of the WN/DEN4 chimeras as vaccines is envisioned for humans and domestic animals, such as horses or birds.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

SEQUENCE LISTING

<160> NUMBER OF SEQ ID NOS: 37

<210> SEQ ID NO 1
<211> LENGTH: 10
<212> TYPE: PRT
<213> ORGANISM: West Nile virus

<400> SEQUENCE: 1

Lys Lys Arg Gly Gly Arg Thr Gly Ile Ala
1               5                   10

<210> SEQ ID NO 2
<211> LENGTH: 30
<212> TYPE: DNA
<213> ORGANISM: West Nile virus

<400> SEQUENCE: 2
aagaaaagag gaggaaagac cggaattgca                                      30

<210> SEQ ID NO 3
<211> LENGTH: 10
<212> TYPE: PRT
<213> ORGANISM: Dengue virus type 4

<400> SEQUENCE: 3

Arg Lys Arg Ser Thr Ile Thr Leu Leu Cys
1               5                   10

<210> SEQ ID NO 4
<211> LENGTH: 30
<212> TYPE: DNA
<213> ORGANISM: Dengue virus type 4

<400> SEQUENCE: 4 agaaaaggt caacgataac attgctgtgc                                       30

<210> SEQ ID NO 5
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 5

Arg Lys Arg Ser Ala Val Thr Gly Ile Ala
1               5                   10

<210> SEQ ID NO 6
<211> LENGTH: 30
<212> TYPE: DNA
<213> ORGANISM: Artificial Sequence
<220> FEATURE:
<223> OTHER INFORMATION: West Nile/Dengue 4 virus chimera

<400> SEQUENCE: 6
agaaaaaggt ctgcagtgac cggaattgca                                       30

<210> SEQ ID NO 7
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 7

Arg Lys Arg Ser Ala Gly Thr Gly Ile Ala
1               5                   10

<210> SEQ ID NO 8
<211> LENGTH: 30
<212> TYPE: DNA
<213> ORGANISM: Artificial Sequence
<220> FEATURE:
<223> OTHER INFORMATION: West Nile/Dengue 4 virus chimera

<400> SEQUENCE: 8
agaaaaaggt ctgcagggac cggaattgca                                       30

<210> SEQ ID NO 9
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 9

Arg Lys Arg Ser Ala Asp Thr Gly Ile Ala
1               5                   10

<210> SEQ ID NO 10
<211> LENGTH: 30
<212> TYPE: DNA
<213> ORGANISM: Artificial Sequence
<220> FEATURE:
<223> OTHER INFORMATION: West Nile/Dengue 4 virus chimera

<400> SEQUENCE: 10
agaaaaaggt ctgcagacac cggaattgca                                       30

<210> SEQ ID NO 11
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 11

Arg Lys Arg Ser Ala Asp Thr Gly Thr Ala

<210> SEQ ID NO 12
<211> LENGTH: 30
<212> TYPE: DNA
<213> ORGANISM: Artificial Sequence
<220> FEATURE:
<223> OTHER INFORMATION: West Nile/Dengue4 chimera

<400> SEQUENCE: 12
agaaaaaggt ctgcagacac cggaactgca                                     30

<210> SEQ ID NO 13
<211> LENGTH: 5
<212> TYPE: PRT
<213> ORGANISM: West Nile virus

<400> SEQUENCE: 13

Ile Asn Ala Arg Asp
1               5

<210> SEQ ID NO 14
<211> LENGTH: 15
<212> TYPE: DNA
<213> ORGANISM: West Nile virus

<400> SEQUENCE: 14
atcaatgctc gtgat                                                     15

<210> SEQ ID NO 15
<211> LENGTH: 5
<212> TYPE: PRT
<213> ORGANISM: Dengue virus type 4

<400> SEQUENCE: 15

Leu Asn Ser Arg Asn
1               5

<210> SEQ ID NO 16
<211> LENGTH: 15
<212> TYPE: DNA
<213> ORGANISM: Dengue virus type 4

<400> SEQUENCE: 16
ctgaactcga ggaac                                                     15

<210> SEQ ID NO 17
<211> LENGTH: 5
<212> TYPE: PRT
<213> ORGANISM: Artificial Sequence
<220> FEATURE:
<223> OTHER INFORMATION: West Nile/Dengue 4 virus chimera

<400> SEQUENCE: 17

Ile Asn Ser Arg Asn
1               5

<210> SEQ ID NO 18
<211> LENGTH: 15
<212> TYPE: DNA
<213> ORGANISM: Artificial Sequence
<220> FEATURE:
<223> OTHER INFORMATION: West Nile/Dengue 4 virus chimera

<400> SEQUENCE: 18
atcaactcga ggaac                                                        15

<210> SEQ ID NO 19
<211> LENGTH: 51
<212> TYPE: RNA
<213> ORGANISM: Dengue virus type 4

<400> SEQUENCE: 19
ggcccgaagc caggaggaag cuguacuccu gguggaagga cuagagguua g                51

<210> SEQ ID NO 20
<211> LENGTH: 47
<212> TYPE: RNA
<213> ORGANISM: Dengue virus type 4

<400> SEQUENCE: 20
ggggcccgaa gccaggagga agcuguacuc cugguggaag gacuaga                    47

<210> SEQ ID NO 21
<211> LENGTH: 16
<212> TYPE: RNA
<213> ORGANISM: Artificial Sequence
<220> FEATURE:
<223> OTHER INFORMATION: Dengue4 delta 30

<400> SEQUENCE: 21
ggggcccaag acuaga                                                      16

<210> SEQ ID NO 22
<211> LENGTH: 46
<212> TYPE: RNA
<213> ORGANISM: Dengue virus type 1

<400> SEQUENCE: 22
ggggcccaac caggggaa gcuguacccu ggugguaagg acuaga                       46

<210> SEQ ID NO 23
<211> LENGTH: 16
<212> TYPE: RNA
<213> ORGANISM: Artificial Sequence
<220> FEATURE:
<223> OTHER INFORMATION: Dengue1 delta 30

<400> SEQUENCE: 23
ggggcccaag acuaga                                                      16

<210> SEQ ID NO 24
<211> LENGTH: 46
<212> TYPE: RNA
<213> ORGANISM: Dengue virus type 2

<400> SEQUENCE: 24
ggggcccaag gugagaugaa gcuguagucu cacuggaagg acuaga                     46

<210> SEQ ID NO 25
<211> LENGTH: 47
<212> TYPE: RNA
<213> ORGANISM: Dengue virus type 3

<400> SEQUENCE: 25
ggggcccgag cucugaggga agcuguaccu ccuugcaaag gacuaga                    47

<210> SEQ ID NO 26
<211> LENGTH: 82

```
<212> TYPE: RNA
<213> ORGANISM: Dengue virus type 1

<400> SEQUENCE: 26
gcagcagcgg ggcccaacac caggggaagc uguacccugg ugguaaggac uagagguuag 60
aggagacccc ccgcaacaac aa 82

<210> SEQ ID NO 27
<211> LENGTH: 83
<212> TYPE: RNA
<213> ORGANISM: Dengue virus type 4

<400> SEQUENCE: 27
agcaaaaggg ggcccgaagc caggaggaag cuguacuccu gguggaagga cuagagguua 60
gaggagaccc ccccaacaca aaa 83

<210> SEQ ID NO 28
<211> LENGTH: 84
<212> TYPE: RNA
<213> ORGANISM: Dengue virus type 2

<400> SEQUENCE: 28
agcaacaaug gggggcccaag gugagaugaa gcuguagucu cacuggaagg acuagagguu 60
agaggagacc cccccaaaac aaaa 84

<210> SEQ ID NO 29
<211> LENGTH: 83
<212> TYPE: RNA
<213> ORGANISM: Dengue virus type 3

<400> SEQUENCE: 29
gcagcagcgg ggcccgagcu cugagggaag cuguaccucc uugcaaagga cuagagguua 60
gaggagaccc cccgcaaaua aaa 83

<210> SEQ ID NO 30
<211> LENGTH: 15159
<212> TYPE: DNA
<213> ORGANISM: Artificial Sequence
<220> FEATURE:
<223> OTHER INFORMATION: Dengue2 (Tonga/74) plasmid p2

<400> SEQUENCE: 30
agttgttagt ctacgtggac cgacaaagac agattctttg agggagctaa gctcaacgta 60
gttctaactg tttttgatt agagagcaga tctctgatga ataaccaacg gaaaaaggcg 120
agaaacacgc ctttcaatat gctgaaacgc gagagaaacc gcgtgtcaac tgtacaacag 180
ttgacaaaga gattctcact tggaatgctg cagggacgag gaccactaaa attgttcatg 240
gccctggtgg cattccttcg tttcctaaca atcccaccaa cagcagggat attaaaaaga 300
tggggaacaa ttaaaaaatc aaaggctatt aatgttctga gaggcttcag gaaagagatt 360
ggaaggatgc tgaatatctt aaacaggaga cgtagaactg taggcatgat catcatgctg 420
actccaacag tgatggcgtt tcatctgacc acacgcaacg gagaaccaca catgattgtc 480
agtagacaag aaaaagggaa aagccttctg ttcaagacaa aggatggcac gaacatgtgt 540
accctcatgg ccatggacct tggtgagttg tgtgaagaca caatcacgta taaatgtcct 600
tttctcaagc agaacgaacc agaagacata gattgttggt gcaactccac gtccacatgg 660
gtaacttatg ggacatgtac caccacagga gagcacagaa gagaaaaaag atcagtggcg 720

```
cttgttccac acgtgggaat gggattggag acacgaactg aaacatggat gtcatcagaa    780
ggggcctgga acatgccca gagaattgaa acttggattc tgagacatcc aggctttacc    840
ataatggccg caatcctggc atacaccata gggacgacgc atttccaaag agtcctgata    900
ttcatcctac tgacagccat cgctccttca atgacaatgc gctgcatagg aatatcaaat    960
agggactttg tggaaggagt gtcaggaggg agttgggttg acatagtttt agaacatgga   1020
agttgtgtga cgacgatggc aaaaaacaaa ccaacactgg actttgaact gataaaaaca   1080
gaagccaaac aacctgccac cttaaggaag tactgtatag aggccaaact gaccaacacg   1140
acaacagact cgcgctgccc aacacaaggg aacccaccc tgaatgaaga gcaggacaaa    1200
aggtttgtct gcaaacattc catggtagac agaggatggg gaaatggatg tggattgttt   1260
ggaaaaggag gcatcgtgac ctgtgctatg ttcacatgca aaaagaacat ggaaggaaaa   1320
attgtgcagc cagaaaacct ggaatacact gtcgtgataa acctcattc aggggaagaa   1380
catgcagtgg gaaatgacac aggaaaacat ggtaaagaag tcaagataac accacagagc   1440
tccatcacag aggcggaact gacaggctat ggcactgtta cgatggagtg ctctccaaga   1500
acgggcctcg acttcaatga gatggtgttg ctgcaaatgg aagacaaagc ctggctggtg   1560
cacagacaat ggttcctaga cctaccgttg ccatggctgc ccggagcaga cacacaagga   1620
tcaaattgga tacagaaaga aacactggtc accttcaaaa atccccatgc gaaaaaacag   1680
gatgttgttg tcttaggatc ccaagagggg gccatgcata cagcactcac aggggctacg   1740
gaaatccaga tgtcatcagg aaacctgctg ttcacaggac atctcaagtg caggctgaga   1800
atggacaaat acaacttaa agggatgtca tactccatgt gcacaggaaa gtttaaaatt   1860
gtgaaggaaa tagcagaaac acaacatgga acaatagtca ttagagtaca atatgaagga   1920
gacggctctc catgcaagat ccccttgag ataatggatc tggaaaaaag acatgttttg   1980
ggccgcctga tcacagtcaa cccaattgta acagaaaagg acagtccagt caacatagaa   2040
gcagaacctc cattcggaga cagctacatc atcataggag tggaaccagg acaattgaag   2100
ctggactggt tcaagaaagg aagttccatc ggccaaatgt ttgagacaac aatgagggga   2160
gcgaaaagaa tggccatttt gggtgacaca gcctgggatt ttggatctct gggaggagtg   2220
ttcacatcaa taggaaaggc tctccaccag gttttggag caatctacgg ggctgctttc   2280
agtgggtct catggactat gaagatcctc ataggagtta tcatcacatg gataggaatg   2340
aactcacgta gcactagtct gagcgtgtca ctggtgttag tgggaatcgt gacactttac   2400
ttgggagtta tggtgcaggc cgatagtggt tgcgttgtga gctggaagaa caaagaacta   2460
aaatgtggca gtggaatatt cgtcacagat aacgtgcata catggacaga acaatacaag   2520
ttccaaccag aatcccctc aaaactggcc tcagccatcc agaaagcgca tgaagagggc   2580
atctgtggaa tccgctcagt aacaagactg gaaaatctta tgtggaaaca gataacatca   2640
gaattgaatc atattctatc agaaaatgaa gtgaaactga ccatcatgac aggagacatc   2700
aaaggaatca tgcaggtagg aaaacgatct ttgcggcctc aacccactga gttgaggtat   2760
tcatggaaaa catggggtaa agcgaaaatg ctctccacag aactccacaa tcagaccttc   2820
ctcattgatg tcccgaaaac agcagaatgc cccaacacaa acagagcttg gaattcactg   2880
gaagttgagg actacggctt tggagtattc actaccaata tatggctaag attgagagaa   2940
aagcaggatg tattttgtga ctcaaaactc atgtcagcgg ccataaagga caacagagcc   3000
gtccatgctg atatgggtta ttggatagaa agcgcactca tgatacatg gaagatagag   3060
aaagcttctt tcattgaagt caaaagttgc cactggccaa agtcacacac cctatggagt   3120
```

```
aatggagtgc tagaaagcga gatggtcatt ccaaagaatt tcgctggacc agtgtcacaa    3180
cataataaca gaccaggcta ttacacacaa acagcaggac cttggcatct aggcaagctt    3240
gagatggact tgatttctg cgaagggact acagtggtgg taaccgagaa ctgtggaaac    3300
agagggccct ctttaagaac aaccactgcc tcaggaaaac tcataacgga atggtgttgt    3360
cgatcttgca cactaccacc actaagatac agaggtgagg atggatgttg gtacgggatg    3420
gaaatcagac cattgaaaga gaagaagaa aatctggtca gttctctggt tacagccgga    3480
catgggcaga ttgacaattt ctcattagga atcttgggaa tggcactgtt ccttgaagaa    3540
atgctcagga ctcgagtagg aacaaaacat gcaatattac tcgtcgcagt ttctttcgtg    3600
acgctaatca cagggaacat gtcttttaga gacctgggaa gagtgatggt tatggtgggt    3660
gccaccatga cagatgacat aggcatgggt gtgacttatc tcgctctact agcagctttt    3720
agagtcagac caacctttgc agctggactg ctcttgagaa aactgacctc caaggaatta    3780
atgatgacta ccataggaat cgttcttctc tcccagagta gcataccaga gaccattctt    3840
gaactgaccg acgcgttagc tctaggcatg atggtcctca agatggtgag aaacatggaa    3900
aaatatcagc tggcagtgac catcatggct attttgtgcg tcccaaatgc tgtgatatta    3960
cagaacgcat ggaaagtgag ttgcacaata ttggcagtgg tgtctgtttc ccccctgctc    4020
ttaacatcct cacaacagaa agcggactgg ataccattag cgttgacgat caaaggtctt    4080
aatccaacag ccattttct aacaaccctc tcaagaacca acaagaaaag gagctggcct    4140
ttaaatgagg ccatcatggc ggttgggatg gtgagtatct tggccagctc tctcttaaag    4200
aatgacatcc ccatgacagg accattagtg gctggagggc tccttactgt gtgctacgtg    4260
ctaactgggc ggtcagccga tctggaatta gagagagcta ccgatgtcaa atgggatgac    4320
caggcagaga tatcaggtag cagtccaatc ctgtcaataa caatatcaga gatggcagc    4380 atgtcaataa agaatgaaga ggaagagcaa acactgacta tactcattag aacaggattg    4440
cttgtgatct caggactctt tccggtatca ataccaatta cagcagcagc atggtatctg    4500
tgggaagtaa agaaacaacg ggctggagtg ctgtgggatg tcccctcacc accacccgtg    4560
ggaaaagctg aattggaaga tggagcctac agaatcaagc aaaaaggaat ccttggatat    4620
tcccagatcg gagctggagt ttacaaagaa ggaacatttc acacaatgtg gcacgtcaca    4680
cgtggcgctg tcctaatgca taagggggaag aggattgaac catcatggc ggacgtcaag    4740 aaagacttaa tatcatatgg aggaggttgg aagctagaag gagaatggaa agaaggagaa    4800
gaagtccagg tcttggcatt ggagccaggg aaaaatccaa gagccgtcca aacaaagcct    4860
ggccttttta gaaccaacac tggaaccata ggtgccgtat ctctggactt ttcccctggg    4920
acgtcaggat ctccaatcgt cgacaaaaaa ggaaaagttg taggtctcta tggcaatggt    4980
gtcgttacaa ggagtggagc atatgtgagt gccatagctc agactgaaaa aagcattgaa    5040
gacaatccag agattgaaga tgacatcttt cgaaagagaa gattgactat catggatctc    5100
cacccaggag caggaaagac aaagagatac ctcccggcca tagtcagaga ggccataaaa    5160
agaggcttga gaacactaat cctagccccc actagagtcg tggcagctga aatggaggaa    5220
gcccttagag gacttccaat aagataccaa actccagcta tcagggctga gcacaccggg    5280
cgggagattg tagacttaat gtgtcatgcc acatttacca tgaggctgct atcaccaatc    5340
agggtgccaa attacaacct gatcatcatg gacgaagccc attttacaga tccagcaagc    5400
atagcagcta ggggatacat ctcaactcga gtggagatgg gggaggcagc tggaattttt    5460
```

-continued

```
atgacagcca ctcctccggg tagtagagat ccatttcctc agagcaatgc accaattatg    5520
gacgaagaaa gagaaattcc ggaacgttca tggaactctg gcacgagtg ggtcacggat      5580
tttaaaggaa agactgtctg gtttgttcca agcataaaaa ccggaaatga catagcagcc    5640
tgcctgagaa agaatggaaa gagggtgata caactcagta ggaagacctt tgattctgaa     5700
tatgtcaaga ctagaaccaa tgactgggat ttcgtggtta caactgacat ctcggaaatg    5760
ggcgccaact ttaaagctga gagggtcata gaccccagac gctgcatgaa accagttata    5820
ttgacagacg gcgaagagcg ggtgattctg gcaggaccca tgccagtgac ccactctagt   5880
gcagcacaaa gaagagggag aataggaagg aatccaagga atgaaaatga tcaatatata    5940
tatatggggg aaccactgga aaatgatgaa gactgtgcgc actggaagga agctaagatg    6000
ctcctagata atatcaacac acctgaagga atcattccca gcttgttcga gccagagcgt   6060
gaaaaggtgg atgccattga cggtgaatat cgcttgagag gagaagcacg gaaaactttt   6120
gtggacctaa tgagaagagg agacctacca gtctggttgg cttataaagt ggcagctgaa   6180
ggtatcaact acgcagacag aagatggtgt tttgacggaa ccagaaacaa tcaaatcttg    6240
gaagaaaatg tggaagtgga aatctggaca aaggaagggg aaaggaaaaa attgaaacct    6300
agatggttag atgctaggat ctactccgac ccactggcgc taaaagagtt caaggaattt    6360
gcagccggaa gaaagtccct aacccctgaac ctaattacag agatgggcag actcccaact   6420
tttatgactc agaaggccag agatgcacta gacaacttgg cggtgctgca cacggctgaa   6480
gcgggtggaa aggcatacaa tcatgctctc agtgaattac cggagaccct ggagacattg   6540
cttttgctga cactgttggc cacagtcacg ggaggaatct tcctattcct gatgagcgga    6600
agggtatgg ggaagatgac cctgggaatg tgctgcataa tcacggccag catcctctta   6660
tggtatgcac aaatacagcc acattggata gcagcctcaa taatattgga gttctttctc    6720
atagtcttgc tcattccaga accagaaaag cagaggacac ctcaggataa tcaattgact   6780
tatgtcatca tagccatcct cacagtggtg gccgcaacca tggcaaacga atgggttttt    6840
ctggaaaaaa caaagaaaga cctcggactg ggaaacattg caactcagca acctgagagc   6900
aacattctgg acatagatct acgtcctgca tcagcatgga cgttgtatgc cgtggctaca    6960
acatttatca caccaatgtt gagacatagc attgaaaatt cctcagtaaa tgtgtcccta    7020
acagccatag ctaaccaagc cacagtgcta atgggtctcg gaaaaggatg gccattgtca   7080
aagatggaca ttggagttcc cctccttgct attgggtgtt actcacaagt caaccctata   7140
accctcacag cggctcttct tttattggta gcacattatg ccatcatagg accgggactt   7200
caagccaaag caactagaga agctcagaaa agagcagcag cgggcatcat gaaaaaccca   7260
actgtggatg gaataacagt gatagatcta gatccaatac cctatgatcc aaagtttgaa    7320
aagcagttgg gacaagtaat gctcctagtc ctctgcgtga cccaagtgct gatgatgagg   7380
actacgtggg ctttgtgtga agccttaact ctagcaactg gacccgtgtc acattgtggg    7440
gaaggaaatc cagggagatt ctggaacaca accattgcag tgtcaatggc aaacatcttt    7500
agagggagtt acctggctgg agctggactt ctcttttcta tcatgaagaa cacaaccagc   7560
acgagaagag gaactggcaa tataggagaa acgttaggag agaaatggaa aagcagactg   7620
aacgcattgg ggaaaagtga attccagatc tacaaaaaaa gtggaattca agaagtggac   7680
agaaccttag caaaagaagg cattaaaaga ggagaaacgg atcatcacgc tgtgtcgcga    7740
ggctcagcaa aactgagatg gttcgttgaa aggaatttgg tcacaccaga agggaaagta   7800
gtggaccttg gttgtggcag agggggctgg tcatactatt gtggaggatt aaagaatgta    7860
```

```
agagaagtta aaggcttaac aaaaggagga ccaggacacg aagaacctat ccctatgtca   7920
acatatgggt ggaatctagt acgcttacag agcggagttg atgttttttt tgttccacca   7980
gagaagtgtg acacattgtt gtgtgacata ggggaatcat caccaaatcc cacggtagaa   8040
gcgggacgaa cactcagagt cctcaaccta gtggaaaatt ggctgaacaa taacacccaa   8100
ttttgcgtaa aggttcttaa cccgtacatg ccctcagtca ttgaaagaat ggaaaccttA   8160
caacggaaat acgaggagc cttggtgaga atccactct cacggaattc cacacatgag    8220
atgtactggg tgtccaatgc ttccgggaac atagtgtcat cagtgaacat gatttcaaga   8280
atgctgatca acagattcac tatgagacac aagaaggcca cctatgagcc agatgtcgac   8340
ctcggaagcg gaacccgcaa tattggaatt gaaagtgaga caccgaacct agacataatt   8400
gggaaaagaa tagaaaaaat aaaacaagag catgaaacgt catggcacta tgatcaagac   8460
cacccataca aaacatgggc ttaccatggc agctatgaaa caaaacagac tggatcagca   8520
tcatccatgg tgaacggagt agtcagattg ctgacaaaac cctgggacgt tgttccaatg   8580
gtgacacaga tggcaatgac agacacaact cctttggac aacagcgcgt cttcaaagag    8640
aaggtggata cgagaaccca agaaccaaaa gaaggcacaa aaaaactaat gaaaatcacg   8700
gcagagtggc tctggaaaga actaggaaag aaaaagacac ctagaatgtg taccagagaa   8760
gaattcacaa aaaaggtgag aagcaatgca gccttggggg ccatattcac cgatgagaac   8820
aagtggaaat cggcgcgtga agccgttgaa gatagtaggt tttgggagct ggttgacaag   8880
gaaaggaacc tccatcttga agggaaatgt gaaacatgtg tatacaacat gatggggaaa   8940
agagagaaaa aactaggaga gtttggtaaa gcaaaaggca gcagagccat atggtacatg   9000
tggctcggag cacgcttctt agagtttgaa gcccctaggat ttttgaatga agaccattgg   9060
ttctccagag agaactccct gagtggagtg aaggagaag ggctgcataa gctaggttac    9120
atcttaagag aggtgagcaa gaaagaagga ggagcaatgt atgccgatga caccgcaggc   9180
tgggacacaa gaatcacaat agaggatttg aaaaatgaag aaatgataac gaaccacatg   9240
gcaggagaac acaagaaact tgccgaggcc atttttaaat tgacgtacca aaacaaggtg   9300
gtgcgtgtgc aaagaccaac accaagaggc acagtaatgg acatcatatc gagaagagac   9360
caaaggggta gtggacaagt tggcacctat ggcctcaaca cttttcaccaa catggaagca   9420 caactaatta ggcaaatgga gggggaagga atcttcaaaa gcatccagca cttgacagcc   9480
tcagaagaaa tcgctgtgca agattggcta gtaagagtag ggcgtgaaag gttgtcaaga   9540
atggccatca gtgagatga ttgtgttgtg aaacctttag atgatagatt tgcaagagct    9600
ctaacagctc taaatgacat gggaaaggtt aggaaggaca tacagcaatg ggagccctca   9660
agaggatgga acgactggac gcaggtgccc ttctgttcac accatttca cgagttaatt    9720 atgaaagatg gtcgcacact cgtagttcca tgcagaaacc aagatgaatt gatcggcaga   9780
gcccgaattt cccagggagc tgggtggtct ttacgggaga cggcctgttt ggggaagtct   9840
tacgcccaaa tgtggagctt gatgtacttc cacagacgtg atctcaggct agcggcaaat   9900
gccatctgct cggcagtccc atcacactgg attccaacaa gccggacaac ctggtccata   9960
cacgccagca tgaatggat gacgacgaa gacatgttga cagtttggaa cagagtgtgg  10020
atcctagaaa atccatggat ggaagacaaa actccagtgg aatcatggga ggaaatccca  10080 tacctggaa aaagagaaga ccaatggtgc ggctcgctga ttgggctgac aagcagagcc  10140
acctgggcga agaatatcca gacagcaata aaccaagtca gatccctcat tggcaatgag  10200
```

```
gaatacacag attacatgcc atccatgaaa agattcagaa gagaagagga agaggcagga   10260
gttttgtggt agaaaaacat gaaacaaaac agaagtcagg tcggattaag ccatagtacg   10320
ggaaaaacta tgctacctgt gagccccgtc caaggacgtt aaaagaagtc aggccatttt   10380
gatgccatag cttgagcaaa ctgtgcagcc tgtagctcca cctgagaagg tgtaaaaaat   10440
ccgggaggcc acaaccatg gaagctgtac gcatggcgta gtggactagc ggttagagga    10500
gaccctccc ttacagatcg cagcaacaat ggggcccaa ggtgagatga agctgtagtc     10560
tcactggaag gactagaggt tagaggagac cccccaaaa caaaaaacag catattgacg    10620
ctgggaaaga ccagagatcc tgctgtctcc tcagcatcat tccaggcaca ggacgccaga   10680
aaatggaatg gtgctgttga atcaacaggt tctggtaccg gtaggcatcg tggtgtcacg   10740
ctcgtcgttt ggtatggctt cattcagctc cggttcccaa cgatcaaggc gagttacatg   10800
atcccccatg ttgtgcaaaa aagcggttag ctccttcggt cctccgatcg ttgtcagaag   10860
taagttggcc gcagtgttat cactcatggt tatggcagca ctgcataatt ctcttactgt   10920
catgccatcc gtaagatgct tttctgtgac tggtgagtac tcaaccaagt cattctgaga   10980
atagtgtatg cggcgaccga gttgctcttg cccggcgtca acacgggata ataccgcgcc   11040
acatagcaga actttaaaag tgctcatcat tggaaaacgt tcttcggggc gaaaactctc   11100
aaggatctta ccgctgttga gatccagttc gatgtaaccc actcgtgcac ccaactgatc   11160
ttcagcatct tttactttca ccagcgtttc tgggtgagca aaaacaggaa ggcaaaatgc   11220
cgcaaaaaag ggaataaggg cgacacggaa atgttgaata ctcatactct tccttttca    11280
atattattga agcatttatc agggttattg tctcatgagc ggatacatat ttgaatgtat   11340
ttagaaaaat aaacaaatag gggttccgcg cacatttccc cgaaaagtgc cacctgacgt   11400
ctaagaaacc attattatca tgacattaac ctataaaaat aggcgtatca cgaggccctt   11460
tcgtcttcaa gaattctcat gtttgacagc ttatcatcga taagctttaa tgcggtagtt   11520
tatcacagtt aaattgctaa cgcagtcagg caccgtgtat gaaatctaac aatgcgctca   11580
tcgtcatcct cggcaccgtc accctggatg ctgtaggcat aggcttggtt atgccggtac   11640
tgccgggcct cttgcgggat atcgtccatt ccgacagcat cgccagtcac tatggcgtgc   11700
tgctggcgct atatgcgttg atgcaatttc tatgcgcacc cgttctcgga gcactgtccg   11760
accgctttgg ccgccgccca gtcctgctcg cttcgctact tggagccact atcgactacg   11820
cgatcatggc gaccacaccc gtcctgtgga tcctctacgc cggacgcatc gtggccggca   11880
tcaccggcgc cacaggtgcg gttgctggcg cctatatcgc cgacatcacc gatgggaag    11940
atcgggctcg ccacttcggg ctcatgagcg cttgtttcgg cgtgggtatg gtggcaggcc   12000
ccgtggccgg gggactgttg gcgccatct ccttgcatgc accattcctt gcggcggcgg    12060
tgctcaacgg cctcaaccta ctactgggct gcttcctaat gcaggagtcg cataagggag   12120
agcgtcgacc gatgcccttg agagccttca acccagtcag ctccttccgg tgggcgcggg   12180
gcatgactat cgtcgccgca cttatgactg tcttctttat catgcaactc gtaggacagg   12240
tgccggcagc gctctgggtc attttcggcg aggaccgctt tcgctggagc gcgacgatga   12300
tcggcctgtc gcttgcggta ttcggaatct tgcacgccct cgctcaagcc ttcgtcactg   12360
gtcccgccac caaacgtttc ggcgagaagc aggccattat cgccggcatg gcggccgacg   12420
cgctgggcta cgtcttgctg gcgttcgcga cgcgaggctg gatggccttc cccattatga   12480
ttcttctcgc ttccggcggc atcgggatgc ccgcgttgca ggccatgctg tccaggcagg   12540
tagatgacga ccatcaggga cagcttcaag gatcgctcgc ggctcttacc agcctaactt   12600
```

```
cgatcactgg accgctgatc gtcacggcga tttatgccgc ctcggcgagc acatggaacg   12660
ggttggcatg gattgtaggc gccgccctat accttgtctg cctccccgcg ttgcgtcgcg   12720
gtgcatggag ccgggccacc tcgacctgaa tggaagccgg cggcacctcg ctaacggatt   12780
caccactcca agaattggag ccaatcaatt cttgcggaga actgtgaatg cgcaaaccaa   12840
cccttggcag aacatatcca tcgcgtccgc catctccagc agccgcacgc ggcgcatctc   12900
gggcagcgtt gggtcctggc cacgggtgcg catgatcgtg ctcctgtcgt tgaggacccg   12960
gctaggctgg cggggttgcc ttactggtta gcagaatgaa tcaccgatac gcgagcgaac   13020
gtgaagcgac tgctgctgca aaacgtctgc gacctgagca acaacatgaa tggtcttcgg   13080
tttccgtgtt tcgtaaagtc tggaaacgcg aagtcagcg ccctgcacca ttatgttccg   13140
gatctgcatc gcaggatgct gctggctacc ctgtggaaca cctacatctg tattaacgaa   13200
gcgctggcat tgaccctgag tgatttttct ctggtcccgc cgcatccata ccgccagttg   13260
tttaccctca caacgttcca gtaaccgggc atgttcatca tcagtaaccc gtatcgtgag   13320
catcctctct cgtttcatcg gtatcattac ccccatgaac agaaatcccc cttacacgga   13380
ggcatcagtg accaaacagg aaaaaaccgc ccttaacatg gcccgcttta tcagaagcca   13440
gacattaacg cttctggaga aactcaacga gctggacgcg gatgaacagg cagacatctg   13500
tgaatcgctt cacgaccacg ctgatgagct ttaccgcagc tgcctcgcgc gtttcggtga   13560
tgacggtgaa aacctctgac acatgcagct cccggagacg gtcacagctt gtctgtaagc   13620
ggatgccggg agcagacaag cccgtcaggg cgcgtcagcg ggtgttggcg ggtgtcgggg   13680
cgcagccatg acccagtcac gtagcgatag cggagtgtat actggcttaa ctatgcggca   13740
tcagagcaga ttgtactgag agtgcaccat atgcggtgtg aaataccgca cagatgcgta   13800
aggagaaaat accgcatcag gcgctcttcc gcttcctcgc tcactgactc gctgcgctcg   13860
gtcgttcggc tgcggcgagc ggtatcagct cactcaaagg cggtaatacg gttatccaca   13920
gaatcagggg ataacgcagg aaagaacatg tgagcaaaag gccagcaaaa ggccaggaac   13980
cgtaaaaagg ccgcgttgct ggcgtttttc cataggctcc gccccctga cgagcatcac   14040 aaaaatcgac gctcaagtca gaggtggcga acccgacag gactataaag ataccaggcg   14100
tttccccctg gaagctccct cgtgcgctct cctgttccga ccctgccgct taccggatac   14160
ctgtccgcct ttctcccttc gggaagcgtg gcgctttctc atagctcacg ctgtaggtat   14220
ctcagttcgg tgtaggtcgt tcgctccaag ctgggctgtg tgcacgaacc ccccgttcag   14280
cccgaccgct gcgccttatc cggtaactat cgtcttgagt ccaacccggt aagacacgac   14340
ttatcgccac tggcagcagc cactggtaac aggattagca gagcgaggta tgtaggcggt   14400
gctacagagt tcttgaagtg gtggcctaac tacggctaca ctagaaggac agtatttggt   14460
atctgcgctc tgctgaagcc agttaccttc ggaaaaagag ttggtagctc ttgatccggc   14520
aaacaaacca ccgctggtag cggtggtttt tttgtttgca agcagcagat tacgcgcaga   14580
aaaaaaggat ctcaagaaga tcctttgatc ttttctacgg ggtctgacgc tcagtggaac   14640
gaaaactcac gttaagggat tttggtcatg agattatcaa aaaggatctt cacctagatc   14700
cttttaaatt aaaaatgaag ttttaaatca atctaaagta tatatgagta aacttggtct   14760
gacagttacc aatgcttaat cagtgaggca cctatctcag cgatctgtct atttcgttca   14820
tccatagttg cctgactccc cgtcgtgtag ataactacga tacgggaggg cttaccatct   14880
ggccccagtg ctgcaatgat accgcgagac ccacgctcac cggctccaga tttatcagca   14940
```

-continued

```
ataaaccagc cagccggaag ggccgagcgc agaagtggtc ctgcaacttt atccgcctcc    15000
atccagtcta ttaattgttg ccgggaagct agagtaagta gttcgccagt taatagtttg    15060
cgcaacgttg ttgccattgc tgcaagatct ggctagcgat gaccctgctg attggttcgc    15120
tgaccatttc cgggcgcgcc gatttaggtg acactatag                           15159
```

<210> SEQ ID NO 31
<211> LENGTH: 3391
<212> TYPE: PRT
<213> ORGANISM: Dengue 2 (Tonga/74)

<400> SEQUENCE: 31

```
Met Asn Asn Gln Arg Lys Lys Ala Arg Asn Thr Pro Phe Asn Met Leu
1               5                  10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Val Gly Met Ile Ile Met Leu Thr Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Lys Asp Gly
    130                 135                 140

Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335
```

-continued

```
Arg Lys Tyr Cys Ile Glu Ala Lys Leu Thr Asn Thr Thr Asp Ser
            340                 345                 350
Arg Cys Pro Thr Gln Gly Glu Pro Thr Leu Asn Glu Glu Gln Asp Lys
        355                 360                 365
Arg Phe Val Cys Lys His Ser Met Val Asp Arg Gly Trp Gly Asn Gly
    370                 375                 380
Cys Gly Leu Phe Gly Lys Gly Ile Val Thr Cys Ala Met Phe Thr
385                 390                 395                 400
Cys Lys Lys Asn Met Glu Gly Lys Ile Val Gln Pro Glu Asn Leu Glu
                405                 410                 415
Tyr Thr Val Val Ile Thr Pro His Ser Gly Glu Glu His Ala Val Gly
            420                 425                 430
Asn Asp Thr Gly Lys His Gly Lys Glu Val Lys Ile Thr Pro Gln Ser
        435                 440                 445
Ser Ile Thr Glu Ala Glu Leu Thr Gly Tyr Gly Thr Val Thr Met Glu
    450                 455                 460
Cys Ser Pro Arg Thr Gly Leu Asp Phe Asn Glu Met Val Leu Leu Gln
465                 470                 475                 480
Met Glu Asp Lys Ala Trp Leu Val His Arg Gln Trp Phe Leu Asp Leu
                485                 490                 495
Pro Leu Pro Trp Leu Pro Gly Ala Asp Thr Gln Gly Ser Asn Trp Ile
            500                 505                 510
Gln Lys Glu Thr Leu Val Thr Phe Lys Asn Pro His Ala Lys Lys Gln
        515                 520                 525
Asp Val Val Val Leu Gly Ser Gln Glu Gly Ala Met His Thr Ala Leu
    530                 535                 540
Thr Gly Ala Thr Glu Ile Gln Met Ser Ser Gly Asn Leu Leu Phe Thr
545                 550                 555                 560
Gly His Leu Lys Cys Arg Leu Arg Met Asp Lys Leu Gln Leu Lys Gly
                565                 570                 575
Met Ser Tyr Ser Met Cys Thr Gly Lys Phe Lys Ile Val Lys Glu Ile
            580                 585                 590
Ala Glu Thr Gln His Gly Thr Ile Val Ile Arg Val Gln Tyr Glu Gly
        595                 600                 605
Asp Gly Ser Pro Cys Lys Ile Pro Phe Glu Ile Met Asp Leu Glu Lys
    610                 615                 620
Arg His Val Leu Gly Arg Leu Ile Thr Val Asn Pro Ile Val Thr Glu
625                 630                 635                 640
Lys Asp Ser Pro Val Asn Ile Glu Ala Glu Pro Pro Phe Gly Asp Ser
                645                 650                 655
Tyr Ile Ile Ile Gly Val Glu Pro Gly Gln Leu Lys Leu Asp Trp Phe
            660                 665                 670
Lys Lys Gly Ser Ser Ile Gly Gln Met Phe Glu Thr Thr Met Arg Gly
        675                 680                 685
Ala Lys Arg Met Ala Ile Leu Gly Asp Thr Ala Trp Asp Phe Gly Ser
    690                 695                 700
Leu Gly Gly Val Phe Thr Ser Ile Gly Lys Ala Leu His Gln Val Phe
705                 710                 715                 720
Gly Ala Ile Tyr Gly Ala Ala Phe Ser Gly Val Ser Trp Thr Met Lys
                725                 730                 735
Ile Leu Ile Gly Val Ile Ile Thr Trp Ile Gly Met Asn Ser Arg Ser
            740                 745                 750
Thr Ser Leu Ser Val Ser Leu Val Leu Val Gly Ile Val Thr Leu Tyr
```

-continued

```
            755                 760                 765
Leu Gly Val Met Val Gln Ala Asp Ser Gly Cys Val Val Ser Trp Lys
            770                 775                 780
Asn Lys Glu Leu Lys Cys Gly Ser Gly Ile Phe Val Thr Asp Asn Val
785                 790                 795                 800
His Thr Trp Thr Glu Gln Tyr Lys Phe Gln Pro Glu Ser Pro Ser Lys
                    805                 810                 815
Leu Ala Ser Ala Ile Gln Lys Ala His Glu Glu Gly Ile Cys Gly Ile
                    820                 825                 830
Arg Ser Val Thr Arg Leu Glu Asn Leu Met Trp Lys Gln Ile Thr Ser
                    835                 840                 845
Glu Leu Asn His Ile Leu Ser Glu Asn Glu Val Lys Leu Thr Ile Met
            850                 855                 860
Thr Gly Asp Ile Lys Gly Ile Met Gln Val Gly Lys Arg Ser Leu Arg
865                 870                 875                 880
Pro Gln Pro Thr Glu Leu Arg Tyr Ser Trp Lys Thr Trp Gly Lys Ala
                    885                 890                 895
Lys Met Leu Ser Thr Glu Leu His Asn Gln Thr Phe Leu Ile Asp Gly
            900                 905                 910
Pro Glu Thr Ala Glu Cys Pro Asn Thr Asn Arg Ala Trp Asn Ser Leu
            915                 920                 925
Glu Val Glu Asp Tyr Gly Phe Gly Val Phe Thr Asn Ile Trp Leu
            930                 935                 940
Arg Leu Arg Glu Lys Gln Asp Val Phe Cys Asp Ser Lys Leu Met Ser
945                 950                 955                 960
Ala Ala Ile Lys Asp Asn Arg Ala Val His Ala Asp Met Gly Tyr Trp
                    965                 970                 975
Ile Glu Ser Ala Leu Asn Asp Thr Trp Lys Ile Glu Lys Ala Ser Phe
                    980                 985                 990
Ile Glu Val Lys Ser Cys His Trp Pro Lys Ser His Thr Leu Trp Ser
                    995                 1000                1005
Asn Gly Val Leu Glu Ser Glu Met Val Ile Pro Lys Asn Phe Ala
            1010                1015                1020
Gly Pro Val Ser Gln His Asn Asn Arg Pro Gly Tyr Tyr Thr Gln
            1025                1030                1035
Thr Ala Gly Pro Trp His Leu Gly Lys Leu Glu Met Asp Phe Asp
            1040                1045                1050
Phe Cys Glu Gly Thr Thr Val Val Val Thr Glu Asn Cys Gly Asn
            1055                1060                1065
Arg Gly Pro Ser Leu Arg Thr Thr Ala Ser Gly Lys Leu Ile
            1070                1075                1080
Thr Glu Trp Cys Cys Arg Ser Cys Thr Leu Pro Pro Leu Arg Tyr
            1085                1090                1095
Arg Gly Glu Asp Gly Cys Trp Tyr Gly Met Glu Ile Arg Pro Leu
            1100                1105                1110
Lys Glu Lys Glu Glu Asn Leu Val Ser Ser Leu Val Thr Ala Gly
            1115                1120                1125
His Gly Gln Ile Asp Asn Phe Ser Leu Gly Ile Leu Gly Met Ala
            1130                1135                1140
Leu Phe Leu Glu Glu Met Leu Arg Thr Arg Val Gly Thr Lys His
            1145                1150                1155
Ala Ile Leu Leu Val Ala Val Ser Phe Val Thr Leu Ile Thr Gly
            1160                1165                1170
```

```
Asn Met Ser Phe Arg Asp Leu Gly Arg Val Met Val Met Val Gly
    1175            1180            1185

Ala Thr Met Thr Asp Asp Ile Gly Met Gly Val Thr Tyr Leu Ala
    1190            1195            1200

Leu Leu Ala Ala Phe Arg Val Arg Pro Thr Phe Ala Ala Gly Leu
    1205            1210            1215

Leu Leu Arg Lys Leu Thr Ser Lys Glu Leu Met Met Thr Thr Ile
    1220            1225            1230

Gly Ile Val Leu Leu Ser Gln Ser Ser Ile Pro Glu Thr Ile Leu
    1235            1240            1245

Glu Leu Thr Asp Ala Leu Ala Leu Gly Met Met Val Leu Lys Met
    1250            1255            1260

Val Arg Asn Met Glu Lys Tyr Gln Leu Ala Val Thr Ile Met Ala
    1265            1270            1275

Ile Leu Cys Val Pro Asn Ala Val Ile Leu Gln Asn Ala Trp Lys
    1280            1285            1290

Val Ser Cys Thr Ile Leu Ala Val Val Ser Val Ser Pro Leu Leu
    1295            1300            1305

Leu Thr Ser Ser Gln Gln Lys Ala Asp Trp Ile Pro Leu Ala Leu
    1310            1315            1320

Thr Ile Lys Gly Leu Asn Pro Thr Ala Ile Phe Leu Thr Thr Leu
    1325            1330            1335

Ser Arg Thr Asn Lys Lys Arg Ser Trp Pro Leu Asn Glu Ala Ile
    1340            1345            1350

Met Ala Val Gly Met Val Ser Ile Leu Ala Ser Ser Leu Leu Lys
    1355            1360            1365

Asn Asp Ile Pro Met Thr Gly Pro Leu Val Ala Gly Gly Leu Leu
    1370            1375            1380

Thr Val Cys Tyr Val Leu Thr Gly Arg Ser Ala Asp Leu Glu Leu
    1385            1390            1395

Glu Arg Ala Thr Asp Val Lys Trp Asp Asp Gln Ala Glu Ile Ser
    1400            1405            1410

Gly Ser Ser Pro Ile Leu Ser Ile Thr Ile Ser Glu Asp Gly Ser
    1415            1420            1425

Met Ser Ile Lys Asn Glu Glu Glu Glu Gln Thr Leu Thr Ile Leu
    1430            1435            1440

Ile Arg Thr Gly Leu Leu Val Ile Ser Gly Leu Phe Pro Val Ser
    1445            1450            1455

Ile Pro Ile Thr Ala Ala Ala Trp Tyr Leu Trp Glu Val Lys Lys
    1460            1465            1470

Gln Arg Ala Gly Val Leu Trp Asp Val Pro Ser Pro Pro Pro Val
    1475            1480            1485

Gly Lys Ala Glu Leu Glu Asp Gly Ala Tyr Arg Ile Lys Gln Lys
    1490            1495            1500

Gly Ile Leu Gly Tyr Ser Gln Ile Gly Ala Gly Val Tyr Lys Glu
    1505            1510            1515

Gly Thr Phe His Thr Met Trp His Val Thr Arg Gly Ala Val Leu
    1520            1525            1530

Met His Lys Gly Lys Arg Ile Glu Pro Ser Trp Ala Asp Val Lys
    1535            1540            1545

Lys Asp Leu Ile Ser Tyr Gly Gly Gly Trp Lys Leu Glu Gly Glu
    1550            1555            1560
```

```
Trp Lys Glu Gly Glu Glu Val Gln Val Leu Ala Leu Glu Pro Gly
1565                1570                1575

Lys Asn Pro Arg Ala Val Gln Thr Lys Pro Gly Leu Phe Arg Thr
1580                1585                1590

Asn Thr Gly Thr Ile Gly Ala Val Ser Leu Asp Phe Ser Pro Gly
1595                1600                1605

Thr Ser Gly Ser Pro Ile Val Asp Lys Lys Gly Lys Val Val Gly
1610                1615                1620

Leu Tyr Gly Asn Gly Val Val Thr Arg Ser Gly Ala Tyr Val Ser
1625                1630                1635

Ala Ile Ala Gln Thr Glu Lys Ser Ile Glu Asp Asn Pro Glu Ile
1640                1645                1650

Glu Asp Asp Ile Phe Arg Lys Arg Arg Leu Thr Ile Met Asp Leu
1655                1660                1665

His Pro Gly Ala Gly Lys Thr Lys Arg Tyr Leu Pro Ala Ile Val
1670                1675                1680

Arg Glu Ala Ile Lys Arg Gly Leu Arg Thr Leu Ile Leu Ala Pro
1685                1690                1695

Thr Arg Val Val Ala Ala Glu Met Glu Glu Ala Leu Arg Gly Leu
1700                1705                1710

Pro Ile Arg Tyr Gln Thr Pro Ala Ile Arg Ala Glu His Thr Gly
1715                1720                1725

Arg Glu Ile Val Asp Leu Met Cys His Ala Thr Phe Thr Met Arg
1730                1735                1740

Leu Leu Ser Pro Ile Arg Val Pro Asn Tyr Asn Leu Ile Ile Met
1745                1750                1755

Asp Glu Ala His Phe Thr Asp Pro Ala Ser Ile Ala Ala Arg Gly
1760                1765                1770

Tyr Ile Ser Thr Arg Val Glu Met Gly Glu Ala Gly Ile Phe
1775                1780                1785

Met Thr Ala Thr Pro Pro Gly Ser Arg Asp Pro Phe Pro Gln Ser
1790                1795                1800

Asn Ala Pro Ile Met Asp Glu Glu Arg Glu Ile Pro Glu Arg Ser
1805                1810                1815

Trp Asn Ser Gly His Glu Trp Val Thr Asp Phe Lys Gly Lys Thr
1820                1825                1830

Val Trp Phe Val Pro Ser Ile Lys Thr Gly Asn Asp Ile Ala Ala
1835                1840                1845

Cys Leu Arg Lys Asn Gly Lys Arg Val Ile Gln Leu Ser Arg Lys
1850                1855                1860

Thr Phe Asp Ser Glu Tyr Val Lys Thr Arg Thr Asn Asp Trp Asp
1865                1870                1875

Phe Val Val Thr Thr Asp Ile Ser Glu Met Gly Ala Asn Phe Lys
1880                1885                1890

Ala Glu Arg Val Ile Asp Pro Arg Arg Cys Met Lys Pro Val Ile
1895                1900                1905

Leu Thr Asp Gly Glu Glu Arg Val Ile Leu Ala Gly Pro Met Pro
1910                1915                1920

Val Thr His Ser Ser Ala Ala Gln Arg Arg Gly Arg Ile Gly Arg
1925                1930                1935

Asn Pro Arg Asn Glu Asn Asp Gln Tyr Ile Tyr Met Gly Glu Pro
1940                1945                1950

Leu Glu Asn Asp Glu Asp Cys Ala His Trp Lys Glu Ala Lys Met
```

-continued

```
                1955                1960                1965
Leu Leu Asp Asn Ile Asn Thr Pro Glu Gly Ile Ile Pro Ser Leu
        1970                1975                1980
Phe Glu Pro Glu Arg Glu Lys Val Asp Ala Ile Asp Gly Glu Tyr
        1985                1990                1995
Arg Leu Arg Gly Glu Ala Arg Lys Thr Phe Val Asp Leu Met Arg
        2000                2005                2010
Arg Gly Asp Leu Pro Val Trp Leu Ala Tyr Lys Val Ala Ala Glu
        2015                2020                2025
Gly Ile Asn Tyr Ala Asp Arg Arg Trp Cys Phe Asp Gly Thr Arg
        2030                2035                2040
Asn Asn Gln Ile Leu Glu Glu Asn Val Glu Val Glu Ile Trp Thr
        2045                2050                2055
Lys Glu Gly Glu Arg Lys Lys Leu Lys Pro Arg Trp Leu Asp Ala
        2060                2065                2070
Arg Ile Tyr Ser Asp Pro Leu Ala Leu Lys Glu Phe Lys Glu Phe
        2075                2080                2085
Ala Ala Gly Arg Lys Ser Leu Thr Leu Asn Leu Ile Thr Glu Met
        2090                2095                2100
Gly Arg Leu Pro Thr Phe Met Thr Gln Lys Ala Arg Asp Ala Leu
        2105                2110                2115
Asp Asn Leu Ala Val Leu His Thr Ala Glu Ala Gly Gly Lys Ala
        2120                2125                2130
Tyr Asn His Ala Leu Ser Glu Leu Pro Glu Thr Leu Glu Thr Leu
        2135                2140                2145
Leu Leu Leu Thr Leu Leu Ala Thr Val Thr Gly Gly Ile Phe Leu
        2150                2155                2160
Phe Leu Met Ser Gly Arg Gly Met Gly Lys Met Thr Leu Gly Met
        2165                2170                2175
Cys Cys Ile Ile Thr Ala Ser Ile Leu Leu Trp Tyr Ala Gln Ile
        2180                2185                2190
Gln Pro His Trp Ile Ala Ala Ser Ile Ile Leu Glu Phe Phe Leu
        2195                2200                2205
Ile Val Leu Leu Ile Pro Glu Pro Glu Lys Gln Arg Thr Pro Gln
        2210                2215                2220
Asp Asn Gln Leu Thr Tyr Val Ile Ile Ala Ile Leu Thr Val Val
        2225                2230                2235
Ala Ala Thr Met Ala Asn Glu Met Gly Phe Leu Glu Lys Thr Lys
        2240                2245                2250
Lys Asp Leu Gly Leu Gly Asn Ile Ala Thr Gln Gln Pro Glu Ser
        2255                2260                2265
Asn Ile Leu Asp Ile Asp Leu Arg Pro Ala Ser Ala Trp Thr Leu
        2270                2275                2280
Tyr Ala Val Ala Thr Thr Phe Ile Thr Pro Met Leu Arg His Ser
        2285                2290                2295
Ile Glu Asn Ser Ser Val Asn Val Ser Leu Thr Ala Ile Ala Asn
        2300                2305                2310
Gln Ala Thr Val Leu Met Gly Leu Gly Lys Gly Trp Pro Leu Ser
        2315                2320                2325
Lys Met Asp Ile Gly Val Pro Leu Leu Ala Ile Gly Cys Tyr Ser
        2330                2335                2340
Gln Val Asn Pro Ile Thr Leu Thr Ala Ala Leu Leu Leu Leu Val
        2345                2350                2355
```

-continued

```
Ala His Tyr Ala Ile Ile Gly Pro Gly Leu Gln Ala Lys Ala Thr
2360            2365            2370

Arg Glu Ala Gln Lys Arg Ala Ala Gly Ile Met Lys Asn Pro
2375            2380            2385

Thr Val Asp Gly Ile Thr Val Ile Asp Leu Asp Pro Ile Pro Tyr
2390            2395            2400

Asp Pro Lys Phe Glu Lys Gln Leu Gly Gln Val Met Leu Leu Val
2405            2410            2415

Leu Cys Val Thr Gln Val Leu Met Met Arg Thr Thr Trp Ala Leu
2420            2425            2430

Cys Glu Ala Leu Thr Leu Ala Thr Gly Pro Val Ser Thr Leu Trp
2435            2440            2445

Glu Gly Asn Pro Gly Arg Phe Trp Asn Thr Thr Ile Ala Val Ser
2450            2455            2460

Met Ala Asn Ile Phe Arg Gly Ser Tyr Leu Ala Gly Ala Gly Leu
2465            2470            2475

Leu Phe Ser Ile Met Lys Asn Thr Thr Ser Thr Arg Arg Gly Thr
2480            2485            2490

Gly Asn Ile Gly Glu Thr Leu Gly Glu Lys Trp Lys Ser Arg Leu
2495            2500            2505

Asn Ala Leu Gly Lys Ser Glu Phe Gln Ile Tyr Lys Lys Ser Gly
2510            2515            2520

Ile Gln Glu Val Asp Arg Thr Leu Ala Lys Glu Gly Ile Lys Arg
2525            2530            2535

Gly Glu Thr Asp His His Ala Val Ser Arg Gly Ser Ala Lys Leu
2540            2545            2550

Arg Trp Phe Val Glu Arg Asn Leu Val Thr Pro Glu Gly Lys Val
2555            2560            2565

Val Asp Leu Gly Cys Gly Arg Gly Gly Trp Ser Tyr Tyr Cys Gly
2570            2575            2580

Gly Leu Lys Asn Val Arg Glu Val Lys Gly Leu Thr Lys Gly Gly
2585            2590            2595

Pro Gly His Glu Glu Pro Ile Pro Met Ser Thr Tyr Gly Trp Asn
2600            2605            2610

Leu Val Arg Leu Gln Ser Gly Val Asp Val Phe Phe Val Pro Pro
2615            2620            2625

Glu Lys Cys Asp Thr Leu Leu Cys Asp Ile Gly Glu Ser Ser Pro
2630            2635            2640

Asn Pro Thr Val Glu Ala Gly Arg Thr Leu Arg Val Leu Asn Leu
2645            2650            2655

Val Glu Asn Trp Leu Asn Asn Asn Thr Gln Phe Cys Val Lys Val
2660            2665            2670

Leu Asn Pro Tyr Met Pro Ser Val Ile Glu Arg Met Glu Thr Leu
2675            2680            2685

Gln Arg Lys Tyr Gly Gly Ala Leu Val Arg Asn Pro Leu Ser Arg
2690            2695            2700

Asn Ser Thr His Glu Met Tyr Trp Val Ser Asn Ala Ser Gly Asn
2705            2710            2715

Ile Val Ser Ser Val Asn Met Ile Ser Arg Met Leu Ile Asn Arg
2720            2725            2730

Phe Thr Met Arg His Lys Lys Ala Thr Tyr Glu Pro Asp Val Asp
2735            2740            2745
```

-continued

```
Leu Gly Ser Gly Thr Arg Asn Ile Gly Ile Glu Ser Glu Thr Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Lys Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Glu Val Ser Lys Lys Glu Gly
    3005                3010                3015

Gly Ala Met Tyr Ala Asp Asp Thr Ala Gly Trp Asp Thr Arg Ile
    3020                3025                3030

Thr Ile Glu Asp Leu Lys Asn Glu Glu Met Ile Thr Asn His Met
    3035                3040                3045

Ala Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Ile Phe Lys Ser Ile
    3110                3115                3120

Gln His Leu Thr Ala Ser Glu Glu Ile Ala Val Gln Asp Trp Leu
    3125                3130                3135

Val Arg Val Gly Arg Glu Arg Leu Ser Arg Met Ala Ile Ser Gly
```

```
    3140                3145                3150

Asp Asp  Cys Val Val Lys Pro  Leu Asp Asp Arg Phe  Ala Arg Ala
    3155                3160                3165

Leu Thr  Ala Leu Asn Asp Met  Gly Lys Val Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Thr Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Ile Pro  Thr Ser Arg Thr Thr  Trp Ser Ile
    3275                3280                3285

His Ala  Ser His Glu Trp Met  Thr Thr Glu Asp Met  Leu Thr Val
    3290                3295                3300

Trp Asn  Arg Val Trp Ile Leu  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Thr Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390
```

<210> SEQ ID NO 32
<211> LENGTH: 15053
<212> TYPE: DNA
<213> ORGANISM: Artificial Sequence
<220> FEATURE:
<223> OTHER INFORMATION: Dengue 3 (Sleman/78) plasmid p3

<400> SEQUENCE: 32

```
agttgttagt ctacgtggac cgacaagaac agtttcgact cggaagcttg cttaacgtag     60
tactgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gactgctgaa cggccaagga ccaatgaaat tggttatggc    240
gttcatagct ttcctcagat ttctagccat tccaccgaca gcaggagtct tggctagatg    300
gggaaccttt aagaagtcgg gggctattaa ggtcctgaga ggcttcaaga aggagatctc    360
aaacatgctg agcattatca acagacggaa aaagacatcg ctctgtctca tgatgatgtt    420
accagcaaca cttgctttcc acttgacttc acgagatgga gagccgcgca tgattgtggg    480
gaagaatgaa agaggaaaat ccctactttt taagacagcc tctggaatca acatgtgcac    540
actcatagcc atggatttgg gagagatgtg tgatgacacg gtcacctaca aatgcccccct    600
```

```
cattactgaa gtggagcctg aagacattga ctgctggtgc aaccttacat cgacatgggt      660
gacctacgga acgtgcaatc aagctggaga gcacagacgc gacaaaagat cggtggcgtt      720
agctccccat gtcggcatgg gactggacac acgcacccaa acctggatgt cggctgaagg      780
agcttggaga caggtcgaga aggtagagac atgggccttt aggcacccag ggttcacaat      840
actagcccta tttcttgccc attacatagg cacttccttg acccagaaag tggttatttt      900
catactacta atgctggtca ccccatccat gacaatgaga tgcgtgggag taggaaacag      960
agattttgtg aaggcctat caggagctac gtgggttgac gtggtgctcg agcacggtgg     1020
gtgtgtgact accatggcta agaacaagcc cacgctggat atagagctcc agaagaccga     1080
ggccacccaa ctggcgaccc taaggaaact atgtattgag gaaaaaatta ccaacgtaac     1140
aaccgactca aggtgcccca cccaagggga agcgatttta cctgaggagc aggaccagaa     1200
ccacgtgtgc aagcacacat acgtggacag aggctgggga aacggttgtg gtttgtttgg     1260
caagggaagc ctggtaacat gcgcgaaatt tcaatgtttg gaatcaatag agggaaaagt     1320
ggtgcagcat gagaacctca aatacaccgt catcatcaca gtgcacacag agatcaaca     1380 ccaggtggga aatgaaacgc agggagtcac ggctgagata acaccccagg catcaaccgt     1440
tgaagccatc ttacctgaat atggaacccct gggctagaa tgctcaccac ggacaggttt     1500
agatttcaat gaaatgattt tgttgacaat gaagaacaaa gcatggatgg tacatagaca     1560
atggtttttt gacctacctt taccatggac atcaggagct acaacagaaa caccaacctg     1620
gaataagaaa gagcttcttg tgacattcaa aaacgcacat gcaaaaaagc aagaagtagt     1680
agtccttgga tcgcaagagg gagcaatgca cacagcactg acaggagcta cagagatcca     1740
aacctcagga ggcacaagta tttttgcggg gcacttaaaa tgtagactca agatggacaa     1800
attggaactc aaggggatga gctatgcaat gtgcttgaat gcctttgtgt tgaagaaaga     1860
agtctccgaa acgcaacatg ggacaatact catcaaggtt gagtacaaag gggaagatgc     1920
accttgcaag attcctttct ccacggagga tggacaaggg aaagcccaca tggcagact     1980 gatcacagct aacccagtgg tgaccaagaa ggaggagcct gtcaatattg aggcagaacc     2040
tccttttggg gaaagcaata tagtaattgg aattggagac aaagccttga aaatcaactg     2100
gtacaagaag ggaagctcga ttgggaagat gttcgaggcc actgccagag gtgcaaggcg     2160
catggccatc ttgggagaca cagcctggga cttttggatca gtaggtggtg tttttaaattc     2220 attaggaaaa atggtgcacc aaatatttgg aagtgcttac acagccctat ttagtggagt     2280
ctcctggata atgaaaattg gaataggtgt ccttttaacc tggatagggt tgaattcaaa     2340
aaacactagt atgagcttta gctgcattgt gataggaatc attacactct atctgggagc     2400
cgtggtgcaa gctgacatgg ggtgtgtcat aaactgaaa ggcaaagaac tcaaatgtgg     2460
aagtggaatt ttcgtcacta atgaggtcca cacctggaca gagcaataca aatttcaagc     2520
agactccccc aaaagactgg cgacagccat tgcaggcgct tggagaatg gagtgtgcgg     2580 aatcaggtcg acaaccagaa tggagaacct cttgtggaag caaatagcca atgaactgaa     2640
ctacatatta tgggaaaaca acatcaaatt aacggtagtt gtgggtgata taattgggt     2700 cttagagcaa gggaaagaa cactaacacc acaacccatg gaactaaaat attcatggaa     2760
aacatgggga aaggcgaaga tagtgacagc tgaaacacaa aattcctctt tcataataga     2820
tgggccaaac acaccagagt gtccaagtgc ctcaagagca tggaatgtgt gggaggtgga     2880
agattacggg ttcggagtct tcacaactaa catatggctg aaactccgag agatgtacac     2940
```

```
ccaactatgt gaccacaggc taatgtcggc agccgttaag gatgagaggg ccgtacacgc    3000
cgacatgggc tattggatag aaagccaaaa gaatggaagt tggaagctag aaaaggcatc    3060
cctcatagag gtaaaaacct gcacatggcc aaaatcacac actctttgga gcaatggtgt    3120
gctagagagt gacatgatca tcccaaagag tctggctggt cccatttcgc aacacaacta    3180
caggcccgga taccacaccc aaacggcagg accctggcac ttaggaaaat tggagctgga    3240
cttcaactat tgtgaaggaa caacagttgt catcacagaa aattgtggga caagaggccc    3300
atcactgaga acaacaacag tgtcagggaa gttgatacac gaatggtgtt gccgctcgtg    3360
tacacttcct cccctgcgat acatgggaga agacggctgc tggtatggca tggaaattag    3420
acccattaat gagaaagaag agaacatggt aaagtcttta gtctcagcag ggagtggaaa    3480
ggtggataac ttcacaatgg gtgtcttgtg tttggcaatc cttttttgaag aggtgatgag    3540
aggaaaattt gggaaaaagc acatgattgc aggggttctc ttcacgtttg tactccttct    3600
ctcagggcaa ataacatgga gagacatggc gcacacactc ataatgattg gtccaacgc     3660
ctctgacaga atgggaatgg gcgtcactta cctagcattg attgcaacat ttaaaattca    3720
gccatttttg gctttgggat tcttcctgag gaaactgaca tctagagaaa atttattgtt    3780
gggagttggg ttggccatgg caacaacgtt acaactgcca gaggacattg aacaaatggc    3840
gaatggaata gctttagggc tcatggctct taaattaata acacaatttg aaacatacca    3900
actatggacg gcattagtct ccctaatgtg ttcaaataca attttcacgt tgactgttgc    3960
ctggagaaca gccaccctga ttttggccgg aatttctctt ttgccagtgt gccagtcttc    4020
gagcatgagg aaaacagatt ggctcccaat ggctgtggca gctatgggag ttccacccct    4080
accactttttt attttcagtt tgaaagatac gctcaaaagg agaagctggc cactgaatga    4140
gggggtgatg gctgttggac ttgtgagtat tctagcagt tctctcctta ggaatgacgt    4200
gcccatggct ggaccattag tggctggggg cttgctgata gcgtgctacg tcataactgg    4260
cacgtcagca gacctcactg tagaaaaagc agcagatgtg acatgggagg aagaggctga    4320
gcaaacagga gtgtcccaca atttaatgat cacagttgat gacgatggaa caatgagaat    4380
aaaagatgat gagactgaga acatcttaac agtgcttttg aaaacagcat tactaatagt    4440
gtcaggcatt tttccatact ccatacccgc aacactgttg gtctggcaca cttggcaaaa    4500
gcaaacccaa agatccggtg tcctatggga cgttcccagc cccccagaga cacagaaagc    4560
agaactggaa gaagggggttt ataggatcaa gcagcaagga atttttggga aacccaagt    4620
gggggttgga gtacaaaaag aaggagtttt ccacaccatg tggcacgtca aagaggagc    4680
agtgttgaca cacaatggga aaagactgga accaaactgg gctagcgtga aaaagatct    4740
gatttcatac ggaggaggat ggaaattgag tgcacaatgg caaaaaggag aggaggtgca    4800
ggttattgcc gtagagcctg ggaagaaccc aaagaacttt caaaccatgc caggcattt    4860
ccagacaaca acaggggaga taggagcgat tgcactggac ttcaagcctg gaacttcagg    4920
atctcccatc ataaacagag agggaaaggt actgggattg tatggcaatg agtggtcac    4980
aaagaatggt ggctatgtca gtggaatagc acaaacaaat gcagaaccag acggaccgac    5040
accagagttg gaagaagaga tgttcaaaaa gcgaaatcta accataatgg atctccatcc    5100
cgggtcagga aagacgcgga atatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca caggagaga    5280
gattgttgat ctaatgtgcc acgcaacgtt cacaatgcgt ttgctgtcac cagtcaggt    5340
```

```
tccaaactac aacttgataa taatggatga ggctcatttc acagacccag ccagtatagc    5400
ggctagaggg tacatatcaa ctcgtgtagg aatgggagag gcagccgcaa ttttcatgac    5460
agccacaccc cctggaacag ctgatgcctt tcctcagagc aacgctccaa ttcaagatga    5520
agaaagagac ataccagaac gctcatggaa ttcaggcaat gaatggatta ccgactttgc    5580
cgggaagacg gtgtggtttg tccctagcat caaagctgga aatgacatag caaactgctt    5640
gcggaaaaat ggaaaaaagg tcattcaact tagtaggaag acttttgaca cagaatatca    5700
aaagactaaa ctaaatgatt gggactttgt ggtgacaaca gacatttcag aaatgggagc    5760
caatttcaaa gcagacagag tgatcgaccc aagaagatgt ctcaagccag tgattttgac    5820
agacggaccc gagcgcgtga tcctggcggg accaatgcca gtcaccgtag cgagcgctgc    5880
gcaaaggaga gggagagttg gcaggaaccc acaaaaagaa aatgaccaat acatattcat    5940
gggccagccc ctcaataatg atgaagacca tgctcactgg acagaagcaa aaatgctgct    6000
agacaacatc aacacaccag aagggatcat accagctctc tttgaaccag aaagggagaa    6060
gtcagccgcc atagacggcg aataccgcct gaagggtgag tccaggaaga ccttcgtgga    6120
actcatgagg aggggtgacc tcccagtttg gctagcccat aaagtagcat cagaagggat    6180
caaatataca gatagaaagt ggtgttttga tggagaacgc aacaatcaaa ttttagagga    6240
gaatatggat gtgaaatctg gacaaaggaa ggagaaaaag aaaaaattga gacctaggtg    6300
gcttgatgcc cgcacttatt cagatccctt agcgctcaag gaattcaagg actttgcggc    6360
tggtagaaag tcaattgccc ttgatcttgt gacagaaata ggaagagtgc cttcacactt    6420
agctcacaga acgagaaacg ccctggacaa tctggtgatg ttgcacacgt cagaacatgg    6480
cgggagggcc tacaggcatg cagtggagga actaccagaa acaatggaaa cactcttact    6540
cctgggactc atgatcctgt aacaggtgg agcaatgctt ttcttgatat caggtaaagg    6600
gattggaaag acttcaatag gactcatttg tgtagctgct tccagcggta tgttatggat    6660
ggctgatgtc ccactccaat ggatcgcgtc tgccatagtc ctggagtttt ttatgatggt    6720
gttacttata ccagaaccag aaaagcagag aactccccaa gacaatcaac tcgcatatgt    6780
cgtgataggc atactcacac tggctgcaat agtagcagcc aatgaaatgg gactgttgga    6840
aaccacaaag agagatttag gaatgtccaa agaaccaggt gttgtttctc aaccagcta    6900 tttggatgtg gacttgcacc cagcatcagc ctggacattg tacgctgtgg ccacaacagt    6960
aataacacca atgttgagac ataccataga gaattccaca gcaaatgtgt ccctggcagc    7020 tatgccaac caggcagtgg tcctgatggg tttagacaaa ggatggccga tatcgaaaat    7080
ggacttaggc gtgccactat tggcactggg ttgttattca caagtgaacc cactaactct    7140
cacagcggca gttctcctgc tagtcacgca ttatgctatt ataggtccag gattgcaggc    7200
aaaagccact cgtgaagctc aaaaaaggac agctgctgga ataatgaaga tccaacggt    7260 ggatgggata atgacaatag acctagatcc tgtaatatac gattcaaaat ttgaaaagca    7320
actaggacag gttatgctcc tggttctgtg tgcagttcaa cttttgttaa tgagaacatc    7380
atgggctttt tgtgaagctc taaccctagc cacaggacca ataacaacac tctgggaagg    7440
atcacctggg aagttctgga acaccacgat agctgtttcc atggcgaaca tctttagagg    7500 gagctatta gcaggagctg ggcttgcttt ttctatcatg aaatcagttg gaacaggaaa    7560
gagagggaca gggtcacagg gtgaaacct gggagaaaag tggaaaaaga aattgaatca    7620 attacccgg aaagagtttg acctttacaa gaaatccgga atcactgaag tggatagaac    7680
```

-continued

| | | | | | |
|---|---|---|---|---|---|
| agaagccaaa | gaagggttga | aaagaggaga | aataacacac | catgccgtgt | ccagaggcag | 7740 |
| cgcaaaactt | caatggttcg | tggagagaaa | catggtcatc | cccgaaggaa | gagtcataga | 7800 |
| cttaggctgt | ggaagaggag | gctggtcata | ttattgtgca | ggactgaaaa | aagttacaga | 7860 |
| agtgcgagga | tacacaaaag | gcggcccagg | acatgaagaa | acattggaga | atcttcacca | 7920 |
| agcccaacag | tggaagaaag | cagaaccata | agagtcttga | agatggttga | accatggcta | 7980 |
| aaaaataacc | agttttgcat | taaagtattg | aacccttaca | tgccaactgt | gattgagcac | 8040 |
| ctagaaagac | tacaaaggaa | acatggagga | atgcttgtga | gaaatccact | ctcacgaaac | 8100 |
| tccacgcacg | aaatgtactg | gatatctaat | ggcacaggca | atatcgtttc | ttcagtcaac | 8160 |
| atggtatcca | gattgctact | taacagattc | acaatgacac | ataggagacc | caccatagag | 8220 |
| aaagatgtgg | atttaggagc | ggggacccga | catgtcaatg | cggaaccaga | acacccaac | 8280 |
| atggatgtca | ttggggaaag | aataagaagg | atcaaggagg | agcatagttc | aacatggcac | 8340 |
| tatgatgatg | aaaatcctta | taaaacgtgg | gcttaccatg | gatcctatga | agttaaggcc | 8400 |
| acaggctcag | cctcctccat | gataaatgga | gtcgtgaaac | tcctcacgaa | accatgggat | 8460 |
| gtggtgccca | tggtgacaca | gatggcaatg | acggatacaa | ccccattcgg | ccagcaaagg | 8520 |
| gttttttaaag | agaaagtgga | caccaggaca | cccagaccta | tgccaggaac | aagaaaggtt | 8580 |
| atggagatca | cagcggaatg | gctttggaga | accctgggaa | ggaacaaaag | acccagatta | 8640 |
| tgtacgagag | aggagttcac | aaaaaaggtc | agaaccaacg | cagctatggg | cgccgttttt | 8700 |
| acagaggaga | accaatggga | cagtgctaga | gctgctgttg | aggatgaaga | attctggaaa | 8760 |
| ctcgtggaca | gagaacgtga | actccacaaa | ttgggcaagt | gtggaagctg | cgtttacaac | 8820 |
| atgatgggca | agagagagaa | gaaacttgga | gagtttggca | aagcaaaagg | cagtagagcc | 8880 |
| atatggtaca | tgtggttggg | agccagatac | cttgagttcg | aagcactcgg | attcttaaat | 8940 |
| gaagaccatt | ggttctcgcg | tgaaaactct | tacagtggag | tagaaggaga | aggactgcac | 9000 |
| aagctgggat | acatcttaag | agacatttcc | aagataccg | gaggagctat | gtatgctgat | 9060 |
| gacacagctg | gttgggacac | aagaataaca | gaagatgacc | tgcacaatga | ggaaaaaatc | 9120 |
| acacagcaaa | tggaccctga | acacaggcag | ttagcaaacg | ctatattcaa | gctcacatac | 9180 |
| caaaacaaag | tggtcaaagt | tcaacgacca | actccaaagg | gcacggtaat | ggacatcata | 9240 |
| tctaggaaag | accaaagagg | cagtggacag | gtgggaactt | atggtctgaa | tacattcacc | 9300 |
| aacatggaag | cccagttaat | cagacaaatg | gaaggagaag | gtgtgttgtc | gaaggcagac | 9360 |
| ctcgagaacc | ctcatctgct | agagaagaaa | gttacaat | ggttggaaac | aaaaggagtg | 9420 |
| gagaggttaa | aaagaatggc | catcagcggg | gatgattgcg | tggtgaaacc | aattgatgac | 9480 |
| aggttcgcca | atgccctgct | tgccctgaat | gacatgggaa | aagttaggaa | ggacatacct | 9540 |
| caatggcagc | catcaaaggg | atggcatgat | tggcaacagg | tccctttctg | ctcccaccac | 9600 |
| tttcatgaat | tgatcatgaa | agatggaaga | aagttggtag | ttccctgcag | acctcaggat | 9660 |
| gaattaatcg | ggagagcgag | aatctctcaa | ggagcaggat | ggagccttag | agaaactgca | 9720 |
| tgcctaggga | aagcctacgc | ccaaatgtgg | actctcatgt | actttcacag | aagagatctt | 9780 |
| agactagcat | ccaacgccat | atgttcagca | gtaccagtcc | attgggtccc | cacaagcaga | 9840 |
| acgacgtggt | ctattcatgc | tcaccatcag | tggatgacta | cagaagacat | gcttactgtt | 9900 |
| tggaacaggg | tgtggataga | ggataatcca | tggatggaag | acaaaactcc | agtcaaaacc | 9960 |
| tgggaagatg | ttccatatct | agggaagaga | gaagaccaat | ggtgcggatc | actcattggt | 10020 |
| ctcacttcca | gagcaacctg | ggccagaac | atacttacgg | caatccaaca | ggtgagaagc | 10080 |

```
cttataggca atgaagagtt tctggactac atgccttcga tgaagagatt caggaaggag   10140
gaggagtcag agggagccat ttggtaaacg taggaagtga aaaagaggca aactgtcagg   10200
ccaccttaag ccacagtacg gaagaagctg tgcagcctgt gagccccgtc caaggacgtt   10260
aaaagaagaa gtcaggccca aaagccacgg tttgagcaaa ccgtgctgcc tgtggctccg   10320
tcgtggggac gtaaaacctg ggaggctgca aactgtggaa gctgtacgca cggtgtagca   10380
gactagcggt tagaggagac ccctcccatg acacaacgca gcagcggggc ccgagctctg   10440
agggaagctg tacctccttg caaaggacta gaggttagag gagaccccccc gcaaataaaa   10500 acagcatatt gacgctggga gagaccgagg atcctgctgt ctcctcagca tcattccagg   10560
cacagaacgc cagaaaatgg aatggtgctg ttgaatcaac aggttctggt accggtaggc   10620
atcgtggtgt cacgctcgtc gtttggtatg gcttcattca gctccggttc caacgatca    10680 aggcgagtta catgatcccc catgttgtgc aaaaaagcgg ttagctcctt cggtcctccg   10740
atcgttgtca gaagtaagtt ggccgcagtg ttatcactca tggttatggc agcactgcat   10800
aattctctta ctgtcatgcc atccgtaaga tgcttttctg tgactggtga gtactcaacc   10860
aagtcattct gagaatagtg tatgcggcga ccgagttgct cttgcccggc gtcaacacgg   10920
gataataccg cgccacatag cagaacttta aaagtgctca tcattggaaa acgttcttcg   10980
gggcgaaaac tctcaaggat cttaccgctg ttgagatcca gttcgatgta acccactcgt   11040
gcacccaact gatcttcagc atcttttact ttcaccagcg tttctgggtg agcaaaaaca   11100
ggaaggcaaa atgccgcaaa aaagggaata agggcgacac ggaaatgttg aatactcata   11160
ctcttccttt ttcaatatta ttgaagcatt tatcagggtt attgtctcat gagcggatac   11220
atatttgaat gtatttagaa aaataaacaa atagggggttc gcgcacatt tccccgaaaa   11280 gtgccacctg acgtctaaga aaccattatt atcatgacat taacctataa aaataggcgt   11340
atcacgaggc cctttcgtct tcaagaattc tcatgtttga cagcttatca tcgataagct   11400
ttaatgcggt agtttatcac agttaaattg ctaacgcagt caggcaccgt gtatgaaatc   11460
taacaatgcg ctcatcgtca tcctcggcac cgtcaccctg gatgctgtag gcataggctt   11520
ggttatgccg gtactgccgg gcctcttgcg ggatatcgtc cattccgaca gcatcgccag   11580
tcactatggc gtgctgctgg cgctatatgc gttgatgcaa tttctatgcg cacccgttct   11640
cggagcactg tccgaccgct ttggccgccg cccagtcctg ctcgcttcgc tacttggagc   11700
cactatcgac tacgcgatca tggcgaccac acccgtcctg tggatcctct acgccggacg   11760
catcgtggcc ggcatcaccg gcgccacagg tgcggttgct ggcgcctata tcgccgacat   11820
caccgatggg gaagatcggg ctcgccactt cgggctcatg agcgcttgtt tcggcgtggg   11880
tatggtggca ggccccgtgg ccgggggact gttgggcgcc atctccttgc atgcaccatt   11940
ccttgcggcg gcggtgctca acggcctcaa cctactactg ggctgcttcc taatgcagga   12000
gtcgcataag ggagagcgtc gaccgatgcc cttgagagcc ttcaacccag tcagctcctt   12060
ccggtgggcg cggggcatga ctatcgtcgc cgcacttatg actgtcttct ttatcatgca   12120
actcgtagga caggtgccgg cagcgctctg ggtcattttc ggcgaggacc gctttcgctg   12180
gagcgcgacg atgatcggcc tgtcgcttgc ggtattcgga tcttgcacg ccctcgctca   12240 agccttcgtc actggtcccg ccaccaaacg tttcggcgag aagcaggcca ttatcgccgg   12300
catggcggcc gacgcgctgg gctacgtctt gctggcgttc gcgacgcgag gctgatggc    12360 cttccccatt atgattcttc tcgcttccgg cggcatcggg atgcccgcgt tgcaggccat   12420
```

```
gctgtccagg caggtagatg acgaccatca gggacagctt caaggatcgc tcgcggctct   12480
taccagccta acttcgatca ctggaccgct gatcgtcacg gcgatttatg ccgcctcggc   12540
gagcacatgg aacgggttgg catggattgt aggcgccgcc ctataccttg tctgcctccc   12600
cgcgttgcgt cgcggtgcat ggagccgggc cacctcgacc tgaatggaag ccggcggcac   12660
ctcgctaacg gattcaccac tccaagaatt ggagccaatc aattcttgcg agaactgtg    12720 aatgcgcaaa ccaacccttg gcagaacata tccatcgcgt ccgccatctc cagcagccgc   12780
acgcggcgca tctcgggcag cgttgggtcc tggccacggg tgcgcatgat cgtgctcctg   12840
tcgttgagga cccggctagg ctggcggggt tgccttactg gttagcagaa tgaatcaccg   12900
atacgcgagc gaacgtgaag cgactgctgc tgcaaaacgt ctgcgacctg agcaacaaca   12960
tgaatggtct tcggtttccg tgtttcgtaa agtctggaaa cgcggaagtc agcgccctgc   13020
accattatgt tccggatctg catcgcagga tgctgctggc tacactgtgg aacacctaca   13080
tctgtattaa cgaagcgctg gcattgaccc tgagtgattt ttctctggtc ccgccgcatc   13140
cataccgcca gttgtttacc ctcacaacgt tccagtaacc gggcatgttc atcatcagta   13200
acccgtatcg tgagcatcct ctctcgtttc atcggtatca ttaccccat gaacagaaat    13260 ccccccttaca cggaggcatc agtgaccaaa caggaaaaaa ccgcccttaa catggcccgc   13320
tttatcagaa gccagacatt aacgcttctg gagaaactca acgagctgga cgcggatgaa   13380
caggcagaca tctgtgaatc gcttcacgac cacgctgatg agctttaccg cagctgcctc   13440
gcgcgtttcg gtgatgacgg tgaaaacctc tgacacatgc agctcccgga gacggtcaca   13500
gcttgtctgt aagcggatgc cgggagcaga caagcccgtc agggcgcgtc agcgggtgtt   13560
ggcgggtgtc ggggcgcagc catgacccag tcacgtagcg atagcggagt gtatactggc   13620
ttaactatgc ggcatcagag cagattgtac tgagagtgca ccatatgcgg tgtgaaatac   13680
cgcacagatg cgtaaggaga aaataccgca tcaggcgctc ttccgcttcc tcgctcactg   13740
actcgctgcg ctcggtcgtt cggctgcggc gagcggtatc agctcactca aaggcggtaa   13800
tacggttatc cacagaatca ggggataacg caggaaagaa catgtgagca aaaggccagc   13860
aaaaggccag gaaccgtaaa aaggccgcgt tgctggcgtt tttccatagg ctccgccccc   13920
ctgacgagca tcacaaaaat cgacgctcaa gtcagaggtg gcgaaacccg acaggactat   13980
aaagatacca ggcgtttccc cctggaagct ccctcgtgcg ctctcctgtt ccgaccctgc   14040
cgcttaccgg atacctgtcc gcctttctcc cttcgggaag cgtggcgctt tctcatagct   14100
cacgctgtag gtatctcagt tcggtgtagg tcgttcgctc caagctgggc tgtgtgcacg   14160 aacccccgt tcagcccgac cgctgcgcct tatccggtaa ctatcgtctt gagtccaacc    14220
cggtaagaca cgacttatcg ccactggcag cagccactgg taacaggatt agcagagcga   14280
ggtatgtagg cggtgctaca gagttcttga agtggtggcc taactacggc tacactagaa   14340
ggacagtatt tggtatctgc gctctgctga agccagttac cttcggaaaa agagttggta   14400
gctcttgatc cggcaaacaa accaccgctg gtagcggtgg ttttttgtt tgcaagcagc    14460 agattacgcg cagaaaaaaa ggatctcaag aagatccttt gatcttttct acggggtctg   14520
acgctcagtg gaacgaaaac tcacgttaag ggattttggt catgagatta tcaaaaagga   14580
tcttcaccta gatccttta aattaaaaat gaagttttaa atcaatctaa agtatatatg    14640
agtaaacttg gtctgacagt taccaatgct taatcagtga ggcacctatc tcagcgatct   14700
gtctatttcg ttcatccata gttgcctgac tccccgtcgt gtagataact acgatacggg   14760
agggcttacc atctggcccc agtgctgcaa tgataccgcg agacccacgc tcaccggctc   14820
```

```
cagatttatc agcaataaac cagccagccg gaagggccga gcgcagaagt ggtcctgcaa    14880
ctttatccgc ctccatccag tctattaatt gttgccggga agctagagta agtagttcgc    14940
cagttaatag tttgcgcaac gttgttgcca ttgctgcaag atctggctag cgatgaccct    15000
gctgattggt tcgctgacca tttccgggcg cgccgattta ggtgacacta tag           15053
```

<210> SEQ ID NO 33
<211> LENGTH: 3390
<212> TYPE: PRT
<213> ORGANISM: Dengue 3 (Sleman/78)

<400> SEQUENCE: 33

```
Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Arg Gly Phe Lys Lys Glu Ile Ser Asn Met Leu Ser Ile Ile Asn
                85                  90                  95

Arg Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro Leu Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Phe Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335
```

```
Arg Lys Leu Cys Ile Glu Gly Lys Ile Thr Asn Val Thr Thr Asp Ser
            340                 345                 350

Arg Cys Pro Thr Gln Gly Glu Ala Ile Leu Pro Glu Gln Asp Gln
            355                 360                 365

Asn His Val Cys Lys His Thr Tyr Val Asp Arg Gly Trp Gly Asn Gly
            370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Gln His Glu Asn Leu Lys
            405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
            435                 440                 445

Val Glu Ala Ile Leu Pro Glu Tyr Gly Thr Leu Gly Leu Glu Cys Ser
            450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
            485                 490                 495

Pro Trp Thr Ser Gly Ala Thr Thr Glu Thr Pro Thr Trp Asn Lys Lys
            500                 505                 510

Glu Leu Leu Val Thr Phe Lys Asn Ala His Ala Lys Lys Gln Glu Val
            515                 520                 525

Val Val Leu Gly Ser Gln Glu Gly Ala Met His Thr Ala Leu Thr Gly
            530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
            565                 570                 575

Tyr Ala Met Cys Leu Asn Ala Phe Val Leu Lys Lys Glu Val Ser Glu
            580                 585                 590

Thr Gln His Gly Thr Ile Leu Ile Lys Val Glu Tyr Lys Gly Glu Asp
            595                 600                 605

Ala Pro Cys Lys Ile Pro Phe Ser Thr Glu Asp Gly Gln Gly Lys Ala
610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
            645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
            675                 680                 685

Arg Met Ala Ile Leu Gly Asp Thr Ala Trp Asp Phe Gly Ser Val Gly
            690                 695                 700

Gly Val Leu Asn Ser Leu Gly Lys Met Val His Gln Ile Phe Gly Ser
705                 710                 715                 720

Ala Tyr Thr Ala Leu Phe Ser Gly Val Ser Trp Ile Met Lys Ile Gly
            725                 730                 735

Ile Gly Val Leu Leu Thr Trp Ile Gly Leu Asn Ser Lys Asn Thr Ser
            740                 745                 750
```

```
Met Ser Phe Ser Cys Ile Val Ile Gly Ile Ile Thr Leu Tyr Leu Gly
            755                 760                 765
Ala Val Val Gln Ala Asp Met Gly Cys Val Ile Asn Trp Lys Gly Lys
        770                 775                 780
Glu Leu Lys Cys Gly Ser Gly Ile Phe Val Thr Asn Glu Val His Thr
785                 790                 795                 800
Trp Thr Glu Gln Tyr Lys Phe Gln Ala Asp Ser Pro Lys Arg Leu Ala
                805                 810                 815
Thr Ala Ile Ala Gly Ala Trp Glu Asn Gly Val Cys Gly Ile Arg Ser
            820                 825                 830
Thr Thr Arg Met Glu Asn Leu Leu Trp Lys Gln Ile Ala Asn Glu Leu
        835                 840                 845
Asn Tyr Ile Leu Trp Glu Asn Asn Ile Lys Leu Thr Val Val Val Gly
850                 855                 860
Asp Ile Ile Gly Val Leu Glu Gln Gly Lys Arg Thr Leu Thr Pro Gln
865                 870                 875                 880
Pro Met Glu Leu Lys Tyr Ser Trp Lys Thr Trp Gly Lys Ala Lys Ile
                885                 890                 895
Val Thr Ala Glu Thr Gln Asn Ser Ser Phe Ile Ile Asp Gly Pro Asn
            900                 905                 910
Thr Pro Glu Cys Pro Ser Ala Ser Arg Ala Trp Asn Val Trp Glu Val
        915                 920                 925
Glu Asp Tyr Gly Phe Gly Val Phe Thr Thr Asn Ile Trp Leu Lys Leu
        930                 935                 940
Arg Glu Met Tyr Thr Gln Leu Cys Asp His Arg Leu Met Ser Ala Ala
945                 950                 955                 960
Val Lys Asp Glu Arg Ala Val His Ala Asp Met Gly Tyr Trp Ile Glu
                965                 970                 975
Ser Gln Lys Asn Gly Ser Trp Lys Leu Glu Lys Ala Ser Leu Ile Glu
            980                 985                 990
Val Lys Thr Cys Thr Trp Pro Lys Ser His Thr Leu Trp Ser Asn Gly
        995                 1000                1005
Val Leu Glu Ser Asp Met Ile Ile Pro Lys Ser Leu Ala Gly Pro
    1010                1015                1020
Ile Ser Gln His Asn Tyr Arg Pro Gly Tyr His Thr Gln Thr Ala
    1025                1030                1035
Gly Pro Trp His Leu Gly Lys Leu Glu Leu Asp Phe Asn Tyr Cys
    1040                1045                1050
Glu Gly Thr Thr Val Val Ile Thr Glu Asn Cys Gly Thr Arg Gly
    1055                1060                1065
Pro Ser Leu Arg Thr Thr Thr Val Ser Gly Lys Leu Ile His Glu
    1070                1075                1080
Trp Cys Cys Arg Ser Cys Thr Leu Pro Pro Leu Arg Tyr Met Gly
    1085                1090                1095
Glu Asp Gly Cys Trp Tyr Gly Met Glu Ile Arg Pro Ile Asn Glu
    1100                1105                1110
Lys Glu Glu Asn Met Val Lys Ser Leu Val Ser Ala Gly Ser Gly
    1115                1120                1125
Lys Val Asp Asn Phe Thr Met Gly Val Leu Cys Leu Ala Ile Leu
    1130                1135                1140
Phe Glu Glu Val Met Arg Gly Lys Phe Gly Lys Lys His Met Ile
    1145                1150                1155
Ala Gly Val Leu Phe Thr Phe Val Leu Leu Leu Ser Gly Gln Ile
```

```
            1160                1165                1170
Thr Trp Arg Asp Met Ala His Thr Leu Ile Met Ile Gly Ser Asn
    1175                1180                1185
Ala Ser Asp Arg Met Gly Met Gly Val Thr Tyr Leu Ala Leu Ile
    1190                1195                1200
Ala Thr Phe Lys Ile Gln Pro Phe Leu Ala Leu Gly Phe Phe Leu
    1205                1210                1215
Arg Lys Leu Thr Ser Arg Glu Asn Leu Leu Leu Gly Val Gly Leu
    1220                1225                1230
Ala Met Ala Thr Thr Leu Gln Leu Pro Glu Asp Ile Glu Gln Met
    1235                1240                1245
Ala Asn Gly Ile Ala Leu Gly Leu Met Ala Leu Lys Leu Ile Thr
    1250                1255                1260
Gln Phe Glu Thr Tyr Gln Leu Trp Thr Ala Leu Val Ser Leu Met
    1265                1270                1275
Cys Ser Asn Thr Ile Phe Thr Leu Thr Val Ala Trp Arg Thr Ala
    1280                1285                1290
Thr Leu Ile Leu Ala Gly Ile Ser Leu Leu Pro Val Cys Gln Ser
    1295                1300                1305
Ser Ser Met Arg Lys Thr Asp Trp Leu Pro Met Ala Val Ala Ala
    1310                1315                1320
Met Gly Val Pro Pro Leu Pro Leu Phe Ile Phe Ser Leu Lys Asp
    1325                1330                1335
Thr Leu Lys Arg Arg Ser Trp Pro Leu Asn Glu Gly Val Met Ala
    1340                1345                1350
Val Gly Leu Val Ser Ile Leu Ala Ser Ser Leu Leu Arg Asn Asp
    1355                1360                1365
Val Pro Met Ala Gly Pro Leu Val Ala Gly Gly Leu Leu Ile Ala
    1370                1375                1380
Cys Tyr Val Ile Thr Gly Thr Ser Ala Asp Leu Thr Val Glu Lys
    1385                1390                1395
Ala Ala Asp Val Thr Trp Glu Glu Ala Glu Gln Thr Gly Val
    1400                1405                1410
Ser His Asn Leu Met Ile Thr Val Asp Asp Gly Thr Met Arg
    1415                1420                1425
Ile Lys Asp Asp Glu Thr Glu Asn Ile Leu Thr Val Leu Leu Lys
    1430                1435                1440
Thr Ala Leu Leu Ile Val Ser Gly Ile Phe Pro Tyr Ser Ile Pro
    1445                1450                1455
Ala Thr Leu Leu Val Trp His Thr Trp Gln Lys Gln Thr Gln Arg
    1460                1465                1470
Ser Gly Val Leu Trp Asp Val Pro Ser Pro Pro Glu Thr Gln Lys
    1475                1480                1485
Ala Glu Leu Glu Glu Gly Val Tyr Arg Ile Lys Gln Gln Gly Ile
    1490                1495                1500
Phe Gly Lys Thr Gln Val Gly Val Gly Val Gln Lys Glu Gly Val
    1505                1510                1515
Phe His Thr Met Trp His Val Thr Arg Gly Ala Val Leu Thr His
    1520                1525                1530
Asn Gly Lys Arg Leu Glu Pro Asn Trp Ala Ser Val Lys Lys Asp
    1535                1540                1545
Leu Ile Ser Tyr Gly Gly Gly Trp Lys Leu Ser Ala Gln Trp Gln
    1550                1555                1560
```

-continued

```
Lys Gly Glu Glu Val Gln Val Ile Ala Val Glu Pro Gly Lys Asn
    1565                1570                1575
Pro Lys Asn Phe Gln Thr Met Pro Gly Ile Phe Gln Thr Thr Thr
    1580                1585                1590
Gly Glu Ile Gly Ala Ile Ala Leu Asp Phe Lys Pro Gly Thr Ser
    1595                1600                1605
Gly Ser Pro Ile Ile Asn Arg Glu Gly Lys Val Leu Gly Leu Tyr
    1610                1615                1620
Gly Asn Gly Val Val Thr Lys Asn Gly Gly Tyr Val Ser Gly Ile
    1625                1630                1635
Ala Gln Thr Asn Ala Glu Pro Asp Gly Pro Thr Pro Glu Leu Glu
    1640                1645                1650
Glu Glu Met Phe Lys Lys Arg Asn Leu Thr Ile Met Asp Leu His
    1655                1660                1665
Pro Gly Ser Gly Lys Thr Arg Lys Tyr Leu Pro Ala Ile Val Arg
    1670                1675                1680
Glu Ala Ile Lys Arg Arg Leu Arg Thr Leu Ile Leu Ala Pro Thr
    1685                1690                1695
Arg Val Val Ala Ala Glu Met Glu Glu Ala Leu Lys Gly Leu Pro
    1700                1705                1710
Ile Arg Tyr Gln Thr Thr Ala Thr Lys Ser Glu His Thr Gly Arg
    1715                1720                1725
Glu Ile Val Asp Leu Met Cys His Ala Thr Phe Thr Met Arg Leu
    1730                1735                1740
Leu Ser Pro Val Arg Val Pro Asn Tyr Asn Leu Ile Ile Met Asp
    1745                1750                1755
Glu Ala His Phe Thr Asp Pro Ala Ser Ile Ala Ala Arg Gly Tyr
    1760                1765                1770
Ile Ser Thr Arg Val Gly Met Gly Glu Ala Ala Ala Ile Phe Met
    1775                1780                1785
Thr Ala Thr Pro Pro Gly Thr Ala Asp Ala Phe Pro Gln Ser Asn
    1790                1795                1800
Ala Pro Ile Gln Asp Glu Glu Arg Asp Ile Pro Glu Arg Ser Trp
    1805                1810                1815
Asn Ser Gly Asn Glu Trp Ile Thr Asp Phe Ala Gly Lys Thr Val
    1820                1825                1830
Trp Phe Val Pro Ser Ile Lys Ala Gly Asn Asp Ile Ala Asn Cys
    1835                1840                1845
Leu Arg Lys Asn Gly Lys Lys Val Ile Gln Leu Ser Arg Lys Thr
    1850                1855                1860
Phe Asp Thr Glu Tyr Gln Lys Thr Lys Leu Asn Asp Trp Asp Phe
    1865                1870                1875
Val Val Thr Thr Asp Ile Ser Glu Met Gly Ala Asn Phe Lys Ala
    1880                1885                1890
Asp Arg Val Ile Asp Pro Arg Arg Cys Leu Lys Pro Val Ile Leu
    1895                1900                1905
Thr Asp Gly Pro Glu Arg Val Ile Leu Ala Gly Pro Met Pro Val
    1910                1915                1920
Thr Val Ala Ser Ala Ala Gln Arg Arg Gly Arg Val Gly Arg Asn
    1925                1930                1935
Pro Gln Lys Glu Asn Asp Gln Tyr Ile Phe Met Gly Gln Pro Leu
    1940                1945                1950
```

```
Asn Asn Asp Glu Asp His Ala His Trp Thr Glu Ala Lys Met Leu
    1955            1960                1965

Leu Asp Asn Ile Asn Thr Pro Glu Gly Ile Ile Pro Ala Leu Phe
    1970            1975                1980

Glu Pro Glu Arg Glu Lys Ser Ala Ala Ile Asp Gly Glu Tyr Arg
    1985            1990                1995

Leu Lys Gly Glu Ser Arg Lys Thr Phe Val Glu Leu Met Arg Arg
    2000            2005                2010

Gly Asp Leu Pro Val Trp Leu Ala His Lys Val Ala Ser Glu Gly
    2015            2020                2025

Ile Lys Tyr Thr Asp Arg Lys Trp Cys Phe Asp Gly Glu Arg Asn
    2030            2035                2040

Asn Gln Ile Leu Glu Glu Asn Met Asp Val Glu Ile Trp Thr Lys
    2045            2050                2055

Glu Gly Glu Lys Lys Lys Leu Arg Pro Arg Trp Leu Asp Ala Arg
    2060            2065                2070

Thr Tyr Ser Asp Pro Leu Ala Leu Lys Glu Phe Lys Asp Phe Ala
    2075            2080                2085

Ala Gly Arg Lys Ser Ile Ala Leu Asp Leu Val Thr Glu Ile Gly
    2090            2095                2100

Arg Val Pro Ser His Leu Ala His Arg Thr Arg Asn Ala Leu Asp
    2105            2110                2115

Asn Leu Val Met Leu His Thr Ser Glu His Gly Gly Arg Ala Tyr
    2120            2125                2130

Arg His Ala Val Glu Glu Leu Pro Glu Thr Met Glu Thr Leu Leu
    2135            2140                2145

Leu Leu Gly Leu Met Ile Leu Leu Thr Gly Gly Ala Met Leu Phe
    2150            2155                2160

Leu Ile Ser Gly Lys Gly Ile Gly Lys Thr Ser Ile Gly Leu Ile
    2165            2170                2175

Cys Val Ala Ala Ser Ser Gly Met Leu Trp Met Ala Asp Val Pro
    2180            2185                2190

Leu Gln Trp Ile Ala Ser Ala Ile Val Leu Glu Phe Phe Met Met
    2195            2200                2205

Val Leu Leu Ile Pro Glu Pro Glu Lys Gln Arg Thr Pro Gln Asp
    2210            2215                2220

Asn Gln Leu Ala Tyr Val Val Ile Gly Ile Leu Thr Leu Ala Ala
    2225            2230                2235

Ile Val Ala Ala Asn Glu Met Gly Leu Leu Glu Thr Thr Lys Arg
    2240            2245                2250

Asp Leu Gly Met Ser Lys Glu Pro Gly Val Val Ser Pro Thr Ser
    2255            2260                2265

Tyr Leu Asp Val Asp Leu His Pro Ala Ser Ala Trp Thr Leu Tyr
    2270            2275                2280

Ala Val Ala Thr Thr Val Ile Thr Pro Met Leu Arg His Thr Ile
    2285            2290                2295

Glu Asn Ser Thr Ala Asn Val Ser Leu Ala Ala Ile Ala Asn Gln
    2300            2305                2310

Ala Val Val Leu Met Gly Leu Asp Lys Gly Trp Pro Ile Ser Lys
    2315            2320                2325

Met Asp Leu Gly Val Pro Leu Leu Ala Leu Gly Cys Tyr Ser Gln
    2330            2335                2340

Val Asn Pro Leu Thr Leu Thr Ala Ala Val Leu Leu Leu Val Thr
```

```
            2345                2350                2355
His Tyr Ala Ile Ile Gly Pro Gly Leu Gln Ala Lys Ala Thr Arg
            2360                2365                2370
Glu Ala Gln Lys Arg Thr Ala Ala Gly Ile Met Lys Asn Pro Thr
            2375                2380                2385
Val Asp Gly Ile Met Thr Ile Asp Leu Asp Pro Val Ile Tyr Asp
            2390                2395                2400
Ser Lys Phe Glu Lys Gln Leu Gly Gln Val Met Leu Leu Val Leu
            2405                2410                2415
Cys Ala Val Gln Leu Leu Leu Met Arg Thr Ser Trp Ala Phe Cys
            2420                2425                2430
Glu Ala Leu Thr Leu Ala Thr Gly Pro Ile Thr Thr Leu Trp Glu
            2435                2440                2445
Gly Ser Pro Gly Lys Phe Trp Asn Thr Thr Ile Ala Val Ser Met
            2450                2455                2460
Ala Asn Ile Phe Arg Gly Ser Tyr Leu Ala Gly Ala Gly Leu Ala
            2465                2470                2475
Phe Ser Ile Met Lys Ser Val Gly Thr Gly Lys Arg Gly Thr Gly
            2480                2485                2490
Ser Gln Gly Glu Thr Leu Gly Glu Lys Trp Lys Lys Lys Leu Asn
            2495                2500                2505
Gln Leu Pro Arg Lys Glu Phe Asp Leu Tyr Lys Lys Ser Gly Ile
            2510                2515                2520
Thr Glu Val Asp Arg Thr Glu Ala Lys Glu Gly Leu Lys Arg Gly
            2525                2530                2535
Glu Ile Thr His His Ala Val Ser Arg Gly Ser Ala Lys Leu Gln
            2540                2545                2550
Trp Phe Val Glu Arg Asn Met Val Ile Pro Glu Gly Arg Val Ile
            2555                2560                2565
Asp Leu Gly Cys Gly Arg Gly Gly Trp Ser Tyr Tyr Cys Ala Gly
            2570                2575                2580
Leu Lys Lys Val Thr Glu Val Arg Gly Tyr Thr Lys Gly Gly Pro
            2585                2590                2595
Gly His Glu Glu Pro Val Pro Met Ser Thr Tyr Gly Trp Asn Ile
            2600                2605                2610
Val Lys Leu Met Ser Gly Lys Asp Val Phe Tyr Leu Pro Pro Glu
            2615                2620                2625
Lys Cys Asp Thr Leu Leu Cys Asp Ile Gly Glu Ser Ser Pro Ser
            2630                2635                2640
Pro Thr Val Glu Glu Ser Arg Thr Ile Arg Val Leu Lys Met Val
            2645                2650                2655
Glu Pro Trp Leu Lys Asn Asn Gln Phe Cys Ile Lys Val Leu Asn
            2660                2665                2670
Pro Tyr Met Pro Thr Val Ile Glu His Leu Glu Arg Leu Gln Arg
            2675                2680                2685
Lys His Gly Gly Met Leu Val Arg Asn Pro Leu Ser Arg Asn Ser
            2690                2695                2700
Thr His Glu Met Tyr Trp Ile Ser Asn Gly Thr Gly Asn Ile Val
            2705                2710                2715
Ser Ser Val Asn Met Val Ser Arg Leu Leu Leu Asn Arg Phe Thr
            2720                2725                2730
Met Thr His Arg Arg Pro Thr Ile Glu Lys Asp Val Asp Leu Gly
            2735                2740                2745
```

-continued

```
Ala Gly Thr Arg His Val Asn Ala Glu Pro Glu Thr Pro Asn Met
    2750            2755                2760

Asp Val Ile Gly Glu Arg Ile Arg Arg Ile Lys Glu Glu His Ser
    2765            2770                2775

Ser Thr Trp His Tyr Asp Asp Glu Asn Pro Tyr Lys Thr Trp Ala
    2780            2785                2790

Tyr His Gly Ser Tyr Glu Val Lys Ala Thr Gly Ser Ala Ser Ser
    2795            2800                2805

Met Ile Asn Gly Val Val Lys Leu Leu Thr Lys Pro Trp Asp Val
    2810            2815                2820

Val Pro Met Val Thr Gln Met Ala Met Thr Asp Thr Thr Pro Phe
    2825            2830                2835

Gly Gln Gln Arg Val Phe Lys Glu Lys Val Asp Thr Arg Thr Pro
    2840            2845                2850

Arg Pro Met Pro Gly Thr Arg Lys Val Met Glu Ile Thr Ala Glu
    2855            2860                2865

Trp Leu Trp Arg Thr Leu Gly Arg Asn Lys Arg Pro Arg Leu Cys
    2870            2875                2880

Thr Arg Glu Glu Phe Thr Lys Lys Val Arg Thr Asn Ala Ala Met
    2885            2890                2895

Gly Ala Val Phe Thr Glu Glu Asn Gln Trp Asp Ser Ala Arg Ala
    2900            2905                2910

Ala Val Glu Asp Glu Glu Phe Trp Lys Leu Val Asp Arg Glu Arg
    2915            2920                2925

Glu Leu His Lys Leu Gly Lys Cys Gly Ser Cys Val Tyr Asn Met
    2930            2935                2940

Met Gly Lys Arg Glu Lys Lys Leu Gly Glu Phe Gly Lys Ala Lys
    2945            2950                2955

Gly Ser Arg Ala Ile Trp Tyr Met Trp Leu Gly Ala Arg Tyr Leu
    2960            2965                2970

Glu Phe Glu Ala Leu Gly Phe Leu Asn Glu Asp His Trp Phe Ser
    2975            2980                2985

Arg Glu Asn Ser Tyr Ser Gly Val Glu Gly Glu Gly Leu His Lys
    2990            2995                3000

Leu Gly Tyr Ile Leu Arg Asp Ile Ser Lys Ile Pro Gly Gly Ala
    3005            3010                3015

Met Tyr Ala Asp Asp Thr Ala Gly Trp Asp Thr Arg Ile Thr Glu
    3020            3025                3030

Asp Asp Leu His Asn Glu Glu Lys Ile Thr Gln Gln Met Asp Pro
    3035            3040                3045

Glu His Arg Gln Leu Ala Asn Ala Ile Phe Lys Leu Thr Tyr Gln
    3050            3055                3060

Asn Lys Val Val Lys Val Gln Arg Pro Thr Pro Lys Gly Thr Val
    3065            3070                3075

Met Asp Ile Ile Ser Arg Lys Asp Gln Arg Gly Ser Gly Gln Val
    3080            3085                3090

Gly Thr Tyr Gly Leu Asn Thr Phe Thr Asn Met Glu Ala Gln Leu
    3095            3100                3105

Ile Arg Gln Met Glu Gly Glu Gly Val Leu Ser Lys Ala Asp Leu
    3110            3115                3120

Glu Asn Pro His Leu Leu Glu Lys Lys Val Thr Gln Trp Leu Glu
    3125            3130                3135
```

```
Thr Lys Gly Val Glu Arg Leu Lys Arg Met Ala Ile Ser Gly Asp
3140                3145                3150

Asp Cys Val Val Lys Pro Ile Asp Asp Arg Phe Ala Asn Ala Leu
3155                3160                3165

Leu Ala Leu Asn Asp Met Gly Lys Val Arg Lys Asp Ile Pro Gln
3170                3175                3180

Trp Gln Pro Ser Lys Gly Trp His Asp Trp Gln Gln Val Pro Phe
3185                3190                3195

Cys Ser His His Phe His Glu Leu Ile Met Lys Asp Gly Arg Lys
3200                3205                3210

Leu Val Val Pro Cys Arg Pro Gln Asp Glu Leu Ile Gly Arg Ala
3215                3220                3225

Arg Ile Ser Gln Gly Ala Gly Trp Ser Leu Arg Glu Thr Ala Cys
3230                3235                3240

Leu Gly Lys Ala Tyr Ala Gln Met Trp Thr Leu Met Tyr Phe His
3245                3250                3255

Arg Arg Asp Leu Arg Leu Ala Ser Asn Ala Ile Cys Ser Ala Val
3260                3265                3270

Pro Val His Trp Val Pro Thr Ser Arg Thr Thr Trp Ser Ile His
3275                3280                3285

Ala His His Gln Trp Met Thr Thr Glu Asp Met Leu Thr Val Trp
3290                3295                3300

Asn Arg Val Trp Ile Glu Asp Asn Pro Trp Met Glu Asp Lys Thr
3305                3310                3315

Pro Val Lys Thr Trp Glu Asp Val Pro Tyr Leu Gly Lys Arg Glu
3320                3325                3330

Asp Gln Trp Cys Gly Ser Leu Ile Gly Leu Thr Ser Arg Ala Thr
3335                3340                3345

Trp Ala Gln Asn Ile Leu Thr Ala Ile Gln Gln Val Arg Ser Leu
3350                3355                3360

Ile Gly Asn Glu Glu Phe Leu Asp Tyr Met Pro Ser Met Lys Arg
3365                3370                3375

Phe Arg Lys Glu Glu Glu Ser Glu Gly Ala Ile Trp
3380                3385                3390

<210> SEQ ID NO 34
<211> LENGTH: 51
<212> TYPE: DNA
<213> ORGANISM: Artificial Sequence
<220> FEATURE:
<223> OTHER INFORMATION: Forward primer

<400> SEQUENCE: 34
tcaaaacaaa agaaaagatc tgcagtgacc ggaattgcag tcatgattgg c        51

<210> SEQ ID NO 35
<211> LENGTH: 51
<212> TYPE: DNA
<213> ORGANISM: Artificial Sequence
<220> FEATURE:
<223> OTHER INFORMATION: Forward primer

<400> SEQUENCE: 35
tcaaaacaaa agaaaagatc tgcagggacc ggaattgcag tcatgattgg c        51

<210> SEQ ID NO 36
<211> LENGTH: 51
<212> TYPE: DNA
```

```
<213> ORGANISM: Artificial Sequence
<220> FEATURE:
<223> OTHER INFORMATION: Forward primer

<400> SEQUENCE: 36
tcaaaacaaa agaaaagatc tgcagacacc ggaattgcag tcatgattgg c        51

<210> SEQ ID NO 37
<211> LENGTH: 64
<212> TYPE: DNA
<213> ORGANISM: Artificial Sequence
<220> FEATURE:
<223> OTHER INFORMATION: Reverse primer

<400> SEQUENCE: 37
ccgcaagaaa cgtcatagca attgacctgt cactcgagtt gattcccatc cacaacagaa    60
gagc                                                                 64
```

What is claimed is:

1. A nucleic acid chimera comprising a first nucleotide sequence encoding two structural proteins from a West Nile virus, wherein the structural proteins are premembrane/membrane (prM) and envelope (E), and a second nucleotide sequence encoding capsid (C) and nonstructural proteins from a dengue type 1 virus, dengue type 2 virus, or dengue type 3 virus, wherein the dengue virus is attenuated by a deletion of about 30 nucleotides from the 3' untranslated region of the dengue genome corresponding to the TL2 stem-loop structure and wherein a cleavage site is utilized for joining the dengue virus capsid protein and the West Nile virus prM protein, and wherein the West Nile virus prM protein contains aspartic acid (Asp) at a position 3 amino acids downstream of the cleavage site and contains threonine (Thr) at a position 6 amino acids downstream of the cleavage site wherein the cleavage site corresponds to amino acid position 3 of SEQ ID NO: 3.

2. The nucleic acid chimera of claim 1, wherein the dengue virus is an attenuated virus or a virus adapted for increased growth in Vero cells.

3. The nucleic acid chimera of claim 1, wherein the dengue virus is dengue type 1 virus and the virus is attenuated by a deletion of about 30 nucleotides from the 3' untranslated region of the dengue type 1 genome corresponding to the TL2 stem-loop structure between about nucleotides 10562-10591.

4. The nucleic acid chimera of claim 1, wherein the dengue virus is dengue type 2 virus and the virus is attenuated by a deletion of about 30 nucleotides from the 3' untranslated region of the dengue type 2 genome corresponding to the TL2 stem-loop structure between about nucleotides 10541-10570.

5. The nucleic acid chimera of claim 1, wherein the dengue virus is dengue type 3 virus and the virus is attenuated by a deletion of about 30 nucleotides from the 3' untranslated region of the dengue type 3 genome corresponding to the TL2 stem-loop structure between about nucleotides 10535-10565.

6. A virus chimera comprising one or more than one nucleic acid chimera of claim 1.

7. An immunogenic composition comprising one or more than one nucleic acid chimera of claim 1 and a pharmaceutically acceptable carrier.

8. A method of inducing an immune response in a subject comprising administering an effective amount of the composition of claim 7 to the subject.

9. The method of claim 8 wherein the subject is a non-human primate, a human, a horse, or a bird.

10. A vaccine composition comprising one or more than one nucleic acid chimera of claim 1 and a pharmaceutically acceptable carrier.

11. A method of immunizing a subject against West Nile virus infection comprising administering an effective amount of the composition of claim 10 to the subject.

12. The method of claim 11 wherein the subject is a non-human primate, a human, a horse, or a bird.

* * * * *